US012649793B2

(12) United States Patent
Short et al.

(10) Patent No.: US 12,649,793 B2
(45) Date of Patent: ***Jun. 9, 2026

(54) ANTI-CTLA4 ANTIBODIES, ANTIBODY FRAGMENTS, THEIR IMMUNOCONJUGATES AND USES THEREOF

(71) Applicant: BioAtla, Inc., San Diego, CA (US)

(72) Inventors: Jay M. Short, Jackson, WY (US); Gerhard Frey, San Diego, CA (US); Hwai Wen Chang, San Marcos, CA (US)

(73) Assignee: BioAtla, Inc., San Diego, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 18/056,681

(22) Filed: Nov. 17, 2022

(65) Prior Publication Data

US 2023/0192858 A1     Jun. 22, 2023

Related U.S. Application Data

(63) Continuation of application No. 17/288,187, filed as application No. PCT/US2019/058066 on Oct. 25, 2019, now Pat. No. 11,542,332.

(60) Provisional application No. 62/823,992, filed on Mar. 26, 2019, provisional application No. 62/824,014, filed on Mar. 26, 2019, provisional application No. 62/822,971, filed on Mar. 24, 2019, provisional application No. 62/803,060, filed on Feb. 8, 2019, provisional application No. 62/798,234, filed on Jan. 29, 2019, provisional application No. 62/753,498, filed on Oct. 31, 2018.

(51) Int. Cl.
| | |
|---|---|
| *C07K 16/28* | (2006.01) |
| *A61K 39/395* | (2006.01) |
| *A61K 47/68* | (2017.01) |
| *A61P 35/00* | (2006.01) |
| *G01N 33/575* | (2026.01) |

(52) U.S. Cl.
CPC ...... *C07K 16/2818* (2013.01); *A61K 47/6849* (2017.08); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,885,579 A | 3/1999 | Linsley et al. |
| 5,885,796 A | 3/1999 | Linsley et al. |
| 5,968,510 A | 10/1999 | Linsley et al. |
| 5,977,318 A | 11/1999 | Linsley et al. |
| 6,682,736 B1 | 1/2004 | Hanson et al. |
| 6,984,720 B1 | 1/2006 | Korman et al. |
| 7,329,737 B2 | 2/2008 | Sexton et al. |
| 7,387,776 B2 | 6/2008 | Keler et al. |
| 7,411,057 B2 | 8/2008 | Hanson et al. |
| 7,514,534 B2 | 4/2009 | Dransfield et al. |
| 7,605,238 B2 | 10/2009 | Korman et al. |
| 7,790,160 B2 | 9/2010 | Von Strandmann et al. |
| 7,879,985 B2 | 2/2011 | Urso et al. |
| 7,943,743 B2 | 5/2011 | Korman et al. |
| 7,993,646 B2 | 8/2011 | Sexton et al. |
| 8,017,114 B2 | 9/2011 | Korman et al. |
| 8,062,866 B2 | 11/2011 | Frey et al. |
| 8,071,323 B2 | 12/2011 | Dimitrov et al. |
| 8,110,194 B2 | 2/2012 | Nichol et al. |
| 8,142,778 B2 | 3/2012 | Davis et al. |
| 8,173,398 B2 | 5/2012 | Frey et al. |
| 8,318,916 B2 | 11/2012 | Korman et al. |
| 8,435,516 B2 | 5/2013 | Huang et al. |
| 8,491,895 B2 | 7/2013 | Hanson et al. |
| 8,551,476 B2 | 10/2013 | Mi et al. |
| 8,697,845 B2 | 4/2014 | Ward et al. |
| 8,748,585 B2 | 6/2014 | Attinger et al. |
| 8,784,815 B2 | 7/2014 | Korman et al. |
| 8,877,199 B2 | 11/2014 | Rader et al. |
| 8,906,367 B2 | 12/2014 | Nitsch et al. |
| 8,993,524 B2 | 3/2015 | Bedi et al. |
| 9,062,111 B2 | 6/2015 | Nichol et al. |
| 9,119,839 B2 | 9/2015 | Huang et al. |
| 9,273,135 B2 | 3/2016 | Korman et al. |

(Continued)

FOREIGN PATENT DOCUMENTS

| | | |
|---|---|---|
| CN | 104292334 A | 1/2015 |
| CN | 106620691 A | 5/2017 |

(Continued)

OTHER PUBLICATIONS

Notice of Examination for corresponding Taiwanese application No. 108139473; dated Dec. 21, 2023 (12 pages) Machine Translation.

(Continued)

*Primary Examiner* — Ilia I Ouspenski

(74) *Attorney, Agent, or Firm* — Mendelsohn Dunleavy PC; Kevin J. Dunleavy

(57) ABSTRACT

A polypeptide having a heavy chain variable region and/or light chain variable region that specifically binds to CTLA4 protein as well as antibodies and antibody fragments containing the heavy chain variable region and/or the light chain variable region that bind to CTLA4 protein. Pharmaceutical compositions and kits comprising the polypeptide or antibodies and antibody fragments containing the polypeptide are also provided.

18 Claims, 18 Drawing Sheets

Specification includes a Sequence Listing.

(56) References Cited

U.S. PATENT DOCUMENTS

| | | | |
|---|---|---|---|
| 9,487,581 B2 | 11/2016 | Abate et al. | |
| 9,573,999 B2 | 2/2017 | Nichol et al. | |
| 9,580,505 B2 | 2/2017 | Korman et al. | |
| 9,580,507 B2 | 2/2017 | Korman et al. | |
| 9,718,872 B2 | 8/2017 | Kyratsous et al. | |
| 9,718,881 B2 | 8/2017 | Gromada et al. | |
| 9,758,583 B2 | 9/2017 | Wang et al. | |
| 9,987,314 B2 | 6/2018 | Champion et al. | |
| 10,034,905 B2 | 7/2018 | Seymour et al. | |
| 11,149,088 B2 | 10/2021 | Short et al. | |
| 11,254,742 B2 | 2/2022 | Short et al. | |
| 11,542,332 B2 * | 1/2023 | Short | A61K 47/6849 |
| 2002/0086014 A1 | 7/2002 | Korman et al. | |
| 2003/0157132 A1 | 8/2003 | Itami et al. | |
| 2004/0006215 A1 | 1/2004 | Keler et al. | |
| 2004/0228858 A1 | 11/2004 | Hanson et al. | |
| 2004/0228861 A1 | 11/2004 | Hanson et al. | |
| 2005/0201994 A1 | 9/2005 | Korman et al. | |
| 2005/0287136 A1 | 12/2005 | Hanson et al. | |
| 2006/0177442 A1 | 8/2006 | Von Strandmann et al. | |
| 2008/0233122 A1 | 9/2008 | Hanson et al. | |
| 2008/0248047 A1 | 10/2008 | Das et al. | |
| 2008/0279865 A1 | 11/2008 | Gomez-Navarro | |
| 2009/0017039 A1 | 1/2009 | Mi et al. | |
| 2009/0055944 A1 | 2/2009 | Korman et al. | |
| 2009/0074787 A1 | 3/2009 | Gomez-Navarro et al. | |
| 2009/0104207 A1 | 4/2009 | Depla et al. | |
| 2009/0117132 A1 | 5/2009 | Readett et al. | |
| 2009/0130119 A1 | 5/2009 | Abate et al. | |
| 2009/0175886 A1 | 7/2009 | Black et al. | |
| 2009/0202562 A1 | 8/2009 | Worley et al. | |
| 2009/0252741 A1 | 10/2009 | Liu et al. | |
| 2009/0291081 A1 | 11/2009 | Hsieh et al. | |
| 2010/0021473 A1 | 1/2010 | De Angelis et al. | |
| 2010/0021479 A1 | 1/2010 | Cardarelli et al. | |
| 2010/0047244 A1 | 2/2010 | Korman et al. | |
| 2010/0055033 A1 | 3/2010 | Dimitrov et al. | |
| 2010/0056764 A1 | 3/2010 | Urso et al. | |
| 2010/0138945 A1 | 6/2010 | Frey et al. | |
| 2010/0291001 A1 | 11/2010 | Dransfield et al. | |
| 2010/0322920 A1 | 12/2010 | Keler et al. | |
| 2011/0027262 A1 | 2/2011 | Das et al. | |
| 2011/0081354 A1 | 4/2011 | Korman et al. | |
| 2011/0182809 A1 | 7/2011 | Nitsch et al. | |
| 2011/0209230 A1 | 8/2011 | Korman et al. | |
| 2011/0296546 A1 | 12/2011 | Korman et al. | |
| 2012/0006716 A1 | 1/2012 | Frey et al. | |
| 2012/0027686 A1 | 2/2012 | Sexton et al. | |
| 2012/0121504 A1 | 5/2012 | Rader et al. | |
| 2012/0213793 A1 | 8/2012 | Huang et al. | |
| 2012/0251533 A1 | 10/2012 | Cardarelli et al. | |
| 2012/0276086 A1 | 11/2012 | Black et al. | |
| 2013/0039911 A1 | 2/2013 | Bedi et al. | |
| 2013/0122014 A1 | 5/2013 | Korman et al. | |
| 2013/0136749 A1 | 5/2013 | Korman et al. | |
| 2013/0171146 A1 | 7/2013 | Hsieh et al. | |
| 2013/0183315 A1 | 7/2013 | Attinger et al. | |
| 2013/0209479 A1 | 8/2013 | Huang et al. | |
| 2013/0266514 A1 | 10/2013 | Nitsch et al. | |
| 2013/0266585 A1 | 10/2013 | Nitsch et al. | |
| 2013/0266586 A1 | 10/2013 | Nitsch et al. | |
| 2013/0287802 A1 | 10/2013 | Govindappa et al. | |
| 2014/0105914 A1 | 4/2014 | Jones et al. | |
| 2014/0213459 A1 | 7/2014 | Beckmann | |
| 2014/0234331 A1 | 8/2014 | Korman et al. | |
| 2014/0242077 A1 | 8/2014 | Choi et al. | |
| 2014/0294824 A1 | 10/2014 | Attinger et al. | |
| 2015/0037339 A1 | 2/2015 | Gromada et al. | |
| 2015/0079100 A1 | 3/2015 | Roy et al. | |
| 2015/0086575 A1 | 3/2015 | Rader et al. | |
| 2015/0203579 A1 | 7/2015 | Papadopoulos et al. | |
| 2015/0315267 A1 | 11/2015 | Bussiere et al. | |
| 2015/0337029 A1 | 11/2015 | Kyratsous et al. | |
| 2015/0337038 A1 | 11/2015 | Korman et al. | |
| 2016/0009807 A1 | 1/2016 | Govindappa et al. | |
| 2016/0024214 A1 | 1/2016 | Urso et al. | |
| 2016/0060343 A1 | 3/2016 | Huang et al. | |
| 2016/0075782 A1 | 3/2016 | Korman et al. | |
| 2016/0130341 A1 | 5/2016 | Johns | |
| 2016/0145355 A1 | 5/2016 | Saha et al. | |
| 2016/0177390 A1 | 6/2016 | Feng et al. | |
| 2016/0185875 A1 | 6/2016 | Cheng et al. | |
| 2016/0215040 A1 | 7/2016 | Kyratsous et al. | |
| 2016/0237154 A1 | 8/2016 | Gray et al. | |
| 2016/0237155 A1 | 8/2016 | Govindappa et al. | |
| 2016/0257753 A1 | 9/2016 | Korman et al. | |
| 2016/0289310 A1 | 10/2016 | Nitsch et al. | |
| 2016/0289341 A1 | 10/2016 | Wu | |
| 2016/0289343 A1 | 10/2016 | Wu | |
| 2016/0331793 A1 | 11/2016 | Champion et al. | |
| 2016/0362495 A1 | 12/2016 | Korman et al. | |
| 2017/0015739 A1 | 1/2017 | Kallunki et al. | |
| 2017/0035818 A1 | 2/2017 | Seymour et al. | |
| 2017/0037124 A1 | 2/2017 | Gusarova et al. | |
| 2017/0037131 A1 | 2/2017 | Bernett et al. | |
| 2017/0065650 A1 | 3/2017 | Engeland et al. | |
| 2017/0145104 A1 | 5/2017 | Wang et al. | |
| 2017/0158767 A1 | 6/2017 | Korman et al. | |
| 2017/0210808 A1 | 7/2017 | Rosenthal et al. | |
| 2017/0218069 A1 | 8/2017 | Rosengren et al. | |
| 2017/0233747 A1 | 8/2017 | Govindappa et al. | |
| 2017/0275362 A1 | 9/2017 | Brentjens et al. | |
| 2017/0313990 A1 | 11/2017 | Champion et al. | |
| 2018/0022807 A1 | 1/2018 | Kasturirangan | |
| 2018/0044419 A9 | 2/2018 | Rosengren et al. | |
| 2018/0118836 A1 | 5/2018 | Bernett et al. | |
| 2018/0125988 A1 | 5/2018 | Yang et al. | |
| 2018/0127501 A1 | 5/2018 | Bernett et al. | |
| 2018/0134773 A1 | 5/2018 | Nitsch et al. | |
| 2018/0147271 A1 | 5/2018 | Morgan et al. | |
| 2018/0186863 A1 | 7/2018 | Frey et al. | |
| 2018/0222990 A1 | 8/2018 | Hoos et al. | |
| 2018/0311291 A1 | 11/2018 | Champion et al. | |
| 2018/0369374 A1 | 12/2018 | Frederick et al. | |
| 2021/0017283 A1 | 1/2021 | Johnston et al. | |
| 2021/0047410 A1 | 2/2021 | Liu et al. | |

FOREIGN PATENT DOCUMENTS

| | | | |
|---|---|---|---|
| CN | 108271359 A | 7/2018 | |
| EP | 2620450 A2 | 7/2013 | |
| EP | 2227296 B1 | 11/2015 | |
| EP | 2542590 B1 | 5/2017 | |
| JP | 2017-532019 A | 11/2017 | |
| WO | 014424 A1 | 3/2001 | |
| WO | 2006039644 A2 | 4/2006 | |
| WO | 2006048749 A1 | 5/2006 | |
| WO | 2006089232 A2 | 8/2006 | |
| WO | 2006096491 A2 | 9/2006 | |
| WO | 2006101691 A1 | 9/2006 | |
| WO | 2006101692 A1 | 9/2006 | |
| WO | 2007008463 A2 | 1/2007 | |
| WO | 2007084672 A2 | 7/2007 | |
| WO | 2007113648 A2 | 10/2007 | |
| WO | 2007118214 A2 | 10/2007 | |
| WO | 2009077483 A1 | 6/2009 | |
| WO | 2009100140 A1 | 8/2009 | |
| WO | 2009131702 A2 | 10/2009 | |
| WO | 2010014784 A2 | 2/2010 | |
| WO | 2010132532 A1 | 11/2010 | |
| WO | 2011045704 A1 | 4/2011 | |
| WO | 2011109789 A2 | 9/2011 | |
| WO | 2012033953 A1 | 3/2012 | |
| WO | 2012120125 A1 | 9/2012 | |
| WO | 2012163519 A1 | 12/2012 | |
| WO | 2013008171 A1 | 1/2013 | |
| WO | 2013165972 A2 | 11/2013 | |
| WO | 2014028354 A1 | 2/2014 | |
| WO | 2014168759 A1 | 10/2014 | |
| WO | 2014204941 A1 | 12/2014 | |
| WO | 2014209804 A1 | 12/2014 | |
| WO | 2015017576 A1 | 2/2015 | |
| WO | 2015058048 A1 | 4/2015 | |
| WO | 2015103072 A1 | 7/2015 | |

(56)                References Cited

FOREIGN PATENT DOCUMENTS

| WO | 2015128313 A1 | 9/2015 |
| WO | 2015187835 A2 | 12/2015 |
| WO | 2016022021 A1 | 2/2016 |
| WO | 2016033555 A1 | 3/2016 |
| WO | 2016036916 A1 | 3/2016 |
| WO | 2016059602 A2 | 4/2016 |
| WO | 2016123019 A1 | 8/2016 |
| WO | 2016141387 A1 | 9/2016 |
| WO | 2016164637 A1 | 10/2016 |
| WO | 2016187216 A1 | 11/2016 |
| WO | 2016189124 A1 | 12/2016 |
| WO | 2016196237 A1 | 12/2016 |
| WO | 2017009312 A1 | 1/2017 |
| WO | 2017015634 A2 | 1/2017 |
| WO | 2017027316 A1 | 2/2017 |
| WO | 2017087678 A2 | 5/2017 |
| WO | 2017106061 A1 | 6/2017 |
| WO | 2017120612 A1 | 7/2017 |
| WO | 2017186928 A1 | 11/2017 |
| WO | 2017189959 A1 | 11/2017 |
| WO | 2017189964 A2 | 11/2017 |
| WO | 2017193032 A2 | 11/2017 |
| WO | 2017197231 A1 | 11/2017 |
| WO | 2018045018 A1 | 3/2018 |
| WO | 2018218076 A1 | 11/2018 |
| WO | 2019152423 A1 | 8/2019 |

OTHER PUBLICATIONS

Office action for corresponding Mexican application No. MX/a/2021/005048; dated May 2, 2025 (18 pages). Machine Translation.

Office action for corresponding Taiwanese patent application No. 113144596, dated Mar. 10, 2025 (8 pages). Machine Translation.

Office Action for corresponding Canadian application No. 3,117,700; dated Jun. 2, 2023 (3 pages).

Examination report based on corresponding Australian application No. 2022204161; dated Dec. 10, 2024 (5 pages).

Patent Examination Report 1 for corresponding New Zealand application No. 775959; dated Oct. 28, 2021 (5 pages).

Examination Report No. 1 for corresponding Australian application No. 2019371223; dated Nov. 2, 2021 (8 pages).

Patent Examination Report 2 for corresponding New Zealand application No. 775959; dated May 6, 2022 (3 pages).

Office Action for corresponding Canadian application No. 3,117,700; dated May 12, 2022 (4 pages).

Request for Submission of Opinion for corresponding Korean application No. 10-2021-7013727; dated Aug. 2, 2022 (9 pages) Machine Translation.

Rowshanravan, Behzad, et al. "CTLA-4: a moving target in immunotherapy." Blood, The Journal of the American Society of Hematology 131.1 (2018): 58-67.

Office Action for corresponding Chinese application No. 2019800724964; dated Sep. 5, 2024 (5 pages) Machine Translation.

Office Action for corresponding Canadian application No. 3,117,700; dated Dec. 5, 2022 (4 pages).

Rudikoff, Stuart, et al. "Single amino acid substitution altering antigen-binding specificity." Proceedings of the National Academy of Sciences 79.6 (1982): 1979-1983.

Tamura, Midori, et al. "Structural Correlates of an Anticarcinoma Antibody: Identification of Specificity-Determining Residues (SDRs) and Development of a Minimally Immunogenic Antibody Variant by Retention of SDRs Only." The Journal of Immunology 164.3 (2000): 1432-1441.

Second Office Action for corresponding Chinese application No. 201980072496.4; dated Mar. 24, 2024 (13 pages).

International Search Report and Written Opinion for corresponding International application No. PCT/US2019/058066; dated Feb. 7, 2020 (13 pages).

"Ipilimumab." Drugs in R&D 10.2 (2010): 97-110. https://doi.org/10.2165/11584510-000000000-00000.

Allison, James P. "CD28-B7 interactions in T-cell activation." Current Opinion in Immunology 6.3 (1994): 414-419.

Brunet, Jean-Francois, et al. "A new member of the immunoglobulin superfamily-CTLA-4." Nature 328.6127 (1987): 267-270.

Brunet, Jean-Francois, et al. "A Differential Molecular Biology Search for Genes Preferentially Expressed in Functional T Lymphocytes: The CTLA Genes." Immunological Reviews 103 (1988): 21-36.

Chambers, Cynthia A., et al. "Lymphoproliferation in CTLA-4-Deficient Mice Is Mediated by Costimulation-Dependent Activation of CD4+ T Cells." Immunity 7.6 (1997): 885-895.

Chambers, Cynthia A., et al. "Co-stimulation in T cell responses." Current Opinion in Immunology 9.3 (1997): 396-404.

Dariavach, Piona, et al. "Human Ig superfamily CTLA-4 gene: chromosomal localization and identity of protein sequence between murine and human CTLA-4 cytoplasmic domains." European Journal of Immunology 18.12 (1988): 1901-1905.

Dinarello, Charles A., et al. "Lymphokines." New England Journal of Medicine 317.15 (1987): 940-945.

Eggermont, Alexander M. M., et al. "Prolonged Survival in Stage III Melanoma with Ipilimumab Adjuvant Therapy." New England Journal of Medicine 375.19 (2016): 1845-1855.

Grosso, Joseph F., et al. "CTLA-4 blockade in tumor models: an overview of preclinical and translational research." Cancer Immunity 13.1 (2013): 5-18.

He, Mengnan, et al. "Remarkably similar CTLA-4 binding properties of therapeutic ipilimumab and tremelimumab antibodies." Oncotarget 8.40 (2017): 67129-67139.

Hemler, Martin E. "Adhesive protein receptors on hematopoietic cells." Immunology Today 9.4 (1988): 109-113.

Janeway, Charles A. "Approaching the Asymptote? Evolution and Revolution in Immunology." Cold Spring Harbor Symposia on Quantitative Biology. vol. 54. Cold Spring Harbor Laboratory Press, (1989) 1-13.

Krummel, Matthew F., et al. "CD28 and CTLA-4 Have Opposing Effects on the Response of T cells to Stimulation." The Journal of Experimental Medicine 182.2 (1995): 459-465.

Krummel, Matthew F., et al. "Superantigen responses and co-stimulation: CD28 and CTLA-4 have opposing effects on T cell expansion in vitro and in vivo." International Immunology 8.4 (1996): 519-523.

Lafage-Pochitaloff, Marina, et al. "Human CD28 and CTLA-4 Ig superfamily genes are located on chromosome 2 at bands q33-q34." Immunogenetics 31.3 (1990): 198-201.

Leach, Dana R., et al. "Enhancement of Antitumor Immunity by CTLA-4 Blockade." Science 271.5256 (1996): 1734-1736.

Linsley, Peter S., et al. "Coexpression and Functional Cooperation of CTLA-4 and CD28 on Activated T Lymphocytes." The Journal of Experimental Medicine 176.6 (1992): 1595-1604.

Lühder, Fred, et al. "Cytotoxic T Lymphocyte-associated Antigen 4 (CTLA-4) Regulates the Unfolding of Autoimmune Diabetes." The Journal of Experimental Medicine 187.3 (1998): 427-432.

Matsui, Toshihiro, et al. "Autoantibodies to T Cell Costimulatory Molecules in Systemic Autoimmune Diseases." The Journal of Immunology 162.7 (1999): 4328-4335.

Ramagopal, Udupi A., et al. "Structural basis for cancer immunotherapy by the first-in-class checkpoint inhibitor pilimumab." Proceedings of the National Academy of Sciences 114.21 (2017): E4223-E4232.

Sallusto, Federica, et al. "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor alpha." The Journal of Experimental Medicine 179.4 (1994): 1109-1118.

Shaw, S., et al. "Two molecular pathways of human T cell adhesion: establishment of receptor-ligand relationship." Current Opinion in Immunology 1.1, Eds. Kindt and Long (1988): 92-97.

Springer, Timothy A., et al. "The lymphocyte function associated LFA-1, CD2, and LFA-3 molecules: cell adhesion receptors of the immune system." Annual Review of Immunology 5.1 (1987): 223-252.

Thompson, Craig B., et al. "The Emerging Role of CTLA-4 as an Immune Attenuator." Immunity 7.4 (1997): 445-450.

(56) References Cited

OTHER PUBLICATIONS

Walunas, Theresa L., et al. "CTLA-4 Can Function as a Negative Regulator of T Cell Activation." Immunity 1.5 (1994): 405-413.

Wang, Manni et al. "Immune checkpoint blockade and its combination therapy with small-molecule inhibitors for cancer treatment." BBACAN 88261 (2018): 1-74 https://doi.org/10.1016/j.bbcan.2018.12.002.

Weiss, Arthur, et al. "The role of the T3/antigen receptor complex in T-cell activation." Annual Review of Immunology 4 (1986): 593-619.

Wu, Yan, et al. "CTLA-4-B7 Interaction Is Sufficient to Costimulate T Cell Clonal Expansion." The Journal of Experimental Medicine 185.7 (1997): 1327-1335.

Zahavi, David J., et al. "Targeting Multiple Receptors to Increase Checkpoint Blockade Efficacy." International Journal of Molecular Sciences 20.158 (2019): 1-11.

Notice of Reasons for Rejection for corresponding Japanese application No. 2021-547665; dated Sep. 19, 2023 (8 pages) Machine Translation.

First Office Action for corresponding Chinese application No. 201980072496.4; dated Aug. 19, 2023 (14 pages).

Office Action for corresponding Eurasian patent application No. 202191187; dated Aug. 23, 2023 (6 pages).

Examination Report No. 1 for corresponding Australian application No. 2022204161; dated Jul. 28, 2024 (4 pages).

Office Action for corresponding Israeli application No. 291545; dated Aug. 8, 2024 (4 pages).

Office action for corresponding Mexican application No. MX/a/2021/005048; dated Aug. 26, 2025 (24 pages). Machine Translation.

Office action for corresponding Korean application No. 10-2023-7011890; dated Oct. 21, 2025 (15 pages). Machine Translation.

* cited by examiner

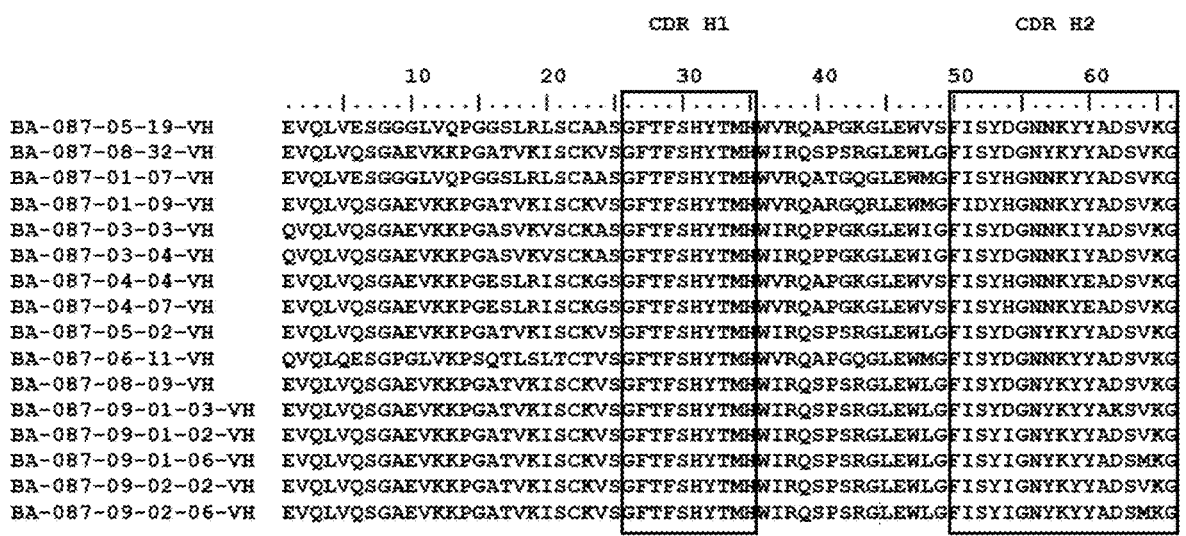
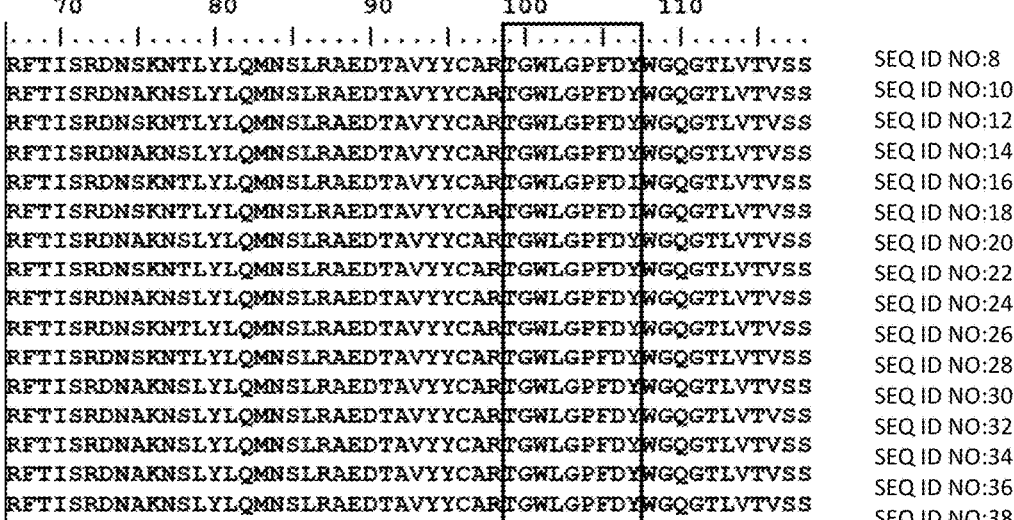
Fig. 1

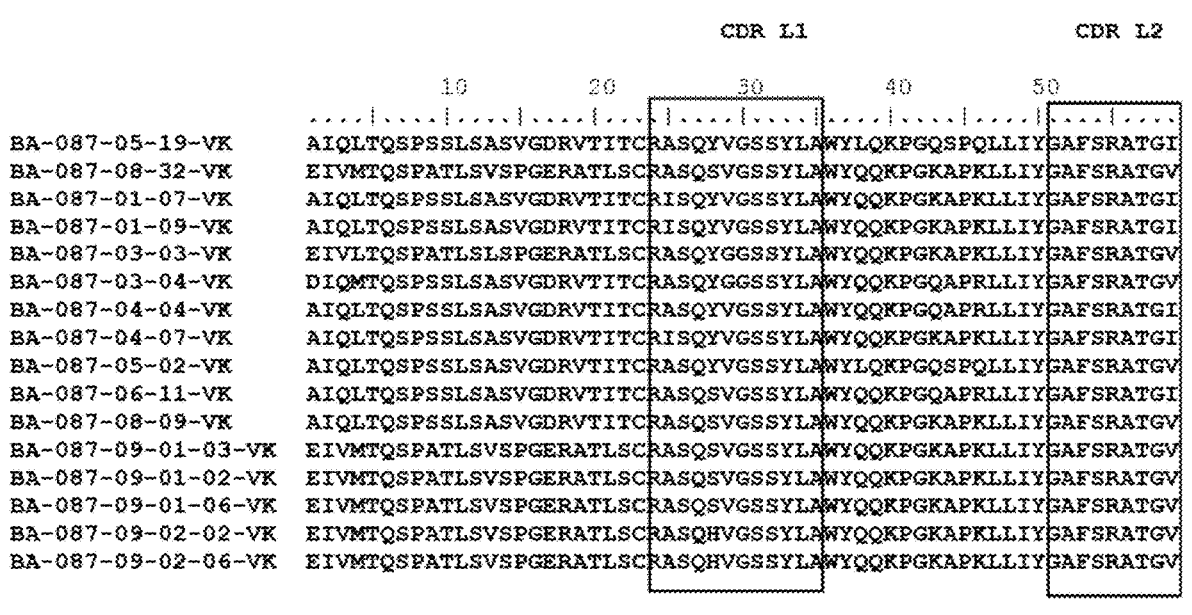

```
                                                        CDR L1                          CDR L2
                        10        20        30        40        50
                        ....|....|....|....|....|....|....|....|....|....|....|....
BA-087-05-19-VK    AIQLTQSPSSLSASVGDRVTITCRASQYVGSSYLAWYLQKPGQSPQLLIYGAFSRATGI
BA-087-08-32-VK    EIVMTQSPATLSVSPGERATLSCRASQSVGSSYLAWYQQKPGKAPKLLIYGAFSRATGV
BA-087-01-07-VK    AIQLTQSPSSLSASVGDRVTITCRISQYVGSSYLAWYQQKPGKAPKLLIYGAFSRATGI
BA-087-01-09-VK    AIQLTQSPSSLSASVGDRVTITCRISQYVGSSYLAWYQQKPGKAPKLLIYGAFSRATGI
BA-087-03-03-VK    EIVLTQSPATLSLSPGERATLSCRASQYGGSSYLAWYQQKPGKAPKLLIYGAFSRATGV
BA-087-03-04-VK    DIQMTQSPSSLSASVGDRVTITCRASQYGGSSYLAWYQQKPGQAPRLLIYGAFSRATGV
BA-087-04-04-VK    AIQLTQSPSSLSASVGDRVTITCRASQYVGSSYLAWYQQKPGQAPRLLIYGAFSRATGI
BA-087-04-07-VK    AIQLTQSPSSLSASVGDRVTITCRISQYVGSSYLAWYQQKPGKAPKLLIYGAFSRATGI
BA-087-05-02-VK    AIQLTQSPSSLSASVGDRVTITCRASQYVGSSYLAWYLQKPGQSPQLLIYGAFSRATGV
BA-087-06-11-VK    AIQLTQSPSSLSASVGDRVTITCRASQSVGSSYLAWYQQKPGQAPRLLIYGAFSRATGI
BA-087-08-09-VK    AIQLTQSPSSLSASVGDRVTITCRASQSVGSSYLAWYQQKPGKAPKLLIYGAFSRATGV
BA-087-09-01-03-VK EIVMTQSPATLSVSPGERATLSCRASQSVGSSYLAWYQQKPGKAPKLLIYGAFSRATGV
BA-087-09-01-02-VK EIVMTQSPATLSVSPGERATLSCRASQSVGSSYLAWYQQKPGKAPKLLIYGAFSRATGV
BA-087-09-01-06-VK EIVMTQSPATLSVSPGERATLSCRASQSVGSSYLAWYQQKPGKAPKLLIYGAFSRATGV
BA-087-09-02-02-VK EIVMTQSPATLSVSPGERATLSCRASQHVGSSYLAWYQQKPGKAPKLLIYGAFSRATGV
BA-087-09-02-06-VK EIVMTQSPATLSVSPGERATLSCRASQHVGSSYLAWYQQKPGKAPKLLIYGAFSRATGV
```

```
                                             CDR L3

60        70        80        90        100
|....|....|....|....|....|....|....|....|....|....|...
PARFSGSGSGTEFTLTISSLSEDFAVYYCQQDGSSPWTFGQGTKVEIK    SEQ ID NO:7
PSRFSGSGSGTDFTLTISSLQPEDFATYYCQQDGSSPWTFGQGTKVEIK    SEQ ID NO:9
PDRFSGSGSGTDFTLTISRLEPEDFAVYYCQQDGSSPWTFGQGTKVEIK    SEQ ID NO:11
PDRFSGSGSGTDFTLTISRLEPEDFAVYYCQQDGSSPWTFGQGTKVEIK    SEQ ID NO:13
PSRFSGSGSGTDFTFTISSLQPEDIATYYCQQDGSSPWTFGQGTKVEIK    SEQ ID NO:15
PSRFSGSGSGTDFTFTISSLQPEDIATYYCQQDGSSPWTFGQGTKVEIK    SEQ ID NO:17
PARFSGSGSGTEFTLTISSLSEDFAVYYCQQDGSSPWTFGQGTKVEIK    SEQ ID NO:19
PDRFSGSGSGTDFTLTISRLEPEDFAVYYCQQDGSSPWTFGQGTKVEIK    SEQ ID NO:21
PSRFSGSGSGTEFTLTISSLQPDDFATYYCQQDGSSPWTFGQGTKVEIK    SEQ ID NO:23
PARFSGSGSGTEFTLTISSLSEDFAVYYCQQDGSSPWTFGQGTKVEIK    SEQ ID NO:25
PSRFSGSGSGTEFTLTISSLQPDDFATYYCQQDGSSPWTFGQGTKVEIK    SEQ ID NO:27
PSRFSGSGSGTDFTLTISSLQPEDFATYYCQQDGSSPWTFGQGTKVEIK    SEQ ID NO:29
PSRFSGSGSGTDFTLTISSLQPEDFATYYCQQDGSSPWTFGQGTKVEIK    SEQ ID NO:31
PSRFSGSGSGTDFTLTISSLQPEDFATYYCQQDGSSPWTFGQGTKVEIK    SEQ ID NO:33
PSRFSGSGSGTDFTLTISSLQPEDFATYYCQQDGSSPWTFGQGTKVEIK    SEQ ID NO:35
PSRFSGSGSGTDFTLTISSLQPEDFATYYCQQDGSSPWTFGQGTKVEIK    SEQ ID NO:37
```

FIG. 2

| | Ipilimumab | Ipi Analog | BA-087-05-19 | BA-087-08-32 |
|---|---|---|---|---|
| EC50 | 189.8 | 161.4 | 242.3 | 353.9 |

| | Ipilimumab | Ipi Analog | BA-087-05-19 | BA-087-08-32 |
|---|---|---|---|---|
| EC50 | 177.1 | 184.9 | 8275 | 83913 |

| | 6972 Glu T2W pH6.0 | 6972 Glu T0 pH6.0 | 6972 ctrl pH6.0 | 6972 Glu T2W pH7.4 | 6972 Glu T0 pH7.4 | 6972 ctrl pH7.4 |
|---|---|---|---|---|---|---|
| EC50 | 366.6 | 291 | 222.5 | 606.9 | 461.5 | 428.1 |

| | 6978 His T2W pH6.0 | 6978 His T0 pH6.0 | 6978 ctrl pH6.0 | 6978 His T2W pH7.4 | 6978 His T0 pH7.4 | 6978 ctrl pH7.4 |
|---|---|---|---|---|---|---|
| EC50 | 144.8 | 159 | 158.4 | 1179 | 848.5 | 967.5 |

BA-087 CTLA4 pH6.0

|  | Ipilimumab | Ipi Analog | BA-087-05-19 | BA-087-08-32 | IgG control |
|---|---|---|---|---|---|
| EC50 | 0.5811 | 0.6523 | 1.195 | ~ 16504533325657 | ~ 91.71 |

BA-087-CTLA4 pH7.4

|  | Ipilimumab | Ipi Analog | BA-087-05-19 | BA-087-08-32 | IgG control |
|---|---|---|---|---|---|
| EC50 | 0.6488 | 0.9095 | ~ 1.258e+025 | 0.2449 | ~ 258563 |

| | Ipi Analog | Ipilimumab | BA-087-05-19 | BA-087-08-32 | IgG control |
|---|---|---|---|---|---|
| EC50 | 3094 | 3957 | ~ 197808 | 2724 | ~ 29129 |

| | Ipi Analog | Ipilimumab | BA-087-05-19 | BA-087-08-32 | IgG control |
|---|---|---|---|---|---|
| EC50 | ~ 2454034 | 7189 | 3729 | 3869 | ~ 228919 |

ANTI-CTLA4 ANTIBODIES, ANTIBODY FRAGMENTS, THEIR IMMUNOCONJUGATES AND USES THEREOF

CROSS REFERENCE TO RELATED APPLICATIONS

This application is a continuation of U.S. patent application Ser. No. 17/288,187, filed on Mar. 25, 2022, which, in turn, is a 371 continuation of PCT/US2019/058066, filed on Oct. 25, 2019, which, in turn, claims the benefit of U.S. provisional application No. 62/824,014, filed on Mar. 26, 2019; U.S. provisional application No. 62/823,992, filed on Mar. 26, 2019; U.S. provisional application No. 62/822,971, filed on Mar. 24, 2019; U.S. provisional application No. 62/803,060, filed on Feb. 8, 2019; U.S. provisional application No. 62/798,234, filed on Jan. 29, 2019; and U.S. provisional application No. 62/753,498, filed on Oct. 31, 2018; the disclosures of which applications are all hereby incorporated by reference herein in their entirety.

INCORPORATION OF MATERIAL OF XML SEQUENCE LISTING BY REFERENCE

The sequence listing submitted herewith as an XML file named "BIAT-1028USCONSequenceListingXML" created on Nov. 29, 2022, which is 80,000 bytes in size, is hereby incorporated by reference herein in its entirety.

FIELD OF THE DISCLOSURE

This disclosure relates anti-CTLA4 antibodies, antibody fragments and immunoconjugates of such antibodies and antibody fragments and uses of the antibodies, antibody fragments and immunoconjugates in diagnostic and therapeutic methods.

BACKGROUND OF THE DISCLOSURE

The vertebrate immune system requires multiple signals to achieve an optimal immune activation; see, e.g., Janeway, *Cold Spring Harbor Symp. Ouant. Biol.* 54:1-14 (1989); Paul William E., ed. Raven Press, N.Y., *Fundamental Immunology*, 4th edition (1998), particularly chapters 12 and 13, pages 411 to 478. Interactions between T lymphocytes (T cells) and antigen presenting cells (APC) are essential to immune activation. Levels of many cohesive molecules found on T cells and APCs increase during immune activation (Springer et al., A. *Rev. Immunol.*, 5:223-252 (1987); Shaw and Shimuzu, *Current Opinion in Immunology*, Eds. Kindt and Long. 1:92-97 (1988)); and Hemler, *Immunology Today*, 9:109-113 (1988)). Increased levels of these molecules may help explain why activated APCs are more effective at stimulating antigen-specific T cell proliferation than are resting APC's (Kaiuchi et al., *J. Immunol.*, 131: 109-114 (1983); Kreiger et al., *J. Immunol.*, 135:2937-2945 (1985); McKenzie, *J. Immunol.*, 141:2907-2911 (1988); and Hawrylowicz and Unanue, *J. Immunol.*, 141:4083-4088 (1988)).

T cell immune response is a complex process that involves cell-cell interactions (Springer et al., *A. Rev. Immunol.*, 5:223-252 (1987)), particularly between T cells and accessory cells such as APCs, as well as production of soluble immune mediators (cytokines or lymphokines) (Dinarello, *New Engl. Jour: Med.*, 317:940-945 (1987); Sallusto, *J. Exp. Med.*, 179:1109-1118 (1997)). The immune response is regulated by several T-cell surface receptors, including the T-cell receptor complex (Weiss, *Ann. Rev. Immunol.*, 4:593-619 (1986)) and other "accessory" surface molecules (Allison, *Curr. Opin. Immunol.*, 6:414-419 (1994); Springer (1987) supra). Many of these accessory molecules are naturally occurring cell surface differentiation antigens defined by the reactivity of monoclonal antibodies on the surface of cells (McMichael, Ed., *Leukocyte Tiping III*, Oxford Univ. Press, Oxford, N.Y. (1987)).

CTLA4 is a T cell surface molecule that was originally identified by differential screening of a murine cytolytic T cell cDNA library (Brunet et al., *Nature* 328:267-270 (1987)). CTLA4 is also a member of the immunoglobulin (Ig) Superfamily. CTLA4 comprises a single extracellular Ig domain. CTLA4 transcripts have been found in T cell populations having cytotoxic activity, suggesting that CTLA4 might function in the cytolytic response (Brunet et al., Supra; Brunet et al., *Immunol. Rev.*, 103:21-36 (1988)). Researchers have reported the cloning and mapping of a gene for the human counterpart of CTLA4 (Dariavach et al., *Eur: J. Immunol.*, 18:1901-1905 (1988)) to the same chromosomal region (2d, 33-34) as CD28 (Lafage-Pochitaloff et al., *Immunogenetics* 31:198-201 (1990)). Sequence comparison between this human CTLA4 DNA and that encoding CD28 proteins reveals significant homology of sequence, with the greatest degree of homology in the juxtamembrane and cytoplasmic regions (Brunet et al., 1988, Supra: Dariavach et al., 1988, Supra).

Some studies have suggested that CTLA4 has an analogous function as a secondary costimulator (Linsley et al., *J. Exp. Med.*, 176:1595-1604 (1992); Wu et al., *J. Exp. Med.*, 185:1327-1335 (1997) and U.S. Pat. Nos. 5,977,318; 5,968,510; 5,885,796; and 5,885.579). However, others have reported that CTLA4 has an opposing role as a dampener of T cell activation (Krummel, *J. Exp. Med.*, 182:459-465 (1995); Krummel et al., *Int'l Immunol.*, 8:519-523 (1996); Chambers et al., *Immunity*, 7:885-895 (1997)). It has been reported that CTLA4 deficient mice suffer from massive lymphoproliferation (Chambers et al., supra). It has also been reported that a CTLA4 blockade augments T cell responses in vitro (Walunas et al., *Immunity*, 1:405-413 (1994)) and in vivo (Kearney, *J. Immunol.*, 155:1032-1036 (1995)), exacerbates antitumor immunity (Leach, *Science*, 271:1734-1736 (1996)), and enhances an induced autoimmune disease (Luhder, *J Exp. Med.*, 187:427-432 (1998)). It has also been reported that CTLA4 has an alternative or additional impact on the initial character of the T cell immune response (Chambers, *Curr. Opin. Immunol.*, 9:396-404 (1997); Bluestone, *J. Immunol.*, 158:1989-1993 (1997); Thompson, *Immunity*, 7:445-450 (1997)). This is consistent with the observation that some autoimmune patients have autoantibodies to CTLA4. It is possible that CTLA4 blocking antibodies have a pathogenic role in these patients (Matsui, *J. Immunol.*, 162:4328-4335 (1999)).

CTLA4 has been shown to negatively regulate immune activation through both intrinsic and extrinsic mechanisms. See Grosso and Kunkel, *Cancer Immunity*, 13: 5 (2013). Specifically, (i) reverse signalling through CD80 and CD86 on APCs results in suppression of T cell responses and/or promotes conversion of naïve T cells to Tregs, (ii) signaling through CTLA3 stimulates production of regulatory cytokines such as TGF-β, resulting in inhibition of antigen presentation by APCs and inhibition of T cell function, (iii) binding of CTLA4 to CD80/CD86 reduces availability of these ligands for binding by CD28, resulting in reduced activation of T cells by APCs, (iv) binding of CTLA4 to CD80/CD86 causes their transendocytosis, reducing the ability for APCs to activate T cells, (v) CTLA4 recruits inhibitory proteins such as PP2A and PTPN11 to the T cell synapse, inhibiting signalling through CD28 and TCR, (vi) CTLA4 acts as a high affinity competitor occupying CD80/86 and thereby preventing binding by CD28, (vii) a soluble splice variant of CTLA4 may be capable of inhibiting T cell activation, and (viii) CTLA4 inhibits the T cell stop signal, which is important for activation of T cells by APCs.

Thus, inhibition of CTLA4 has been shown to promote stimulation of adaptive immune response and T cell activation. CTLA4-blocking antibodies have been shown to be efficacious in mouse models of cancer, and anti-CTLA4 antibodies such as ipilimumab (WO 2001/014424) and tremelimumab are being investigated as strategies to promote anti-tumor immunity in cancer. Blockade of CTLA4 is also a promising therapeutic strategy for disorders associated with T cell exhaustion such as chronic viral infection.

Antibodies to CTLA4 have been previously developed. U.S. Pat. No. 9,758,583 discloses antibodies or antibody fragments that are said to bind to one or both of human and murine CTLA4, which may be formulated into compositions for treatment of cancer. Some of the antibodies or antibody fragments are also said to optionally inhibit or prevent interaction or functional association between human CTLA4 and human CD80 or CD86, or between murine CTLA4 and murine CD80 or CD86. Such inhibition or prevention of interaction or functional association between CTLA4 and CD80 or CD86 may inhibit or prevent CD80 or CD86-mediated activation of CTLA4, CD80/CTLA4 signalling or CD86/CTLA4 signalling.

US 2009/0252741 also discloses monoclonal antibodies that bind to human CTLA4. These anti-CTLA4 antibodies are said to induce protection against cancer and also demonstrate some autoimmune side effects. The antibody that induced the strongest protection against cancer also induced the least autoimmune side effects. US 2009/0252741 also provides a method for selecting optimal anti-CTLA4 antibodies or other therapeutic agents with the most desirable balance between cancer protection and autoimmune side effects.

US 2016/0237154 discloses compositions and methods relating to or derived from anti-CTLA4 antibodies or antibody fragments. The anti-CTLA4 antibodies and antibody fragments may block binding of human CTLA4 to human B7, and thus are said to be suitable for treatment of cancers of the prostate, kidney, colon, lung or breast; pathogenic infections; diseases associated with the central nervous system, e.g. amyloidogenic diseases including Alzheimer's disease; and diseases with inflammatory or allergic components such as graft versus host disease, host versus graft disease, allergies, autoimmune diseases and other inflammatory diseases.

Though antibodies against CTLA4 are known and commercially available, it is desirable to find improved anti-CTLA4 antibodies that are suitable for cancer therapy with reduced or minimal side effects. The present invention provides anti-CTLA4 antibodies or antibody fragments that are suitable for therapeutic and diagnostic use, especially for diagnosis and treatment of cancers. Some of these anti-CTLA4 antibodies or antibody fragments may have a higher binding affinity to CTLA4 in a tumor in comparison with CTLA4 present in normal tissue. These anti-CTLA4 antibodies or antibody fragments typically have at least comparable efficacy to known anti-CTLA4 antibodies or antibody fragments. In addition, the present anti-CTLA4 antibodies or antibody fragments may exhibit reduced side effects in comparison with monoclonal anti-CTLA4 antibodies known in the art. These advantages may provide a more selective treatment of the CTLA4 in a tumor and may permit use of higher dosages of these anti-CTLA4 antibodies or antibody fragments as a result of the selectivity for CTLA4 in a tumor, whereby more effective therapeutic treatments can be realized without a corresponding increase in undesirable side effects.

SUMMARY OF THE DISCLOSURE

In one aspect, the present invention provides isolated heavy chain variable region polypeptides that specifically bind to the CTLA4 protein. These polypeptides include three complementarity determining regions having the H1, H2, and H3 sequences, wherein:

```
                                             (SEQ ID NO: 1)
    the H1 sequence is GFTFSHYTMH;

(SEQ ID NO: 2)
    the H2 sequence is FIX₁YX₂GNX₃KX₄X₅AX₆SX₇KG;
    and (SEQ ID NO: 3)
    the H3 sequence is TGWLGPFDX₈;
``` wherein $X_1$ is S or D; $X_2$ is D, H or I, $X_3$ is N or Y; $X_4$ is Y or I; $X_5$ is Y or E; $X_6$ is D or K; $X_7$ is V or M; and $X_8$ is Y or I.

In another aspect, the present invention includes a product formed by a combination of any of the above-described isolated heavy chain variable region polypeptides with an isolated light chain variable region polypeptide selected from isolated light chain variable region polypeptides that include three complementarity determining regions having the L1, L2, and L3 sequences, wherein:

```
                                             (SEQ ID NO: 4)
      the L1 sequence is RX₉SQX₁₀X₁₁GSSYLA;

(SEQ ID NO: 5)
      the L2 sequence is GAFSRATGX₁₂;
      and (SEQ ID NO: 6)
      the L3 sequence is QQDGSSPWT,
``` wherein $X_9$ is A or I; $X_{10}$ is Y, S or H; $X_{11}$ is V or G; $X_{12}$ is V or I.

In each of the previous embodiments, the H2 sequence may be selected from

```
                                             (SEQ ID NO: 45)
        FIDYHGNNKYYADSVKG, (SEQ ID NO: 46)
        FISYDGNNKIYADSVKG, (SEQ ID NO: 40)
        FISYDGNNKYYADSVKG, (SEQ ID NO: 47)
        FISYDGNYKYYADSVKG, (SEQ ID NO: 48)
        FISYDGNYKYYAKSVKG, (SEQ ID NO: 49)
        FISYHGNNKYEADSVKG,
```

5

-continued

```
                                     (SEQ ID NO: 50)
FISYHGNNKYYADSVKG, (SEQ ID NO: 51)
FISYIGNYKYYADSMKG,
and (SEQ ID NO: 52)
FISYIGNYKYYADSVKG.
```

In each of the previous embodiments, the H3 sequence may be selected from TGWLGPFDY (SEQ ID NO: 41) and TGWLGPFDI (SEQ ID NO: 53).

In each of the previous embodiments, the L1 sequence may be selected from

```
                                     (SEQ ID NO: 54)
    RASQHVGSSYLA, (SEQ ID NO: 55)
    RASQSVGSSYLA, (SEQ ID NO: 56)
    RASQYGGSSYLA, (SEQ ID NO: 42)
    RASQYVGSSYLA,
    and (SEQ ID NO: 57)
    RISQYVGSSYLA.
```

In each of the previous embodiments, the L2 sequence may be selected from GAFSRATGI (SEQ ID NO: 43) and GAFSRATGV (SEQ ID NO: 58).

In some embodiments, the isolated heavy chain variable region polypeptide may have a sequence selected from SEQ ID NOS: 8, 10, 12, 14, 16, 18, 20, 22, 24, 26, 28, 30, 32, 34, 36, and 38. In each of these embodiments, the isolated light chain variable region polypeptide may have a sequence selected from SEQ ID NOS: 7, 9, 11, 13, 15, 17, 19, 21, 23, 25, 27, 29, 31, 33, 35, and 37.

In one embodiment, the antibody comprises a light chain variable region polypeptide and a heavy chain variable region polypeptide having a pair of sequences selected from the pairs: SEQ ID NOS: 7 and 8, SEQ ID NOS: 9 and 10, SEQ ID NOS: 11 and 12, SEQ ID NOS: 13 and 14, SEQ ID NOS: 15 and 16, SEQ ID NOS: 17 and 18, SEQ ID NOS: 19 and 20, SEQ ID NOS: 21 and 22, SEQ ID NOS: 23 and 24, SEQ ID NOS: 25 and 26, SEQ ID NOS: 27 and 28, SEQ ID NOS: 29 and 30, SEQ ID NOS: 31 and 32, SEQ ID NOS: 33 and 34, SEQ ID NOS: 35 and 36 and SEQ ID NOS: 37 ad 38.

In yet another aspect, the present invention provides an anti-CTLA4 antibody or antibody fragment that includes any of the isolated heavy chain variable region polypeptides of the invention described above.

In yet another aspect, the present invention provides an anti-CTLA4 antibody or antibody fragment that includes a combination of any of the isolated heavy chain variable region polypeptides of the invention described above with any one of the isolated light chain variable region polypeptides of the invention described above.

In yet another aspect, the present invention provides an immunoconjugate that includes any of the antibody or antibody fragments of the invention described above. In the immunoconjugate, the antibody or antibody fragment may be conjugated to an agent selected from a chemotherapeutic agent, a radioactive atom, a cytostatic agent and a cytotoxic agent.

In yet another aspect, the present invention provides a pharmaceutical composition that includes any of the polypeptides, the antibodies, the antibody fragments, and the immunoconjugates of the invention described above, together with a pharmaceutically acceptable carrier. A single dose of the pharmaceutical composition may include an amount of the polypeptide, the antibody, the antibody fragment, or the immunoconjugate of about 135 mg, about 235 mg, about 335 mg, about 435 mg, about 535 mg, about 635 mg, about 735 mg, about 835 mg, about 935 mg, about 1035 mg, about 1135 mg, about 1235 mg, or about 1387 mg.

A single dose of the pharmaceutical composition of may include an amount of the polypeptide, the antibody, the antibody fragment, or the immunoconjugate in a range of 135-1387 mg, 135-235 mg, 235-335 mg, 335-435 mg, 435-535 mg, 535-635 mg, 635-735 mg, 735-835 mg, 835-935 mg, 935-1035 mg, 1035-1135 mg, 1135-1235 mg, or 1235-1387 mg.

Each of the foregoing pharmaceutical compositions may further include an immune checkpoint inhibitor molecule that is different from the polypeptide or the antibody or antibody fragment. The immune checkpoint inhibitor molecule may be an antibody or antibody fragment against an immune checkpoint. The immune checkpoint may be selected from LAG3, TIM3, TIGIT, VISTA, BTLA, OX40, CD40, 4-1BB, PD-1, PD-L1, GITR, B7-H3, B7-H4, KIR, A2aR, CD27, CD70, DR3, and ICOS or the immune checkpoint may be PD-1 or PD-L1.

Each of the foregoing pharmaceutical compositions may further include an antibody or antibody fragment against an antigen selected from PD1, PD-L1, AXL, ROR2, CD3, HER2, B7-H3, ROR1, SFRP4 and a WNT protein. The WNT protein may be selected from WNT1, WNT2, WNT2B, WNT3, WNT4, WNT5A, WNT5B, WNT6, WNT7A, WNT7B, WNT8A, WNT8B, WNT9A, WNT9B, WNT10A, WNT10B, WNT11 and WNT16.

In yet another aspect, the present invention provides a kit for diagnosis or treatment including any of the polypeptides, the antibodies, the antibody fragments, or the immunoconjugates of the present invention described above.

In yet another aspect, the present invention provides an anti-CTLA4 antibody comprising a heavy chain variable region and a light chain variable region, wherein the heavy chain variable region comprises three complementarity determining regions having amino acid sequences of SEQ ID NOS:39-41 and the light chain variable region comprises three complementarity determining regions having amino acid sequences of SEQ ID NOS:42-44.

In the previous embodiment, the heavy chain variable region may have an amino acid sequence of SEQ ID NO:8 and the light chain variable region may have an amino acid sequence of SEQ ID NO:7.

BRIEF DESCRIPTION OF THE DRAWINGS

FIG. 1 shows sequence alignments of exemplary heavy chain variable regions of anti-CTLA4 antibodies of the present invention.

FIG. 2 shows sequence alignments of exemplary light chain variable regions of anti-CTLA4 antibodies of the present invention.

DEFINITIONS

Figure 3A:
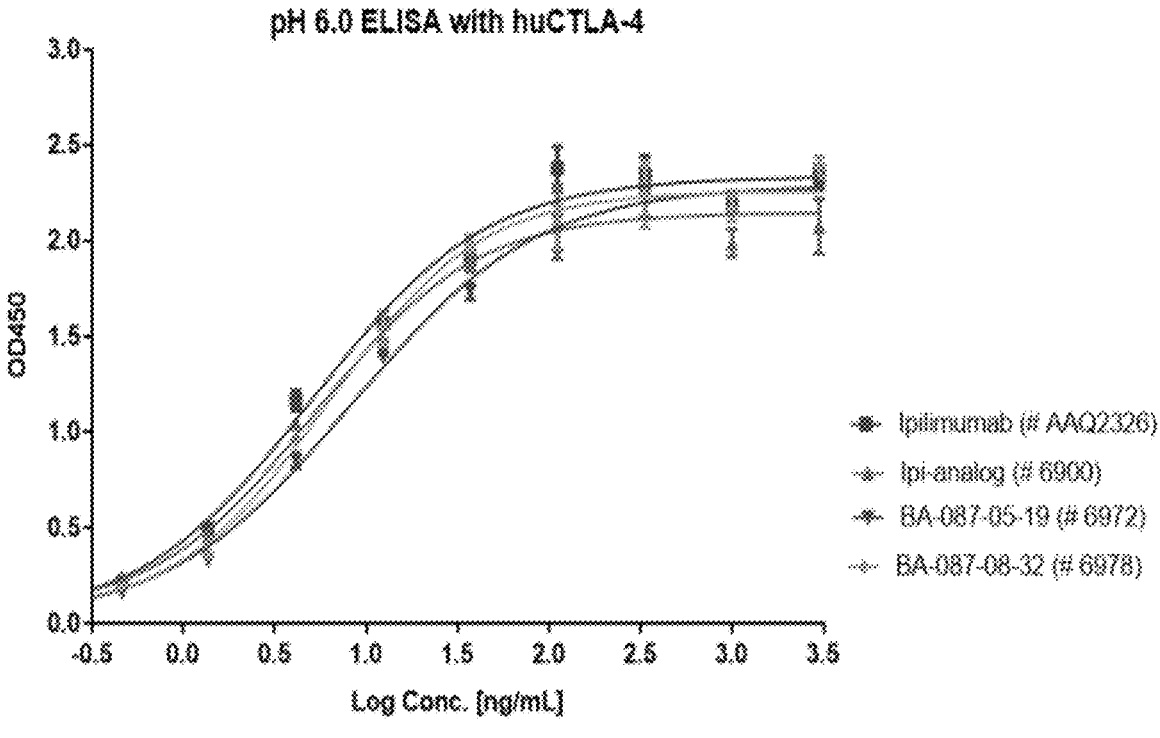
FIG. 3A shows a comparison of the binding activity to human CTLA4 at pH 6.0 of two of the anti-CTLA4 antibodies of the present invention to Ipilimumab and an Ipilimumab analog (Ipi-analog), as measured by enzyme linked immunosorbent assay (ELISA).

In order to facilitate understanding of the examples provided herein, certain frequently occurring terms are defined herein.

In connection with a measured quantity, the term "about" as used herein refers to the normal variation in that measured quantity that would be expected by a skilled person making the measurement and exercising a level of care commensurate with the objective of the measurement and the precision of the measuring equipment used. Unless otherwise indicated, "about" refers to a variation of +/−10% of the value provided.

The term "affinity" as used herein refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "affinity matured" antibody as used herein refers to an antibody with one or more alterations in one or more complimentary determining regions, compared to a parent antibody which does not possess such alterations, such alterations resulting in an improvement in the affinity of the antibody for antigen.

The term "amino acid" as used herein refers to any organic compound that contains an amino group (—NH2) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gin or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (tip or W), tyrosine (tyr or Y), and valine (val or V).

The term "antibody" as used herein refers to intact immunoglobulin molecules, as well as fragments of immunoglobulin molecules, such as Fab, Fab', (Fab')2, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like. Chimeric, human-like, humanized or fully human antibodies are particularly useful for administration to human patients.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

The term "antibody fragment" as used herein refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The terms "anti-CTLA4 antibody," "CTLA4 antibody" and "an antibody that binds to CTLA4" as used herein refer to an antibody that is capable of binding CTLA4 with sufficient affinity such that the antibody is useful as a diagnostic and/or therapeutic agent in targeting CTLA4. In one embodiment, the extent of binding of an anti-CTLA4 antibody to an unrelated, non-CTLA4 protein is less than about 10% of the binding of the antibody to CTLA4 as measured, e.g., by a radioimmunoassay (RIA). In certain embodiments, an antibody that binds to CTLA4 has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$M or less, e.g. from $10^{-8}$M to $10^{-13}$M, e.g., from $10^{-9}$M to $10^{-13}$ M). In certain embodiments, an anti-CTLA4 antibody binds to an epitope of CTLA4 that is conserved among CTLA4 from different species.

The term "binding" as used herein refers to interaction of the variable region or an Fv of an antibody with an antigen with the interaction depending upon the presence of a particular structure (e.g., an antigenic determinant or epitope) on the antigen. For example, an antibody variable region or Fv recognizes and binds to a specific protein structure rather than to proteins generally. As used herein, the term "specifically binding" or "binding specifically" means that an antibody variable region or Fv binds to or associates with more frequently, more rapidly, with greater duration and/or with greater affinity with a particular antigen than with other proteins. For example, an antibody variable region or Fv specifically binds to its antigen with greater affinity, avidity, more readily, and/or with greater duration than it binds to other antigens. For another example, an antibody variable region or Fv binds to a cell surface protein (antigen) with materially greater affinity than it does to related proteins or other cell surface proteins or to antigens commonly recognized by polyreactive natural antibodies (i.e., by naturally occurring antibodies known to bind a variety of antigens naturally found in humans). However, "specifically binding" does not necessarily require exclusive binding or non-detectable binding of another antigen, this is meant by the term "selective binding". In one example, "specific binding" of an antibody variable region or Fv (or other binding region) binds to an antigen, means that the an antibody variable region or Fv binds to the antigen with an equilibrium constant (KD) of 100 nM or less, such as 50 nM or less, for example 20 nM or less, such as, 15 nM or less, or 10 nM or less, or 5 nM or less, 2 nM or less, or 1 nM or less.

The terms "cancer" and "cancerous" as used herein refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The terms "cell proliferative disorder" and "proliferative disorder" as used herein refer to disorders that are associated with some degree of abnormal cell proliferation. In one embodiment, the cell proliferative disorder is cancer.

The term "chemotherapeutic agent" as used herein refers to a chemical compound useful in the treatment of cancer. Examples of chemotherapeutic agents include alkylating agents such as thiotepa and cyclosphosphamide (CY-TOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol;

mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMF®); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics," which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrozole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELI-GARD®), goserelin, buserelin, and tripterelin; sex steroids, including progestines such as megestrol acetate and medroxyprogesterone acetate, estrogens such as diethylstilbestrol and premarin, and androgens/retinoids such as flu-oxymesterone, all transretionic acid and fenretinide; ona-pristone; anti-progesterones; estrogen receptor down-regulators (ERDs); anti-androgens such as flutamide, nilutamide and bicalutamide; and pharmaceutically accept-able salts, acids or derivatives of any of the above; as well as combinations of two or more of the above.

The term "chimeric" antibody as used herein refers to an antibody in which a portion of the heavy and/or light chain is derived from a particular source or species, while the remainder of the heavy and/or light chain is derived from a different source or species.

The term "class" of an antibody as used herein refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\mu$, $\delta$, $\epsilon$, $\gamma$, and $\mu$, respectively.

The term "conditionally active antibody" as used herein refers to an antibody which is more active under a condition in the tumor microenvironment compared to under a condition in the non-tumor microenvironment. The conditions in the tumor microenvironment include lower pH, higher concentrations of lactate and pyruvate, hypoxia, lower concentration of glucose, and slightly higher temperature in comparison with non-tumor microenvironment. For example, a conditionally active antibody is virtually inactive at normal body temperature, but is active at a higher temperature in a tumor microenvironment. In yet another aspect, the conditionally active antibody is less active in normal oxygenated blood, but more active under a less oxygenated environment exists in tumor. In yet another aspect, the conditionally active antibody is less active in normal physiological pH 7.2-7.8, but more active under an acidic pH 5.8-7.0, or 6.0-6.8 that exists in a tumor microenvironment. There are other conditions in the tumor microenvironment know to a person skilled in the field may also be used as the condition in the present invention under which the anti-CTLA4 antibodies to have different binding affinity to CTLA4.

The term "constitutive" as used herein, as for example applied to CTLA4 activity, refers to continuous signaling activity of the receptor kinase that is not dependent on the presence of a ligand or other activating molecules. Depending on the nature of the receptor kinase, all of the activity may be constitutive or the activity of the receptor may be further activated by the binding of other molecules (e.g. ligands). Cellular events that lead to activation of receptor kinase are well known among those of ordinary skill in the art. For example, activation may include oligomerization, e.g., dimerization, trimerization, etc., into higher order receptor complexes. Complexes may comprise a single species of protein, i.e., a homomeric complex. Alternatively, complexes may comprise at least two different protein species, i.e., a heteromeric complex. Complex formation may be caused by, for example, overexpression of normal or mutant forms of receptor on the surface of a cell. Complex formation may also be caused by a specific mutation or mutations in a receptor.

The term "cytostatic agent" as used herein refers to a compound or composition which arrests growth of a cell either in vitro or in vivo. Thus, a cytostatic agent may be one which significantly reduces the percentage of cells in S phase. Further examples of cytostatic agents include agents that block cell cycle progression by inducing G0/G1 arrest or M-phase arrest. The humanized anti-Her2 antibody trastuzumab (HERCEPTIN®) is an example of a cytostatic agent that induces G0/G1 arrest. Classical M-phase blockers include the vincas (vincristine and vinblastine), taxanes, and topoisomerase II inhibitors such as doxorubicin, epirubicin, daunorubicin, etoposide, and bleomycin. Certain agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents a cellular function and/or causes cell death or destruction. Cytotoxic agents include, but are not limited to radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "diabodies" as used herein refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites.

The term "detectably label" as used herein refers to any substance whose detection or measurement, either directly or indirectly, by physical or chemical means, is indicative of the presence of the CTCs in a sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

The term "diagnostics" as used herein refers to determination of a subject's susceptibility to a disease or disorder, determination as to whether a subject is presently affected by a disease or disorder, prognosis of a subject affected by a disease or disorder (e. g., identification of pre-metastatic or metastatic cancerous states, stages of cancer, or responsiveness of cancer to therapy), and therametrics (e. g., monitoring a subject's condition to provide information as to the effect or efficacy of therapy). In some embodiments, the diagnostic method of this invention is particularly useful in detecting early stage cancers.

The term "diagnostic agent" as used herein refers to a molecule which can be directly or indirectly detected and is used for diagnostic purposes. The diagnostic agent may be administered to a subject or a sample. The diagnostic agent can be provided per se or may be conjugated to a vehicle such as a conditionally active antibody.

The term "effector functions" as used herein refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "effective amount" of an agent as used herein, e.g., a pharmaceutical formulation, refers to an amount effective, at dosages and for periods of time necessary, to achieve the desired therapeutic or prophylactic result.

The term "Fc region" as used herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The term "framework" or "FR" as used herein refers to variable domain residues other than hypervariable region (HVR or H1-3 in the heavy chain and L1-3 in the light chain) residues. The FR of a variable domain generally consists of four FR domains: FR1, FR2, FR3, and FR4. Accordingly, the HVR and FR sequences generally appear in the following sequence in $V_H$ (or $V_L$): FR1-H1(L1)-FR2-H2(L2)-FR3-H3(L3)-FR4.

The term "full length antibody," "intact antibody," or "whole antibody" refers to an antibody which comprises an antigen-binding variable region ($V_H$ or $V_L$) as well as a light chain constant domain (CL) and heavy chain constant domains, CH1, CH2 and CH3. The constant domains may be native sequence constant domains (e.g. human native sequence constant domains) or amino acid sequence variants thereof. Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

The terms "host cell," "host cell line," and "host cell culture" as used herein are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "human antibody" as used herein is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "human consensus framework" as used herein is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the $V_L$, the subgroup is subgroup kappa I as in Kabat et al., supra. In one embodiment, for the $V_H$, the subgroup is subgroup III as in Kabat et al., supra.

The term "humanized" antibody as used herein refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and/or form structurally defined loops ("hypervariable loops"). Generally, native four-chain antibodies comprise six HVRs; three in the $V_H$ (H1, H2, H3), and three in the $V_L$ (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol., vol. 196, pp. 901-917 1987) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. 1991).

With the exception of CDR1 in $V_H$, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.*, vol. 13, pp. 1619-1633, 2008). Unless otherwise indicated, HVR residues and other residues in the variable domain (e.g., FR residues) are numbered herein according to Kabat et al., supra.

The term "immunoconjugate" as used herein is an antibody or antibody fragment conjugated to one or more heterologous molecule(s), including but not limited to a cytotoxic agent, a chemotherapeutic agent, a radioactive atom, or a cytostatic agent.

The term "individual" or "subject" as used herein refers to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "inhibiting cell growth or proliferation" as used herein means decreasing a cell's growth or proliferation by at least 10%, 20%, 30%, 40%, 50%, 60%, 70%, 80%, 90%, 95%, or 100%, and includes inducing cell death.

The term "isolated" antibody as used herein is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase High Performance Liquid Chromatography (HPLC)). For review of methods for assessment of antibody purity, see, e.g., Flatman et al., *J. Chromatogr. B*, vol. 848, pp. 79-87, 2007.

The term "isolated" nucleic acid as used herein refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "isolated nucleic acid encoding an anti-CTLA4 antibody" as used herein refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "ligand-independent" as used herein, as for example applied to receptor signaling activity, refers to signaling activity that is not dependent on the presence of a ligand. A receptor having ligand-independent kinase activity will not necessarily preclude the binding of ligand to that receptor to produce additional activation of the kinase activity.

The term "metastasis" as used herein refers to all CTLA4-involving processes that support cancer cells to disperse from a primary tumor, penetrate into lymphatic and/or blood vessels, circulate through the bloodstream, and grow in a distant focus (metastasis) in normal tissues elsewhere in the body. In particular, it refers to cellular events of tumor cells such as proliferation, migration, anchorage independence, evasion of apoptosis, or secretion of angiogenic factors, that underlie metastasis and are stimulated or mediated by non-catalytic or catalytic activities of CTLA4, preferably including CTLA4 phosphorylation and/or CTLA4-mediated signal transduction.

The term "microenvironment" as used herein means any portion or region of a tissue or body that has constant or temporal, physical or chemical differences from other regions of the tissue or regions of the body. For tumors, the term "tumor microenvironment" as used herein refers to the environment in which a tumor exists, which is the non-cellular area within the tumor and the area directly outside the tumorous tissue but does not pertain to the intracellular compartment of the cancer cell itself. The tumor and the tumor microenvironment are closely related and interact constantly. A tumor can change its microenvironment, and the microenvironment can affect how a tumor grows and spreads.

Typically, the tumor microenvironment has a low pH in the range of 5.0 to 7.0, or in the range of 5.0 to 6.8, or in the range of 5.8 to 6.8, or in the range of 6.2-6.8. On the other hand, a normal physiological pH is in the range of 7.2-7.8. The tumor microenvironment is also known to have lower concentration of glucose and other nutrients, but higher concentration of lactic acid, in comparison with blood plasma. Furthermore, the tumor microenvironment can have a temperature that is 0.3 to 1° C. higher than the normal physiological temperature. The tumor microenvironment has been discussed in Gillies et al., "MRI of the Tumor Microenvironment," *Journal of Magnetic Resonance Imaging*, vol. 16, pp. 430-450, 2002, hereby incorporated by reference herein its entirety. The term "non-tumor microenvironment" refers to a microenvironment at a site other than a tumor.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "naked antibody" as used herein refers to an antibody that is not conjugated to a heterologous moiety (e.g., a cytotoxic moiety) or radiolabel. The naked antibody may be present in a pharmaceutical formulation.

The term "native antibodies" as used herein refers to naturally occurring immunoglobulin molecules with varying structures. For example, native IgG antibodies are hetero-tetrameric glycoproteins of about 150,000 daltons, composed of two identical light chains and two identical heavy chains that are disulfide-bonded. From N- to C-terminus, each heavy chain has a variable region ($V_H$), also called a variable heavy domain or a heavy chain variable domain, followed by three constant domains (CH1, CH2, and CH3). Similarly, from N- to C-terminus, each light chain has a variable region ($V_L$), also called a variable light domain or a light chain variable domain, followed by a constant light ($C_L$) domain. The light chain of an antibody may be assigned to one of two types, called kappa ($\kappa$) and lambda ($\lambda$), based on the amino acid sequence of its constant domain.

The term "package insert" as used herein is used to refer to instructions customarily included in commercial packages of therapeutic products, that contain information about the indications, usage, dosage, administration, combination therapy, contraindications and/or warnings concerning the use of such therapeutic products.

The term "percent (%) amino acid sequence identity" with respect to a reference polypeptide sequence as used herein is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" as used herein refers to a preparation which is in such form as to permit the biological activity of an active ingredient contained therein to be effective, and which contains no additional components which are unacceptably toxic to a subject to which the formulation would be administered.

The term "pharmaceutically acceptable carrier" as used herein refers to an ingredient in a pharmaceutical formulation, other than an active ingredient, which is nontoxic to a subject. A pharmaceutically acceptable carrier includes, but is not limited to, a buffer, excipient, stabilizer, or preservative.

The terms "purified" and "isolated" used herein refer to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

The term "recombinant antibody" as used herein refers to an antibody (e.g. a chimeric, humanized, or human antibody or antigen-binding fragment thereof) that is expressed by a recombinant host cell comprising nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia. coli* cells or *Bacillus subtilis* cells, etc.

The term "CTLA4" as used herein, refers to an immune checkpoint that has the amino acid sequence as described in U.S. Pat. Nos. 5,434,131, 5,844,095, and 5,851,795, or any portion or derivative thereof, that recognizes and binds a B7 or interferes with a B7 so that it blocks binding to CD28 and/or CTLA4 (e.g., endogenous CD28 and/or CTLA4). In particular embodiments, the extracellular domain of wild type CTLA4 begins with methionine at position +1 and ends at aspartic acid at position +124, or the extracellular domain of wild type CTLA4 begins with alanine at position −1 and ends at aspartic acid at position +124. Wild type CTLA4 is a cell surface protein, having an N-terminal extracellular domain, a transmembrane domain, and a C-terminal cytoplasmic domain. The extracellular domain binds to target molecules, such as a B7 molecule. In a cell, the naturally occurring, wild type CTLA4 protein is translated as an immature polypeptide, which includes a signal peptide at the N-terminal end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. Alternatively, the signal peptide may not be removed completely, generating molecules that begin before the common starting amino acid methionine. Thus, the mature CTLA4 protein may start at methionine at position +1 or alanine at position −1. The mature form of the CTLA4 molecule includes the extracellular domain or any portion thereof.

The term "therapeutically effective amount" of the antibody of the invention is meant a sufficient amount of the antibody to treat said cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

The term "single chain Fv" ("scFv") as used herein is a covalently linked $V_H$::$V_L$ heterodimer which is usually expressed from a gene fusion including $V_H$ and $V_L$ encoding genes linked by a peptide-encoding linker. "dsFv" is a $V_H$::$V_L$ heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "treatment," "treat," or "treating" as used herein refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "tumor" as used herein refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "variable region" or "variable domain" as used herein refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., *J. Immunol.*, vol. 150, pp. 880-887, 1993; Clarkson et al., *Nature*, vol. 352, pp. 624-628, 1991.

The term "vector" as used herein refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

DETAILED DESCRIPTION

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

A. Anti-CTLA4 Antibodies

In one aspect, the present invention provides an isolated heavy chain variable region polypeptide that specifically binds to human CTLA4 protein. The isolated heavy chain variable region polypeptide comprises three complementarity determining regions having the H1, H2, and H3, wherein:

(SEQ ID NO: 1)
the H1 sequence is GFTFSHYTMH;

(SEQ ID NO: 2)
the H2 sequence is $FIX_1YX_2GNX_3KX_4X_5AX_6SX_7KG$;
and (SEQ ID NO: 3)
the H3 sequence is $TGWLGPFDX_8$, wherein $X_1$ is S or D; $X_2$ is D, H or I, $X_3$ is N or Y; $X_4$ is Y or I; $X_5$ is Y or E; $X_6$ is D or K; $X_7$ is V or M; and $X_8$ is Y or I.

The alignments of exemplary isolated heavy chain variable regions of the present invention are shown in FIG. 1, where the complementarity determining regions H1, H2, and H3 are boxed.

In another aspect, the present invention provides an isolated light chain variable region polypeptide that specifically binds to human CTLA4 protein. The isolated light chain variable region polypeptide comprises three complementarity determining regions having the sequences L1, L2, and L3, wherein:

(SEQ ID NO: 4)
the L1 sequence is $RX_9SQX_{10}X_{11}GSSYLA$;

-continued (SEQ ID NO: 5)
the L2 sequence is $GAFSRATGX_{12}$;
and (SEQ ID NO: 6)
the L3 sequence is QQDGSSPWT, wherein $X_9$ is A or I; $X_{10}$ is Y, S or H; $X_{11}$ is V or G; $X_{12}$ is V or I.

The alignments of exemplary isolated light chain variable regions of the present invention are shown in FIG. 2, where the complementarity determining regions L1, L2, and L3 are boxed.

The isolated heavy chain variable region polypeptides and the isolated light chain variable region polypeptides of the present invention were each obtained from a parent antibody using a method disclosed in U.S. Pat. No. 8,709,755. This method of generating The isolated heavy chain variable region polypeptides and the isolated light chain variable region polypeptides, as well as the method of generating antibodies and antibody fragments disclosed in U.S. Pat. No. 8,709,755 are hereby incorporated by reference herein.

In another aspect, the present invention includes the heavy chain variable regions shown in FIG. 1 and the light chain variable regions shown in FIG. 2. The amino acid sequences of the 16 heavy chain variable regions of FIG. 1 are set forth in SEQ ID NOS: 8, 10, 12, 14, 16, 18, 20, 22, 24, 26, 28, 30, 32, 34, 36, 38. The amino acid sequences of the 16 light chain variable regions of FIG. 1 are set forth in SEQ ID NOS: 7, 9, 11, 13, 15, 17, 19, 21, 23, 25, 27, 29, 31, 33, 35, 37. Antibodies and antibody fragments including these heavy chain variable regions and light chain variable regions can specifically bind to human CTLA4. Antibodies or antibody fragments comprising a combination of one of these heavy chain variable regions and one of these light chain variable regions have been found to have higher binding affinity to CTLA4 at a pH in the tumor microenvironment (e.g. pH 6.0-6.2) than at a pH in a non-tumor microenvironment (e.g. pH 7.4). As a result, the anti-CTLA4 antibodies or antibody fragments have a higher binding affinity to CTLA4 in a tumor microenvironment in comparison with their binding affinity to CTLA4 in a normal tissue microenvironment.

Anti-CTLA4 antibodies or antibody fragments of the present invention thus have reduced side-effects due to their reduced binding affinity to CTLA4 in the normal tissue microenvironment, as well as comparable efficacy, in comparison with monoclonal anti-CTLA4 antibodies known in the art. These features permit use of a higher dosage of these anti-CTLA4 antibodies or antibody fragments to be delivered to a patient thus providing a more effective therapeutic option.

Though the present invention includes the heavy chain variable regions and light chain variable regions presented in FIGS. 1-2 and those having amino acid sequences of SEQ ID NOS: 7-38, the present invention also includes variants thereof that can specifically bind to human CTLA4. In some embodiments, these variants have different H2, H3, I1 and I2 sequences. In other embodiments, the amino acid sequence of the heavy chain variable regions and light chains variable regions outside of the complementarity determining regions may be mutated in accordance with the principles of substitution, insertion and deletion as discussed in this application. In still further embodiments, the constant regions may be modified to provide variants.

In deriving these variants, one is guided by the process as described herein. The variants of the heavy chain variable regions and light chain variable regions may be prepared by introducing appropriate modifications into the nucleotide sequence encoding the heavy chain variable regions and light chain variable regions, or by peptide synthesis. Such modifications include, for example, deletions from, and/or insertions into and/or substitutions of residues within the amino acid sequences of the heavy chain variable regions and light chain variable regions. Any combination of deletion, insertion, and substitution can be made to arrive at the antibodies or antibody fragments of the present invention, provided that they possess the desired characteristics, e.g., antigen-binding to human CTLA4 and/or conditional activity.

Substitution, Insertion, and Deletion Variants

In certain embodiments, antibody or antibody fragment variants having one or more amino acid substitutions are provided. Sites of interest for substitutional mutagenesis include the CDRs and framework regions (FRs). Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody or antibody fragment of interest and the products screened for a desired activity, e.g., retained/improved antigen binding, or decreased immunogenicity.

TABLE 1

| Amino acid substitutions | | |
| --- | --- | --- |
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.*, vol. 207, pp. 179-196, 2008), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology*, vol. 178, pp. 1-37, 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody or antibody fragment to bind antigen. For example, conservative alterations (e.g., conservative substitutions as provided herein) that do not substantially reduce binding affinity may be made in CDRs. Such alterations may be outside of CDR "hotspots" or SDRs. In certain embodiments of the variant $V_H$ and $V_L$ sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells, *Science*, vol. 244, pp. 1081-1085, 1989. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody or antibody fragment with antigen is affected. Further substitutions may be introduced at the amino acid locations demonstrating functional sensitivity to the initial substitutions. Alternatively, or additionally, a crystal structure of an antigen-antibody complex to identify contact points between the antibody or antibody fragment and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody include the fusion to the N- or C-terminus of the antibody to an enzyme (e.g. for ADEPT) or a polypeptide which increases the serum half-life of the antibody.

Amino acid sequence modification(s) of the antibodies described herein are contemplated. For example, it may be desirable to improve the binding affinity and/or other biological properties of the antibody. It is known that when a humanized antibody is produced by simply grafting only CDRs in $V_H$ and $V_L$ of an antibody derived from a non-human animal in FRs of the $V_H$ and $V_L$ of a human antibody, the antigen binding activity is reduced in comparison with that of the original antibody derived from a non-human animal. It is considered that several amino acid residues of the $V_H$ and $V_L$ of the non-human antibody, not only in CDRs but also in FRs, are directly or indirectly associated with the antigen binding activity. Hence, substitution of these amino acid residues with different amino acid residues derived from FRs of the $V_H$ and $V_L$ of the human antibody would reduce of the binding activity. In order to resolve the problem, in antibodies grafted with human CDR, attempts have to be made to identify, among amino acid sequences of the FR of the $V_H$ and $V_L$ of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the sequences of the antibodies or antibody fragments of the invention, or corresponding DNA sequences which encode said antibodies or antibody fragments, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH*, vol. 15, pp.

26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.*, vol. 336, pp. 1239-1249, 2004; Yamane-Ohnuki et al. *Biotech. Bioeng.*, vol. 87, pp. 614-622, 2004. Examples of cell lines capable of producing defucosylated antibodies include Lec13 CHO cells deficient in protein fucosylation (Ripka et al. *Arch. Biochem. Biophys.*, vol. 249, pp. 533-545, 1986; US Pat Appl No US 2003/0157108 A; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.*, vol. 87, pp. 614-622, 2004; Kanda, Y. et al., *Biotechnol. Bioeng.*, vol. 94, pp. 680-688, 2006; and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.*, vol. 9, pp. 457-492, 1991. Non-limiting examples of in vitro assays to assess ADCC activity of a molecule of interest is described in U.S. Pat. No. 5,500,362 (see also, e.g. Hellstrom et al. *Proc. Nat'l Acad. Sci. USA*, vol. 83, pp. 7059-7063, 1986) and Hellstrom, I et al., *Proc. Nat'l Acad. Sci. USA*, vol. 82, pp. 1499-1502, 1985; U.S. Pat. No. 5,821,337 (see also Bruggemann et al., *J. Exp. Med.*, vol. 166, pp. 1351-1361, 1987). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA*, vol. 95, pp. 652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods*, vol. 202, pp. 163-171, 1996; Cragg, M. S. et al., *Blood*, vol. 101, pp. 1045-1052, 2003; and Cragg, M. S, and M. J. Glennie, *Blood*, vol. 103, pp. 2738-2743, 2004). FcRn binding and in vivo clearance/half life determinations can also be performed using methods known in the art (see, e.g., Petkova, S. B. et al., *Int'l. Immunol.*, vol. 18, pp. 1759-1769, 2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.*, vol. 9, pp. 6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.*, vol. 164, pp. 4178-4184, 2000.

Antibodies with increased half lives and improved binding to the neonatal Fc receptor (FcRn), which is responsible for the transfer of maternal IgGs to the fetus (Guyer et al., *J. Immunol.*, vol. 117, pp. 587-593, 1976 and Kim et al., *J. Immunol.*, vol. 24, p. 249, 1994), are described in US2005/0014934. Those antibodies comprise an Fc region with one or more substitutions therein which improve binding of the Fc region to FcRn. Such Fc variants include/e those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature, vol.* 322, pp. 738-740, 1988; U.S. Pat. Nos. 5,648,260; 5,624,821; and WO 94/29351 concerning other examples of Fc region variants.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated as described, e.g., in U.S. Pat. No. 7,521,541.

Antibody Derivatives

In certain embodiments, an antibody or antibody fragment provided herein may be further modified to contain additional nonproteinaceous moieties that are known in the art and readily available. The moieties suitable for derivatization of the antibody or antibody fragment include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody or antibody fragment may vary, and if more than one polymer are attached, they can be the same or different molecules. In general, the number and/or type of polymers used for derivatization can be determined based on considerations including, but not limited to, the particular properties or functions of the antibody or antibody fragment to be improved, whether the derivative will be used in a therapy under defined conditions, etc.

In another embodiment, conjugates of an antibody or antibody fragment and nonproteinaceous moiety that may be selectively heated by exposure to radiation are provided. In one embodiment, the nonproteinaceous moiety is a carbon nanotube (Kam et al., *Proc. Natl. Acad. Sci. USA*, vol. 102, pp. 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In another aspect, the present invention provides an anti-CTLA4 antibody or antibody fragment including the isolated heavy chain variable region polypeptides or isolated light chain variable region polypeptides. The isolated heavy chain variable region polypeptides comprise the H1, H2, and H3 regions with SEQ ID NOS: 8, 10, 12, 14, 16, 18, 20, 22, 24, 26, 28, 30, 32, 34, 36, 38. The isolated light chain variable region polypeptides comprise the L1, L2, and L3 regions with SEQ ID NOS: 7, 9, 11, 13, 15, 17, 19, 21, 23, 25, 27, 29, 31, 33, 35, 37.

The anti-CTLA4 antibody or antibody fragment of the invention has a higher binding affinity to CTLA4 under a condition in tumor microenvironment than under a condition in a non-tumor microenvironment. In one embodiment, the condition in tumor microenvironment and the condition in a non-tumor microenvironment are both pH. The anti-CTLA4 antibodies or antibody fragments of the invention thus can selectively bind to CTLA4 at a pH about 5.0-6.8 but will have a lower binding affinity to CTLA4 at a pH about 7.2-7.8 encountered in a normal physiological environment. As shown Examples 2-3, the anti-CTLA4 antibodies or antibody fragments have higher binding affinity to CTLA4 at pH 6.0 that at pH 7.4.

In certain embodiments, the anti-CTLA4 antibodies or antibody fragments of the present invention have a dissociation constant (Kd) with CTLA4 under a condition in tumor microenvironment of about $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$M or less, or from $10^{-8}$M to $10^{-13}$M, or from $10^{-9}$M to $10^{-13}$ M). In one embodiment, the ratio of the Kd of the antibody or antibody fragment with CTLA4 at a value of the condition in tumor microenvironment to the Kd at a different value of the same condition in non-tumor microenvironment is at least about 1.5:1, at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 50:1, at least about 70:1, or at least about 100:1.

In one embodiment, Kd is measured by a radiolabeled antigen binding assay (RIA) performed with the Fab version of an antibody of interest and its antigen using the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at about 10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

The anti-CTLA4 antibodies of the invention may be a chimeric, humanized or human antibody. In one embodiment, an anti-CTLA4 antibody fragment is employed, e.g., a Fv, Fab, Fab', Fab'-SH, scFv, a diabody, a triabody, a tetrabody or an F(ab')$_2$ fragment and multispecific antibodies formed from antibody fragments. In another embodiment, the antibody is a full length antibody, e.g., an intact IgG antibody or other antibody class or isotype as defined herein. For a review of certain antibody fragments, see Hudson et al. *Nat. Med.*, vol. 9, pp. 129-134, 2003. For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869, 046.

The diabodies of the invention may be bivalent or bispecific. See, for example, EP 404,097; WO 1993/01161; Hudson et al., *Nat. Med.* 9:129-134 (2003); and Hollinger et al., *Proc. Natl. Acad. Sci. USA*, vol. 90, pp. 6444-6448, 1993 for examples of diabodies. Examples of triabodies and tetrabodies are also described in Hudson et al., *Nat. Med.*, vol. 9, pp. 129-134, 2003.

In some embodiments, the invention comprises single-domain antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

In some embodiments, the anti-CTLA4 antibodies of the invention may be chimeric antibodies. Certain chimeric antibodies are described, e.g., in U.S. Pat. No. 4,816,567; and Morrison et al., *Proc. Natl. Acad. Sci. USA*, vol. 81, pp. 6851-6855, 1984). In one example, the chimeric antibody comprises a non-human variable region (e.g., a variable region derived from a mouse, rat, hamster, rabbit, or non-human primate, such as a monkey) and a human constant region. In a further example, the chimeric antibody is a "class switched" antibody in which the class or subclass has been changed relative to the class or subclass of the parent antibody. Chimeric antibodies include antigen-binding fragments thereof.

In certain embodiments, the chimeric antibody of the invention is a humanized antibody. Typically, such a non-human antibody is humanized to reduce immunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody may optionally also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, *Front. Biosci.*, vol. 13, pp. 1619-1633, 2008, and are further described, e.g., in Riechmann et al., *Nature*, vol. 332, pp. 323-329, 1988; Queen et al., *Proc. Nat'l Acad. Sci. USA*, vol. 86, pp. 10029-10033, 1989; U.S. Pat. Nos. 5,821,337, 7,527,791, 6,982,321, and 7,087,409; Kashmiri et al., *Methods*, vol. 36, pp. 25-34, 2005 (describing SDR (a-CDR) grafting); Padlan, *Mol. Immunol.*, vol. 28, pp. 489-498, 1991 (describing "resurfacing"); Dall'Acqua et al., *Methods*, vol. 36, pp. 43-60, 2005 (describing "FR shuffling"); and Osbourn et al., *Methods*, vol. 36, pp. 61-68, 2005 and Klimka et al., *Br. J. Cancer*, vol. 83, pp. 252-260, 2000 (describing the "guided selection" approach to FR shuffling).

Human framework regions that may be used for humanization include but are not limited to: framework regions selected using the "best-fit" method (see, e.g., Sims et al. *J. Immunol.*, vol. 151, p. 2296, 1993); framework regions derived from the consensus sequence of human antibodies of a particular subgroup of light or heavy chain variable regions (see, e.g., Carter et al. *Proc. Natl. Acad. Sci. USA*, vol. 89, p. 4285, 1992; and Presta et al. *J. Immunol.*, vol. 151, p. 2623, 1993); human mature (somatically mutated) framework regions or human germline framework regions (see, e.g., Almagro and Fransson, *Front. Biosci.*, vol. 13, pp.

1619-1633, 2008); and framework regions derived from screening FR libraries (see, e.g., Baca et al., *J. Biol. Chem.*, vol. 272, pp. 10678-10684, 1997 and Rosok et al., *J. Biol. Chem.*, vol. 271, pp. 22611-22618, 1996).

In some embodiments, the anti-CTLA4 antibodies of the invention are multispecific, e.g. bispecific antibodies. Multispecific antibodies are monoclonal antibodies that have binding specificities for at least two different sites. In certain embodiments, one of the binding specificities is for CTLA4 and the other is for another antigen. In certain embodiments, bispecific antibodies may bind to two different epitopes of CTLA4. Bispecific antibodies may also be used to localize cytotoxic agents to cells which express CTLA4. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature*, vol. 305, pp. 537-540, 1983), WO 93/08829, and Traunecker et al., *EMBO J.* vol. 10, pp. 3655-3659, 1991), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, vol. 229, pp. 81-83, 1985); using leucine zippers to produce bi-specific antibodies (see, e.g., Kostelny et al., *J. Immunol.*, vol. 148, pp. 1547-1553, 1992); using "diabody" technology for making bispecific antibody fragments (see, e.g., Hollinger et al., *Proc. Natl. Acad. Sci. USA*, vol. 90, pp. 6444-6448, 1993); and using single-chain Fv (scFv) dimers (see, e.g. Gruber et al., *J. Immunol.*, vol. 152, pp. 5368-5374, 1994); and preparing trispecific antibodies as described, e.g., in Tutt et al. *J. Immunol.*, vol. 147, pp. 60-69, 1991.

Engineered antibodies with three or more functional antigen binding sites, including "Octopus antibodies," are also included herein (see, e.g. US 2006/0025576A1).

The anti-CTLA4 antibodies or antibody fragments of the invention may be produced using recombinant methods and compositions, which are described in detail in US 2016/0017040.

The physical/chemical properties and/or biological activities of the anti-CTLA4 antibodies or antibody fragments of the invention may be tested and measured by various assays known in the art. Some of these assays are described in U.S. Pat. No. 8,853,369.

B. Immunoconjugates

In another aspect, the invention also provides immunoconjugates comprising an anti-CTLA4 antibody or antibody fragment conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, the immunoconjugate is an antibody-drug conjugate (ADC) in which an antibody or antibody fragment is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714, 586, 5,739,116, 5,767,285, 5,770,701, 5,770,710, 5,773,001, and 5,877,296; Hinman et al., *Cancer Res.*, vol. 53, pp.

3336-3342, 1993; and Lode et al., *Cancer Res.*, vol. 58, pp. 2925-2928, 1998); an anthracycline such as daunomycin or doxorubicin (see Kratz et al., *Current Med. Chem.*, vol. 13, pp. 477-523, 2006; Jeffrey et al., *Bioorganic & Med. Chem. Letters*, vol. 16, pp. 358-362, 2006; Torgov et al., *Bioconj. Chem.*, vol. 16, pp. 717-721, 2005; Nagy et al., *Proc. Natl. Acad. Sci. USA*, vol. 97, pp. 829-834, 2000; Dubowchik et al., *Bioorg. & Med. Chem. Letters*, vol. 12, vol. 1529-1532, 2002; King et al., *J. Med. Chem.*, vol. 45, pp. 4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody or antibody fragment as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody or antibody fragment as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody/antibody fragment and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, vol. 238, pp. 1098-, 1987. Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.*, vol. 52, pp. 127-131, 1992; U.S. Pat. No. 5,208,020) may be used.

The immunuoconjugates herein expressly contemplate, but are not limited to conjugates prepared with cross-linker reagents including, but not limited to, BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

An exemplary embodiment of an ADC comprises an antibody or antibody fragment (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I as Ab-(L-D)$_p$, where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon et al., *Methods in Enzym.*, vol. 502, pp. 123-138, 2012). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

i) Exemplary Linkers

A "Linker" (L) is a bifunctional or multifunctional moiety that can be used to link one or more moieties such as drug moieties (D) to an antibody or antibody fragment (Ab) to form an immunoconjugate such as an ADC of the Formula I. In some embodiments, ADCs can be prepared using a Linker having reactive functionalities for covalently attaching to the drug and to the antibody. For example, in some embodiments, a cysteine thiol of an antibody or antibody fragment (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al, *Bioconjugate Chemistry*, vol. 15, pp. 765-773, 2004.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl)cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., *Cancer Research*, vol. 52, pp. 127-131, 1992; U.S. Pat. No. 5,208, 020).

In certain embodiments, a linker has the following Formula II as -A$_a$-W$_w$—Y$_y$—, wherein A is a "stretcher unit", and a is an integer from 0 to 1; W is an "amino acid unit", and w is an integer from 0 to 12; Y is a "spacer unit", and y is 0, 1, or 2. An ADC comprising the linker of Formula II has the Formula I(A): Ab-(A$_a$-W$_w$—Y$_y$-D)$_p$, wherein Ab, D, and p are defined as above for Formula I. Exemplary embodiments of such linkers are described in U.S. Pat. No. 7,498,298.

In some embodiments, a linker component comprises a "stretcher unit" (A) that links an antibody to another linker component or to a drug moiety. Nonlimiting exemplary stretcher units are shown below (wherein the wavy line indicates sites of covalent attachment to an antibody, drug, or additional linker components):

MC

MP mPEG

In some embodiments, a linker component comprises an "amino acid unit" (W). In some such embodiments, the amino acid unit allows for cleavage of the linker by a protease, thereby facilitating release of the drug from the immunoconjugate upon exposure to intracellular proteases, such as lysosomal enzymes (Doronina et al., *Nat. Biotechnol.*, vol. 21, pp. 778-784, 2003). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

Typically, peptide-type linkers can be prepared by forming a peptide bond between two or more amino acids and/or peptide fragments. Such peptide bonds can be prepared, for example, according to a liquid phase synthesis method (e.g., E. Schroder and K. Lübke (1965) "The Peptides", volume 1, pp 76-136, Academic Press).

In some embodiments, a linker component comprises a "spacer unit" (Y) that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. *Expert Opin. Ther. Patents*, vol. 15, pp. 1087-1103, 2005). In some embodiments, the spacer unit comprises p-aminobenzyloxycarbonyl (PAB). In some embodiments, an ADC comprising a self-immolative linker has the structure:

wherein Q is —$C_1$-$C_8$ alkyl, —O—($C_1$-$C_8$ alkyl), -halogen, -nitro, or -cyano; m is an integer ranging from 0 to 4; X may be one or more additional spacer units or may be absent; and p ranges from 1 to about 20. In some embodiments, p ranges from 1 to 10, 1 to 7, 1 to 5, or 1 to 4. Nonlimiting exemplary X spacer units include:

wherein $R_1$ and $R_2$ are independently selected from H and $C_1$-$C_6$ alkyl. In some embodiments, $R_1$ and $R_2$ are each —$CH_3$.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al., *Bioorg. Med. Chem. Lett.*, vol. 9, p. 2237-, 1999) and ortho- or para-aminobenzylacetals. In some embodiments, spacers can be used that undergo cyclization upon amide bond hydrolysis, such as substituted and unsubstituted 4-aminobutyric acid amides (Rodrigues et al., *Chemistry Biology*, vol. 2, pp. 223-, 1995), appropriately substituted bicyclo [2.2.1] and bicyclo[2.2.2] ring systems (Storm et al., *J. Amer. Chem. Soc.*, vol. 94, p. 5815-, 1972) and 2-aminophenylpropionic acid amides (Amsberry et al, *J. Org. Chem.*, vol. 55, p. 5867, 1990). Linkage of a drug to the α-carbon of a glycine residue is another example of a self-immolative spacer that may be useful in ADCs (Kingsbury et al., *J. Med. Chem.*, vol. 27, p. 1447, 1984).

In some embodiments, linker L may be a dendritic type linker for covalent attachment of more than one drug moiety to an antibody through a branching, multifunctional linker moiety (Sun et al. *Bioorganic & Medicinal Chemistry Letters*, vol. 12, pp. 2213-2215, 2002; Sun et al., *Bioorganic & Medicinal Chemistry*, vol. 11, pp. 1761-1768, 2003). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:

val-cit

-continued

MC-val-cit

MC-val-cit-PAB wherein $R_1$ and $R_2$ are independently selected from H and $C_1$-$C_6$ alkyl. In some embodiments, $R_1$ and $R_2$ are each —$CH_3$.

Phe-Lys-PAB-Ab wherein n is 0 to 12. In some embodiments, n is 2 to 10. In some embodiments, n is 4 to 8.

Further nonlimiting exemplary ADCs include the structures:

where X is:

Y is:

each R is independently H or $C_1$-$C_6$ alkyl; and n is 1 to 12.

In some embodiments, a linker is substituted with groups that modulate solubility and/or reactivity. As a nonlimiting example, a charged substituent such as sulfonate (—$SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I.

The compounds of the invention expressly contemplate, but are not limited to, ADCs prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N- hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bis-maleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Toki et al., *J. Org. Chem.*, vol. 67, pp. 1866-1872, 2002; Dubowchik, et al., *Tetrahedron Letters*, vol. 38, pp. 5257-60, 1997; Walker, *J. Org. Chem.*, vol. 60, pp. 5352-5355, 1995; Frisch et al., *Bioconjugate Chem.*, vol. 7, pp. 180-186, 1995; U.S. Pat. No. 6,214,345; WO 02/088172; US2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

ii) Exemplary Drug Moieties

1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al., *PNAS*, vol. 99, pp. 7968-7973, 2002). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424,219) (prepared, for example, by the reaction of maytansinol with $H_2S$ or $P_2S_5$); C-14-alkoxymethyl(demethoxy/$CH_2OR$) (U.S. Pat. No. 4,331,598); C-14-hydroxymethyl or acyloxymethyl ($CH_2OH$ or $CH_2OAc$) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. Nos. 633,410; 5,208,020; Chari et al., *Cancer Res.*, vol. 52, pp. 127-131, 1992; Liu et al., *Proc. Nall. Acad. Sci. USA*, vol. 93, pp. 8618-8623, 1996).

All stereoisomers of the maytansinoid drug moiety are contemplated for the ADC of the invention, i.e. any combination of R and S configurations at the chiral carbons (U.S. Pat. Nos. 7,276,497; 6,913,748; 6,441,163; 633,410 (RE39151); U.S. Pat. No. 5,208,020; Widdison et al (2006) *J. Med. Chem.* 49:4392-4408. In some embodiments, the maytansinoid drug moiety has the following stereochemistry:

Exemplary embodiments of maytansinoid drug moieties include, but are not limited to, DM1; DM3; and DM4, having the structures:

DM1

47

DM3

48

DM4 wherein the wavy line indicates the covalent attachment of the sulfur atom of the drug to a linker (L) of an antibody-drug conjugate.

Exemplary antibody-drug conjugates where DM1 is linked through a BMPEO linker to a thiol group of the antibody have the structure and abbreviation:

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1. See also Liu et al., *Proc. Natl. Acad. Sci. USA*, vol. 93, pp. 8618-8623, 1996; and Chari et al., *Cancer Research*, vol. 52, pp. 127-131, 1992.

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020. In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al., *Cancer* Research, vol. 52, pp. 127-131, 1992; US 2005/0276812 A1; and US 2005/016993 A1.

(2) Auristatins and Dolastatins

Drug moieties include dolastatins, auristatins, and analogs and derivatives thereof (U.S. Pat. Nos. 5,635,483; 5,780, 588; 5,767,237; and 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al., *Antimicrob. Agents and Chemother.*, vol. 45, pp. 3580-3584, 2001) and have anticancer (U.S. Pat. No. 5,663,149) and antifungal activity (Pettit et al., *Antimicrob. Agents Chemother.*, vol. 42, pp. 2961-2965, 1998). The dolastatin/auristatin drug moiety may be attached to the antibody through the N (amino) terminus or the C (carboxyl) terminus of the peptidic drug moiety (WO 02/088172; Doronina et al., *Nature* Biotechnology, vol. 21, pp. 778-784, 2003; Francisco et al., *Blood*, vol. 102, pp. 1458-1465, 2003).

Exemplary auristatin embodiments include the N-terminus linked monomethylauristatin drug moieties $D_E$ and $D_F$, disclosed in U.S. Pat. Nos. 7,498,298 and 7,659,241:

wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle); each $R^5$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of e is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of e is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

$$D_E$$

$$D_F$$

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$—

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)$—COOH.

In another embodiment, when Z is —NH, $R^{11}$ is —$CH(R^{15})_2$, wherein $R^{15}$ is —$(CH_2)_n$—$SO_3H$.

An exemplary auristatin embodiment of formula $D_E$ is MMAE, wherein the wavy line indicates the covalent attachment to a linker (L) of an antibody-drug conjugate:

MMAE

10

An exemplary auristatin embodiment of formula $D_E$ is MMAF, wherein the wavy line indicates the covalent attachment to a linker (L) of an antibody-drug conjugate:

(3) Calicheamicin

In some embodiments, the immunoconjugate comprises an antibody or antibody fargment conjugated to one or more

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al., *Bioconjugate Chem.*, vol. 17, pp. 114-124, 2006). In some such embodiments, drug release is believed to be affected by antibody degradation in the cell.

Typically, peptide-based drug moieties can be prepared by forming a peptide bond between two or more amino acids and/or peptide fragments. Such peptide bonds can be prepared, for example, according to a liquid phase synthesis method (see, e.g., E. Schröder and K. Lübke, "The Peptides", volume 1, pp 76-136, 1965, Academic Press). Auristatin/dolastatin drug moieties may, in some embodiments, be prepared according to the methods of: U.S. Pat. Nos. 7,498,298; 5,635,483; 5,780,588; Pettit et al., *J. Am. Chem. Soc.*, vol. 111, pp. 5463-5465, 1998; Pettit et al., *Anti-Cancer Drug Design*, vol. 13, pp. 243-277, 1998; Pettit et al., *Synthesis*, vol. 6, pp. 719-725, 1996; Pettit et al., *J. Chem. Soc. Perkin Trans.* vol. 15, pp. 859-863, 1996; and Doronina, *Nat. Biotechnol.*, vol. 21, pp. 778-784, 2003.

In some embodiments, auristatin/dolastatin drug moieties of formulas $D_E$ such as MMAE, and $D_F$, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al., *Bioconjugate Chem.*, vol. 17, pp. 114-124, 2006; and Doronina et al., *Nat. Biotech.*, vol. 21, pp. 778-784, 2003 and then conjugated to an antibody of interest.

calicheamicin molecules. The calicheamicin family of antibiotics, and analogues thereof, are capable of producing double-stranded DNA breaks at sub-picomolar concentrations (Hinman et al., *Cancer Research*, vol. 53, pp. 3336-3342, 1993; Lode et al., *Cancer Research*, vol. 58, pp. 2925-2928, 1998). Calicheamicin has intracellular sites of action but, in certain instances, does not readily cross the plasma membrane. Therefore, cellular uptake of these agents through antibody-mediated internalization may, in some embodiments, greatly enhance their cytotoxic effects. Nonlimiting exemplary methods of preparing antibody-drug conjugates with a calicheamicin drug moiety are described, for example, in U.S. Pat. Nos. 5,712,374; 5,714,586; 5,739, 116; and 5,767,285.

(4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber et al., *J. Am. Chem. Soc.*, vol. 87, pp. 5793-5795, 1965; Leimgruber et al., *J. Am. Chem. Soc.*, vol. 87, pp. 5791-5793, 1965). Since then, a number of PBDs, both naturally-occurring and analogues, have been reported (Thurston et al., *Chem. Rev.* vol. 1994, pp. 433-465 1994, including dimers of the tricyclic PBD scaffold (U.S. Pat. Nos. 6,884,799; 7,049,311; 7,067,511; 7,265,105; 7,511, 032; 7,528,126; and 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, *Acc. Chem. Res.*, vol. 19, pp. 230-237, 1986). Dimeric PBD compounds bearing C2 aryl substituents have been shown to be useful as cytotoxic agents (Hartley et al *Cancer Res.*, vol. 70, pp. 6849-6858, 2010; Antonow, *J. Med. Chem.* vol. 53, pp. 2927-2941, 2010; Howard et al., *Bioorganic and Med. Chem. Letters*, vol. 19, pp. 6463-6466, 2009).

PBD dimers have been conjugated to antibodies and the resulting ADC shown to have anti-cancer properties. Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of:

and salts and solvates thereof, wherein:

the wavy line indicates the covalent attachment site to the linker;

the dotted lines indicate the optional presence of a double bond between C1 and C2 or C2 and C3;

$R^2$ is independently selected from H, OH, $=O$, $=CH_2$, CN, R, OR, $=CH-R^D$, $=C(R^D)_2$, $O-SO_2-R$, $CO_2R$ and COR, and optionally further selected from halo or dihalo, wherein $R^D$ is independently selected from R, $CO_2R$, COR, CHO, $CO_2H$, and halo;

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

Q is independently selected from O, S and NH;

$R^{11}$ is either H, or R or, where Q is O, $SO_3M$, where M is a metal cation;

R and R' are each independently selected from optionally substituted $C_{1-8}$ alkyl, $C_{1-12}$ alkyl, $C_{3-8}$ heterocyclyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted $C_{1-12}$ alkyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring. In some embodiments, $R^9$ and $R^{19}$ are H. In some embodiments, $R^6$ and $R^{16}$ are H. In some embodiments, $R^7$ are $R^{17}$ are both $OR^{7A}$, where $R^{7A}$ is optionally substituted $C_{1-4}$ alkyl. In some embodiments, $R^{7A}$ is Me. In some embodiments, $R^{7A}$ is $Ch_2Ph$, where Ph is a phenyl group. In some embodiments, X is O. In some embodiments, $R^{11}$ is H. In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted $C_{5-20}$ aryl or $C_{5-7}$ aryl or $C_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from $=O$, $=CH_2$, $=CH-R^D$, and $=C(R^D)_2$. In some embodiments, $R^2$ and $R^{12}$ each $=CH_2$. In some embodiments, $R^2$ and $R^{12}$ are each H. In some embodiments, $R^2$ and $R^{12}$ are each $=O$. In some embodiments, $R^2$ and $R^{12}$ are each $=CF_2$. In some embodiments, $R^2$ and/or $R^{12}$ are independently $=C(R^D)_2$. In some embodiments, $R^2$ and/or $R^{12}$ are independently $=CH-R^D$.

In some embodiments, when $R^2$ and/or $R^{12}$ is $=CH-R^D$, each group may independently have either configuration shown below:

In some embodiments, a $=CH-R^D$ is in configuration (I). In some embodiments, R" is a $C_3$ alkylene group or a $C_5$ alkylene group.

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADCs comprising PBD dimers may be prepared according to methods known in the art. See, e.g., WO 2009/016516; US 2009/304710; US 2010/047257; US 2009/036431; US 2011/0256157; WO 2011/130598.

(5) Anthracyclines

In some embodiments, an ADC may comprise anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments*, p. 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al., *Current Med. Chem.*, vol. 13, pp. 477-523, 2006; Jeffrey et al., *Bioorganic & Med. Chem. Letters*, vol. 16, pp. 358-362. 1996; Torgov et al., *Bioconj. Chem.*, vol.

16, pp. 717-721, 2005; Nagy et al., *Proc. Natl. Acad. Sci. USA*, vol. 97, pp. 829-834, 2000; Dubowchik et al., *Bioorg. & Med. Chem. Letters*, vol. 12, pp. 1529-1532, 2002; King et al., *J. Med. Chem.*, vol. 45, pp. 4336-4343, 2002; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al., *J. Clin. Oncology*, vol. 18, pp. 2282-2292, 2000; Ajani et al., *Cancer Jour.*, vol. 6, pp. 78-81, 2000; Tolcher et al., *J. Clin. Oncology*, vol. 17, pp. 478-484, 1999).

PNU-159682 is a potent metabolite (or derivative) of nemorubicin (Quintieri et al., *Clinical Cancer* Research, vol. 11, pp. 1608-1617, 2005). Nemorubicin is a semisynthetic analog of doxorubicin with a 2-methoxymorpholino group on the glycoside amino of doxorubicin and has been under clinical evaluation (Grandi et al. *Cancer Treat. Rev.* vol. 17, pp. 133-138, 1990; Ripamonti et al. *Brit. J. Cancer*, vol. 65, pp. 703-707, 1992), including phase II/III trials for hepatocellular carcinoma (Sun et al., *Proceedings of the American Society for Clinical Oncology*, vol. 22, Abs1448, 2003; Quintieri, *Proceedings of the American Association of Cancer Research*, vol. 44:1st Ed, Abs 4649, 2003; Pacciarini et al., *Jour. Clin. Oncology*, vol. 24, p. 14116, 2006).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R^1R^2$)-Ab are protease cleavable.

(6) Other Drug Moieties

Drug moieties also include geldanamycin (Mandler et al., *J. Nat. Cancer Inst.*, vol. 92, pp. 1573-1581, 2000; Mandler et al., *Bioorganic & Med. Chem. Letters*, vol. 10, pp. 1025-1028, 2000; Mandler et al., *Bioconjugate Chem.*, vol. 13, pp. 786-791, 2002); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al., *Biochem. Biophys. Res. Commun.*, vol. 80, pp. 49-57, 1978) can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysis, subtilisin, carboxypeptidases and cathepsins (such as cathepsins B and L), which are useful for converting peptide-containing prodrugs into free drugs; D-alanyl-carboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature*, vol. 312, pp. 604-608, 1984.

iii) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody use in the preparation of ADCs from conjugation reactions may be characterized by conventional means such as mass spectroscopy, ELISA assay, and HPLC. The quantitative distribution of ADCs in terms of p may also be determined. In some instances, separation, purification, and characterization of homogeneous ADCs where p is a certain value from ADCs with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADCs with a distribution of one or more drug moieties attached to an antibody. The average number of drugs per antibody may be calculated from the mixture by a dual ELISA antibody assay, which is specific for antibody and specific for the drug. Individual ADCs may be identified in the mixture by mass spectroscopy and separated by HPLC, e.g. hydrophobic interaction chromatography (see, e.g., McDonagh et al., *Prot. Engr. Design & Selection*, vol. 19, pp. 299-307, 2006; Hamblett et al., *Clin. Cancer Res.*, vol. 10, pp. 7063-7070, 2004). In certain embodiments, a homogeneous ADC with a single loading value may be isolated from the conjugation mixture by electrophoresis or chromatography.

iv) Certain Methods of Preparing Immunoconjugates

An immunoconjugate that is an ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges.

Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody or antibody fragment, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, *Bioconjugate Chem.*, vol. 3, pp. 138-146, 1992; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADCs are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody or antibody fragment may be conjugated to a "receptor" (such as streptavidin) for utilization in tumor pre-targeting wherein the antibody/antibody fragment-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

C. Methods and Compositions for Diagnostics and Detection

In certain embodiments, any of the anti-CTLA4 antibodies or antibody fragments provided herein may be used for detecting the presence of CTLA4 in a biological sample.

The term "detecting" as used herein encompasses quantitative or qualitative detection. In certain embodiments, a biological sample comprises a cell or tissue, such as breast, pancreas, esophagus, lung and/or brain cells or tissue.

A further aspect of the invention relates to an anti-CTLA4 antibody or antibody fragment of the invention for diagnosing and/or monitoring a cancer or another disease in which CTLA4 expression levels are increased or decreased from a normal physiological level at at least one location in the body.

In a preferred embodiment, antibodies or antibody fragments of the invention may be labelled with a detectable molecule or substance, such as a fluorescent molecule, a radioactive molecule or any other label known in the art as above described. For example, an antibody or antibody fragment of the invention may be labelled with a radioactive molecule.

For example, suitable radioactive molecules include but are not limited to radioactive atoms used for scintigraphic studies such as $^{123}$I, $^{124}$I, $^{111}$In, $^{16}$Re, and $^{188}$Re. Antibodies or antibody fragments of the invention may also be labelled with a spin label for nuclear magnetic resonance (NMR) imaging, such as iodine-123, iodine-131, indium-Ill, fluorine-19, carbon-13, nitrogen-15, oxygen-17, gadolinium, manganese or iron. Following administration of the antibody, the distribution of the radiolabeled antibody within the patient is detected. Any suitable known method can be used. Some non-limiting examples include, computed tomography (CT), position emission tomography (PET), magnetic resonance imaging (MRI), fluorescence, chemiluminescence and sonography.

Antibodies or antibody fragments of the invention may be useful for diagnosing and staging of cancer and diseases associated with CTLA4 overexpression. Cancers associated with CTLA4 overexpression may include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, and various types of head and neck cancer or other CTLA4 expressing or overexpressing hyperproliferative diseases.

Antibodies or antibody fragments of the invention may be useful for diagnosing diseases other than cancers for which CTLA4 expression is increased or decreased. Both the (soluble or cellular CTLA4 forms can be used for such diagnoses. Typically, such diagnostic methods involve use of a biological sample obtained from the patient. The biological sample encompasses a variety of sample types obtained from a subject that can be used in a diagnostic or monitoring assay. Biological samples include but are not limited to blood and other liquid samples of biological origin, solid tissue samples such as a biopsy specimen or a tissue culture or cells derived therefrom, and the progeny thereof. For example, biological samples include cells obtained from a tissue sample collected from an individual suspected of having a cancer associated with CTLA4 overexpression, and in preferred embodiments from glioma, gastric, lung, pancreatic, breast, prostate, renal, hepatic and endometrial. Biological samples encompass clinical samples, cells in culture, cell supernatants, cell lysates, serum, plasma, biological fluid, and tissue samples.

In a particular embodiment, the invention is a method of diagnosing a cancer associated with CTLA4 overexpression in a subject by detecting CTLA4 on cells from the subject using the antibody of the invention. In particular, said method may include steps of:

(a) contacting a biological sample of a subject with an antibody or antibody fragment according to the invention under conditions suitable for the antibody or antibody fragment to form complexes with cells in the biological sample that express CTLA4; and (b) detecting and/or quantifying said complexes, whereby detection of said complexes is indicative of a cancer associated with CTLA4 overexpression.

In order to monitor the progress of a cancer, the method according to the invention may be repeated at different times, in order to determine if antibody binding to the samples increases or decreases, wherefrom it can be determined if the cancer has progressed, regressed or stabilized.

In a particular embodiment, the invention is a method of diagnosing a disease associated with the expression or overexpression of CTLA4 or a decrease or increase of the soluble form of CTLA4. Examples of such diseases may include human immune disorders, thrombotic diseases (thrombosis and atherothrombosis), and cardiovascular diseases In one embodiment, an anti-CTLA4 antibody or antibody fragment for use in a method of diagnosis or detection is provided. In a further aspect, a method of detecting the presence of CTLA4 in a biological sample is provided. In a further aspect, a method of quantifying the amount of CTLA4 in a biological sample is provided. In certain embodiments, the method comprises contacting the biological sample with an anti-CTLA4 antibody or antibody fragment as described herein under conditions permissive for binding of the anti-CTLA4 antibody or antibody fragment to CTLA4, and detecting whether a complex is formed between the anti-CTLA4 antibody or antibody fragment and CTLA4. Such a method may be carried out in vitro or in vivo. In one embodiment, an anti-CTLA4 antibody or antibody fragment is used to select subjects eligible for therapy. In some embodiments, the therapy will include administration of an anti-CTLA4 antibody or antibody fragment to the subject.

In certain embodiments, labeled anti-CTLA4 antibodies or antibody fragments are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

D. Pharmaceutical Formulations

The anti-CTLA4 antibodies or antibody fragments have cell killing activity. This cell killing activity extends to multiple different types of cell lines. Further, these antibodies or antibody fragments, once conjugated to a cytotoxic agent, can reduce tumor size and may exhibit reduced toxicity. Thus, the anti-CTLA4 antibodies, fragments or immunoconjugates thereof may be useful for treating proliferative diseases associated with CTLA4 expression. The antibodies, fragments or immunoconjugates may be used alone or in combination with any suitable agent or other conventional treatments.

The anti-CTLA4 antibody or antibody fragment may be used to treat diseases associated with CTLA4 expression, overexpression or activation. There are no particular limitations on the types of cancer or tissue that can be treated other than the requirement for CTLA4 expression. Examples include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, and various types of head and neck cancer. More preferable cancers are glioma, gastric, lung, pancreatic, breast, prostate, renal, hepatic and endometrial cancer.

Anti-CTLA4 antibodies or antibody fragments are potential activators of the innate immune response and thus may be used in the treatment of human immune disorders, such as sepsis. The anti-CTLA4 antibody or antibody fragment of the invention may also be used as adjuvants for immunization such as for vaccines and as anti-infection agents against, for example, bacteria, viruses and parasites.

Anti-CTLA4 antibody or antibody fragment may be used to protect against, prevent or treat thrombotic diseases such as venous and arterial thrombosis and atherothrombosis. Anti-CTLA4 antibody or antibody fragment may also be used to protect against, prevent or treat cardiovascular diseases as well as to prevent or inhibit the entry of viruses such as Lassa and Ebola viruses and to treat viral infections.

In each of the embodiments of the treatment methods described herein, the anti-CTLA4 antibody, antibody fragment or anti-CTLA4 antibody or antibody fragment immunoconjugate may be delivered in a manner consistent with conventional methodologies associated with management of the disease or disorder for which treatment is sought. In accordance with the disclosure herein, an effective amount of the antibody, antibody fragment or immunoconjugate is administered to a subject in need of such treatment for a time and under conditions sufficient to prevent or treat the disease or disorder. Thus, an aspect of the invention relates to a method for treating a disease associated with the expression of CTLA4 comprising administering to a subject in need thereof with a therapeutically effective amount of an antibody, antibody fragment or immunoconjugate of the invention.

For administration, the anti-CTLA4 antibody, antibody fragment or immunoconjugate may be formulated as a pharmaceutical composition. The pharmaceutical composition including anti-CTLA4 antibody, antibody fragment or immunoconjugate can be formulated according to known methods for preparing pharmaceutical compositions. In such methods, the therapeutic molecule is typically combined with a mixture, solution or composition containing a pharmaceutically acceptable carrier.

A pharmaceutically acceptable carrier is a material that can be tolerated by a recipient patient. Sterile phosphate-buffered saline is one example of a pharmaceutically acceptable carrier. Other suitable pharmaceutically acceptable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc. These considerations can be taken into account by a skilled person to formulate suitable pharmaceutical compositions. The pharmaceutical compositions of the invention can be formulated for topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition of, for example, sterilized water or physiological saline, permit the constitution of injectable solutions.

In some embodiments, tonicity agents, sometimes known as "stabilizers" are present to adjust or maintain the tonicity of a liquid in a composition. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount of from 0.1% to 25% by weight, preferably 1 to 5% of the pharmaceutical composition. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients may include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-mono-thioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") may be employed to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants may be present in a concentration range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride The doses used for the administration can be adapted as a function of various parameters, and in particular as a function of the mode of administration used, of the relevant pathology, or alternatively of the desired duration of treatment. To prepare pharmaceutical compositions, an effective amount of the antibody or antibody fragment may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in a water suitably mixed with a surfactant. Dispersions can also be prepared in glycerol, liquid polyethylene glycols, and mixtures thereof and in oils. Under ordinary conditions of storage and use, these preparations contain a preservative to prevent the growth of microorganisms.

The anti-CTLA4 antibody or antibody fragment can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with one or more of the other ingredients enumerated above, as may be required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of dimethyl sulfoxide (DMSO) as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies or antibody fragments may be formulated within a therapeutic mixture to deliver about 0.0001 to 10.0 milligrams, or about 0.001 to 5 milligrams, or about 0.001 to 1 milligrams, or about 0.001 to 0.1 milligrams, or about 0.1 to 1.0 or even about 10 milligrams per dose. Multiple doses can also be administered at selected time intervals.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies or antibody fragments into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to degrade in vivo. Biodegradable polyalkyl-cyanoacrylate nanoparticles that meet these requirements are contemplated for use in the present invention, and such particles may be easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations Pharmaceutical formulations containing an anti-CTLA4 antibody or antibody fragment as described herein are prepared by mixing such antibody or antibody fragment having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredient as necessary for the particular indication being treated. Preferably, ingredients with complementary activities that do not adversely affect each other may be combined into a single formulation. For example, it may be desirable to provide an EGFR antagonist (such as erlotinib), an anti-angiogenic agent (such as a VEGF antagonist which may be an anti-VEGF antibody) or a chemotherapeutic agent (such as a taxoid or a platinum agent) in addition to the anti-CTLA4 antibody, antibody fragment or immunoconjugate of the present invention. Such active ingredients are suitably present in combination in amounts that are effective for the purpose intended.

In one embodiment, the anti-CTLA4 antibody, antibody fragment or immunoconjugate of the present invention is combined in a formulation with another antibody or antibody fragment against an antigen selected from PD1, PD-L1, AXL, ROR2, CD3, HER2, B7-H3, ROR1, SFRP4 and a WNT protein including WNT1, WNT2, WNT2B, WNT3, WNT4, WNT5A, WNT5B, WNT6, WNT7A, WNT7B, WNT8A, WNT8B, WNT9A, WNT9B, WNT10A, WNT10B, WNT11, WNT16. The combination may be in the form of two separate molecules: the anti-CTLA4 antibody, antibody fragment or immunoconjugate of the present invention, and the another antibody or antibody fragment. Alternatively, the combination may also be the form of a single molecule with binding affinity to both CTLA4 and the other antigen, thus forming a multispecific (e.g. bispecific) antibody.

Active ingredients may be encapsulated in microcapsules prepared, for example, by coacervation techniques or by interfacial polymerization. For example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions may be employed. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody or antibody fragment, which matrices may be in the form of shaped articles, e.g. films, or microcapsules.

The formulations to be used for in vivo administration are generally sterile. Sterility may be readily accomplished, e.g., by filtration through sterile filtration membranes.

E. Therapeutic Methods and Compositions

Any of the anti-CTLA4 antibodies or antibody fragments provided herein may be used in therapeutic methods. In one aspect, an anti-CTLA4 antibody or antibody fragment for use as a medicament is provided. In further aspects, an anti-CTLA4 antibody or antibody fragment for use in treating cancer (e.g., breast cancer, non-small cell lung cancer, pancreatic cancer, brain cancer, cancer of pancreas, brain, kidney, ovary, stomach, leukemia, uterine endometrium, colon, prostate, thyroid, liver, osteosarcoma, and/or melanoma) is provided. In certain embodiments, an anti-CTLA4 antibody or antibody fragment for use in a method of treatment is provided. In certain embodiments, the invention provides an anti-CTLA4 antibody or antibody fragment for use in a method of treating an individual having cancer comprising administering to the individual an effective amount of the anti-CTLA4 antibody or antibody fragment. In certain embodiments, the invention provides an anti-CTLA4 antibody or antibody fragment for use in a method of treating an individual having an immune disorder (e.g., an autoimmune disorder), a cardiovascular disorder (e.g., atherosclerosis, hypertension, thrombosis), an infectious disease (e.g., Ebola virus, Marburg virus) or diabetes, comprising administering to the individual an effective amount of the anti-CTLA4 antibody or antibody fragment. In one such embodiment, the method further comprises administering to the individual an effective amount of at least one additional therapeutic agent, e.g., as described below. In further embodiments, the invention provides an anti-CTLA4 antibody or antibody fragment for use in inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function.

In certain embodiments, the invention provides an anti-CTLA4 antibody or antibody fragment for use in a method of inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual comprising administering to the individual an effective amount of the anti-CTLA4 antibody or antibody fragment to inhibit angiogenesis, inhibit cell proliferation, inhibit immune function, inhibit inflammatory cytokine secretion (e.g., from tumor-associated macrophages), inhibit tumor vasculature development (e.g., intratumoral vasculature or tumor-associated vasculature), and/or inhibit tumor stromal function. An "individual" according to any of the above embodiments is preferably a human.

In a further aspect, the invention provides for the use of an anti-CTLA4 antibody or antibody fragment in the manufacture or preparation of a medicament. In one embodiment, the medicament is for treatment of cancer (in some embodiments, breast cancer, non-small cell lung cancer, pancreatic cancer, brain cancer, cancer of the pancreas, brain, kidney, ovary, stomach, leukemia, uterine endometrium, colon, prostate, thyroid, liver, osteosarcoma, and/or melanoma). In a further embodiment, the medicament is for use in a method of treating cancer comprising administering to an individual having cancer an effective amount of the medicament. In a further embodiment, the medicament is for use in a method of treating an immune disorder (e.g., an autoimmune disorder), a cardiovascular disorder (e.g., atherosclerosis, hypertension, thrombosis), an infectious disease (e.g., Ebola virus, Marburg virus) or diabetes, comprising administering to the individual an effective amount of the anti-CTLA4 antibody or antibody fragment. In one such embodiment, the method further comprises administering to the individual an effective amount of at least one additional therapeutic agent, e.g., as described below. In a further embodiment, the medicament is for inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function. In a further embodiment, the medicament is for use in a method of inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual comprising administering to the individual an amount effective of the medicament to inhibit angiogenesis, inhibit cell proliferation, promote immune function, induce inflammatory cytokine section (e.g., from tumor-associated macrophages), inhibit tumor vasculature development (e.g., intratumoral vasculature or tumor-associated vasculature), and/or inhibit tumor stromal function. An "individual" according to any of the above embodiments may be a human.

In a further aspect, the invention provides a method for treating a cancer. In one embodiment, the method comprises administering to an individual having such cancer an effective amount of an anti-CTLA4 antibody or antibody fragment. In one such embodiment, the method further comprises administering to the individual an effective amount of at least one additional therapeutic agent, as described below. An "individual" according to any of the above embodiments may be a human.

In a further aspect, the invention provides a method for treating an immune disorder (e.g., an autoimmune disorder), a cardiovascular disorder (e.g., atherosclerosis, hypertension, thrombosis), an infectious disease (e.g., Ebola virus, Marburg virus) or diabetes. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual. In one embodiment, the method comprises administering to the individual an effective amount of an anti-CTLA4 antibody or antibody fragment to inhibit angiogenesis, inhibit cell proliferation, promote immune function, induce inflammatory cytokine section (e.g., from tumor-associated macrophages), inhibit tumor vasculature development (e.g., intratumoral vasculature or tumor-associated vasculature), and/or inhibit tumor stromal function. In one embodiment, an "individual" is a human.

In a further aspect, the invention provides pharmaceutical formulations comprising any of the anti-CTLA4 antibodies or antibody fragments provided herein, e.g., for use in any of the above therapeutic methods. In one embodiment, a pharmaceutical formulation comprises any of the anti-CTLA4 antibodies or antibody fragments provided herein and a pharmaceutically acceptable carrier. In another embodiment, a pharmaceutical formulation comprises any of the anti-CTLA4 antibodies or antibody fragments provided herein and at least one additional therapeutic agent, e.g., as described below.

In each and every treatment described above, the antibodies or antibody fragments of the invention can be used alone, as immunoconjugates or in combination with other agents in a therapy. For instance, an antibody of the invention may be co-administered with at least one additional therapeutic agent. In certain embodiments, an additional therapeutic agent is an anti-angiogenic agent. In certain embodiments, an additional therapeutic agent is a VEGF antagonist (in some embodiments, an anti-VEGF antibody, for example bevacizumab). In certain embodiments, an additional therapeutic agent is an EGFR antagonist (in some embodiment, erlotinib). In certain embodiments, an additional therapeutic agent is a chemotherapeutic agent and/or a cytostatic agent. In certain embodiments, an additional therapeutic agent is a taxoid (e.g., paclitaxel) and/or a platinum agent (e.g., carboplatinum). In certain embodiments the additional therapeutic agent is an agent that enhances the patient's immunity or immune system.

Such combination therapies noted above encompass combined administration (where two or more therapeutic agents are included in the same or separate formulations), and separate administration, in which case, administration of the antibody or antibody fragment can occur prior to, simultaneously, and/or following, administration of the additional therapeutic agent and/or adjuvant. Antibodies or antibody fragments can also be used in combination with radiation therapy.

The anti-CTLA4 antibodies or antibody fragments may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or antibody fragment need not be, but is optionally formulated with one or more agents currently used to prevent or treat the disorder in question. The effective amount of such other agents depends on the amount of antibody or antibody fragment present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or antibody fragment (when used alone or in combination with one or more other additional therapeutic agents) will depend on the type of disease to be treated, the type of antibody or antibody fragment, the severity and course of the disease, whether the antibody or antibody fragment is administered for preventive or therapeutic purposes, previous therapy, the patient's clinical history and response to the antibody or antibody fragment, and the discretion of the attending physician. The antibody or antibody fragment is suitably administered to the patient at one time or over a series of treatments. Depending on the type and severity of the disease, about 1 µg of antibody or antibody fragment/kg bodyweight of the patient to 40 mg of antibody or antibody fragment/kg bodyweight of the patient can be an initial candidate dosage for administration to the patient, whether, for example, by one or more separate administrations, or by continuous infusion. One typical daily dosage might range from about 1 µg of antibody or antibody fragment/kg bodyweight of the patient to 100 mg of antibody or antibody fragment/kg bodyweight of the patient or more, depending on the factors mentioned above. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody or antibody fragment). An initial higher loading dose, followed by one or more lower doses may be administered. However, other dosage regimens may be useful. The progress of this therapy is easily monitored by conventional techniques and assays.

Specific dosages of the anti-CTLA4 antibody or antibody fragment of the present invention that may be administered for the prevention or treatment of a disease in a subject may be about 0.3, 0.6, 1.2, 18, 2.4, 3.0, 3.6, 4.2, 4.8, 5.4, 6.0, 6.6, 7.2, 7.8, 8.4, 9.0, 9.6 or 10.2 mg of antibody or antibody fragment/kg bodyweight of the patient. In certain embodiments, the dosage may be in a range of 0.3-2.4, 2.4-4.2, 4.2-6.0, 6.0-7.8, 7.8-10.2, 10.2-12, 12-14, 14-16, 16-18 or 18-20 mg of antibody or antibody fragment/kg bodyweight of the patient. The dosage of the antibody or antibody fragment will remain the same if administered in the form of a bispecific antibody, in combination with another immune checkpoint inhibitor or another antibody or antibody fragment or as an immunoconjugate. Further, a polypeptide having anti-CTLA4 activity will be administered in the same amounts as the antibody or antibody fragment.

A single dose of pharmaceutical formulation of the present invention may contain an amount of the anti-CTLA4 antibody or antibody fragment of the present invention of from about 45 µg of antibody or antibody fragment from about 13,600 mg, or from about 45 µg of antibody or antibody fragment from about 5440 mg. In some embodiments, a single dose of pharmaceutical formulation of the present invention may contain an amount of the anti-CTLA4 antibody or antibody fragment of the present invention of from to 135 mg to 1,387 mg, or an amount such as 135, 235, 335, 435, 535, 635, 735, 835, 935, 1035, 1135, 1235, 1387 mg. In certain embodiments, the amount of the anti-CTLA4 antibody or antibody fragment of the present invention in a single dose of the pharmaceutical formulation is in the range of 135-235, 235-335, 335-435, 435-535, 535-635, 635-735, 735-835, 835-935, 935-1035, 1035-1135, 1135-1235, 1235-1387 mg. The amount of the antibody or antibody fragment in the single dose of the pharmaceutical formulation will remain the same if administered in the form of a bispecific antibody, in combination with another immune checkpoint inhibitor or as an immunoconjugate, or in combination with another antibody or antibody fragment against another antigen as disclosed herein. Further, a polypeptide having anti-CTLA4 activity will be included in the single dose of the pharmaceutical formulation in the same amounts as the antibody or antibody fragment.

In one example, the anti-CTLA4 antibody or antibody fragment may be conjugated to another immune checkpoint inhibitor molecule or may form part of a bispecific antibody with another immune checkpoint inhibitor.

The other immune checkpoint inhibitor molecule may be an antibody or antibody fragment against another immune checkpoint besides CTLA4. The combination can be the anti-CTLA4 antibody or antibody fragment disclosed in this application and the another immune checkpoint inhibitor molecule administered as separate molecules or as a bispecific antibody. Such a bispecific antibody has a binding activity to CTLA4 and a second binding activity to the another immune checkpoint.

The immune checkpoint may be selected from LAG3, TIM3, TIGIT, VISTA, BTLA, OX40, CD40, 4-1BB, PD-1, PD-L1, and GITR (Zahavi and Weiner, *International Journal of Molecular Sciences*, vol. 20, 158, 2019). Additional immune checkppoints include B7-H3, B7-H4, KIR, A2aR, CD27, CD70, DR3, and ICOS (Manni et al., Immune checkpoint blockade and its combination therapy with small-molecule inhibitors for cancer treatment, Bbacan, https://doi.org/10.1016/j.bbcan.2018.12.002, 2018).

The immune checkpoint is preferably PD-1 or PD-L1.

It is understood that any of the above formulations or therapeutic methods may be carried out using an antibody fragment or an immunoconjugate of the invention in place of or in addition to an anti-CTLA4 antibody.

Enhancing the host's immune function to combat tumors is the subject of increasing interest. Conventional methods include (i) APC enhancement, such as (a) injection into the tumor of DNA encoding foreign MHC alloantigens, or (b)

transfecting biopsied tumor cells with genes that increase the probability of immune antigen recognition (e.g., immune stimulatory cytokines, GM-CSF, co-stimulatory molecules B7.1, B7.2) of the tumor, (iii) adoptive cellular immuno-therapy, or treatment with activated tumor-specific T-cells. Adoptive cellular immunotherapy includes isolating tumor-infiltrating host T-lymphocytes, expanding the population in vitro, such as through stimulation by IL-2 or tumor or both. Additionally, isolated T-cells that are dysfunctional may be also be activated by in vitro application of the anti-PD-L1 antibodies of the invention. T-cells that are so-activated may then be readministered to the host. One or more of these methods may be used in combination with administration of the antibody, antibody fragment or immunoconjugate of the present invention.

Traditional therapies for cancer include the following: (i) radiation therapy (e.g., radiotherapy, X-ray therapy, irradia-tion) or the use of ionizing radiation to kill cancer cells and shrink tumors. Radiation therapy can be administered either externally via external beam radiotherapy (EBRT) or inter-nally via brachytherapy; (ii) chemotherapy, or the applica-tion of cytotoxic drug which generally affect rapidly divid-ing cells; (iii) targeted therapies, or agents which specifically affect the deregulated proteins of cancer cells (e.g., tyrosine kinase inhibitors imatinib, gefitinib; monoclonal antibodies, photodynamic therapy); (iv) immunotherapy, or enhance-ment of the host's immune response (e.g., vaccine); (v) hormonal therapy, or blockade of hormone (e.g., when tumor is hormone sensitive), (vi) angiogenesis inhibitor, or blockade of blood vessel formation and growth, and (vii) palliative care, or treatment directed to improving the qual-ity of care to reduce pain, nausea, vomiting, diarrhea and hemorrhage. Pain medication such as morphine and oxyco-done, anti-emetics such as ondansetron and aprepitant, can permit more aggressive treatment regimens.

In the treatment of cancer, any of the previously described conventional treatments for the treatment of cancer immu-nity may be conducted, prior, subsequent or simultaneous with the administration of the anti-CTLA4 antibodies or antibody fragments. Additionally, the anti-CTLA4 antibod-ies or antibody fragments may be administered prior, sub-sequent or simultaneous with conventional cancer treat-ments, such as the administration of tumor-binding antibodies (e.g., monoclonal antibodies, toxin-conjugated monoclonal antibodies) and/or the administration of chemo-therapeutic agents.

F. Articles of Manufacture and Kits

In another aspect of the invention, an article of manufac-ture containing an anti-CTLA4 antibody or antibody frag-ment and other materials useful for the treatment, prevention and/or diagnosis of the disorders described above is pro-vided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierce-able by a hypodermic injection needle). At least one active agent in the composition is an antibody or antibody fragment of the invention. The label or package insert indicates that the composition is used for treating the condition of choice. Moreover, the article of manufacture may comprise (a) a first container with a composition contained therein, wherein the composition comprises an antibody or antibody fragment; and (b) a second container with a composition contained therein, wherein the composition comprises a further cyto-toxic or otherwise therapeutic agent. The article of manu-facture in this embodiment of the invention may further comprise a package insert indicating that the compositions can be used to treat a particular condition. Alternatively, or additionally, the article of manufacture may further com-prise a second (or third) container comprising a pharmaceu-tically-acceptable buffer, such as bacteriostatic water for injection (BWFI), phosphate-buffered saline, Ringer's solu-tion and dextrose solution. It may further include other materials desirable from a commercial and user standpoint, including other buffers, diluents, filters, needles, and syringes.

It is understood that any of the above articles of manu-facture may include an immunoconjugate of the invention in place of or in addition to an anti-CTLA4 antibody or antibody fragment.

Finally, the invention also provides kits comprising at least one antibody or antibody fragment of the invention. Kits containing polypeptide, antibodies or antibody frag-ments, or antibody drug conjugate of the invention find use in detecting CTLA4 expression (increase or decrease), or in therapeutic or diagnostic assays. Kits of the invention can contain an antibody coupled to a solid support, e.g., a tissue culture plate or beads (e.g., sepharose beads). Kits can be provided which contain antibodies for detection and quan-tification of CTLA4 in vitro, e.g. in an ELISA or a Western blot. Such antibody useful for detection may be provided with a label such as a fluorescent or radiolabel.

The kits further contain instructions on the use thereof. In some embodiments, the instructions comprise instructions required by the U.S. Food and Drug Administration for in vitro diagnostic kits. In some embodiments, the kits further comprise instructions for diagnosing the presence or absence of cerebrospinal fluid in a sample based on the presence or absence of CTLA4 in said sample. In some embodiments, the kits comprise one or more antibodies or antibody frag-ments. In other embodiments, the kits further comprise one or more enzymes, enzyme inhibitors or enzyme activators. In still other embodiments, the kits further comprise one or more chromatographic compounds. In yet other embodi-ments, the kits further comprise one or more compounds used to prepare the sample for spectroscopic assay. In further embodiments, the kits further comprise comparative refer-ence material to interpret the presence or absence of CTLA4 according to intensity, color spectrum, or other physical attribute of an indicator.

The following examples are illustrative, but not limiting, of the soft gelatin capsules of the present disclosure. Other suitable modifications and adaptations of the variety of conditions and parameters normally encountered in the field, and which are obvious to those skilled in the art, are within the scope of the disclosure.

EXAMPLES

Example 1: Conditionally Active Biological (CAB) Antibodies Against CTLA4

Antibodies against CTLA4 were produced in this Example (Table 2).

TABLE 2

| Conditionally active antibodies against CTLA4 | | |
| --- | --- | --- |
| CTLA4 Antibody | Light Chain Variable Region | Heavy Chain Variable Region |
| BA-087-05-19 | SEQ ID NO: 7 | SEQ ID NO: 8 |
| BA-087-08-32 | SEQ ID NO: 9 | SEQ ID NO: 10 |
| BA-087-01-07 | SEQ ID NO: 11 | SEQ ID NO: 12 |
| BA-087-01-09 | SEQ ID NO: 13 | SEQ ID NO: 14 |
| BA-087-03-03 | SEQ ID NO: 15 | SEQ ID NO: 16 |
| BA-087-03-04 | SEQ ID NO: 17 | SEQ ID NO: 18 |
| BA-087-04-04 | SEQ ID NO: 19 | SEQ ID NO: 20 |
| BA-087-04-07 | SEQ ID NO: 21 | SEQ ID NO: 22 |
| BA-087-05-02 | SEQ ID NO: 23 | SEQ ID NO: 24 |
| BA-087-06-11 | SEQ ID NO: 25 | SEQ ID NO: 26 |
| BA-087-08-09 | SEQ ID NO: 27 | SEQ ID NO: 28 |
| BA-087-09-01-03 | SEQ ID NO: 29 | SEQ ID NO: 30 |
| BA-087-09-01-02 | SEQ ID NO: 31 | SEQ ID NO: 32 |
| BA-087-09-01-06 | SEQ ID NO: 33 | SEQ ID NO: 34 |
| BA-087-09-02-02 | SEQ ID NO: 35 | SEQ ID NO: 36 |
| BA-087-09-02-06 | SEQ ID NO: 37 | SEQ ID NO: 38 |

These anti-CTLA4 antibodies were further characterized. Data for the antibodies BA-087-05-19 and BA-087-08-32 is presented in this application.

Example 2: ELISA Assay for Binding Activity of Anti-CTLA4 Antibodies

The binding activity of BA-087-05-19 and BA-087-08-32 to immobilized recombinant human CTLA4 was determined using an enzyme linked immunosorbent assay (ELISA) in pH 6.0 buffer (tumor microenvironment pH) or in pH 7.4 buffer (normal physiological pH). Serially diluted BA-087-05-19 and BA-087-08-32 were bound to recombinant human CTLA4 extracellular domain immobilized in the wells. The amount of bound BA-087-05-19 and BA-087-08-32 was quantified using anti-human IgG antibody conjugated to horseradish peroxidase (HRP), which then reacted with 3,3',5,5' tetramethylbenzidine (TMB) colorimetric substrate to generate a colored product. The OD absorbance in each well was proportional to the amount of BA-087-05-19 and BA-087-08-32 bound. $EC_{50}$ values at pH 6.0 for binding to human CTLA4 were calculated using the nonlinear fit model (variable slope, four parameters) of GraphPad Prism version 7.03.

Figure 3B:
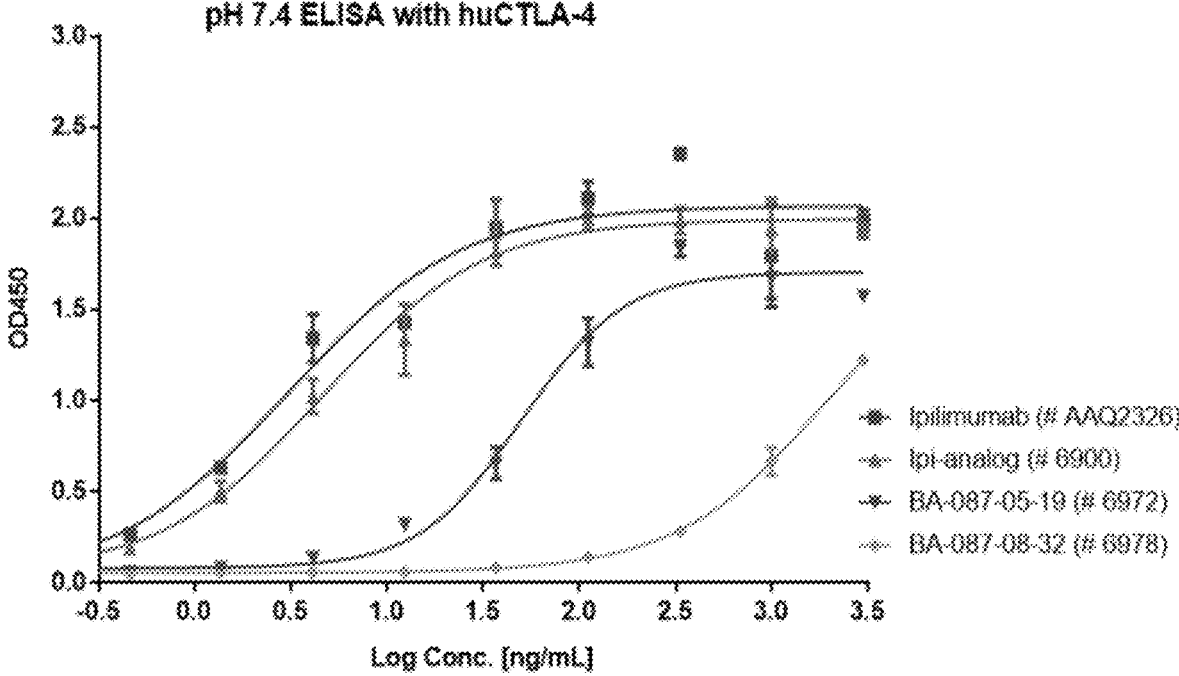
FIG. 3B shows a comparison of the binding activity to human CTLA4 at pH 7.4 of the two anti-CTLA4 antibodies of the present invention of FIG. 3A to Ipilimumab and an Ipilimumab analog (Ipi-analog) as measured by ELISA.

$EC_{50}$ values of the binding activity of BA-087-05-19 and BA-087-08-32 to human CTLA4 at pH 6.0 and pH 7.4 is shown in Tables 3-4 and the binding curves for representative experiments are shown in FIGS. 3A-3B. Both BA-087-05-19 and BA-087-08-32, show similar binding activities at pH 6.0 and significantly decreased binding activities at pH 7.4 to human CTLA4 when compared to Ipilimumab and an Ipilimumab analogue.

TABLE 3

| Binding activity of BA-087-05-19 and BA-087-08-32 to human CTLA4 at pH 6.0 | | | | |
| --- | --- | --- | --- | --- |
| | Method pH 6.0 ELISA Antigen huCTLA-4 | | | |
| Test Article | Ipilimumab (# AAQ2326) | Ipi-analog (#6900) | BA-087-05-19 (# 6972) | BA-067-08-32 (# 6978) |
| EC50 (ng/mL) Jun. 27, 2017 | 10.68 | 13.04 | 9.59 | 14.59 |
| EC50 (ng/mL) Jun. 29, 2017 | 5.85 | 6.10 | 6.59 | 8.57 |
| EC50 (ng/mL) Jul. 11, 2017 | 5.10 | 5.26 | 8.35 | 6.17 |
| EC50 (ng/mL) mean +/− SD | 7.21 +/− 3.03 | 8.13 +/− 4.27 | 8.18 +/− 1.51 | 9.78 +/− 4.34 |

TABLE 4

| Binding activity of BA-087-05-19 and BA-087-08-32 to human CTLA4 at pH 7.0 | | | | |
| --- | --- | --- | --- | --- |
| | Method pH 7.0 ELISA Antigen huCTLA-4 | | | |
| Test Article | Ipilimumab (# AAQ2326) | Ipi-analog (#6900) | BA-087-05-19 (# 6972) | BA-067-08-32 (# 6978) |
| EC50 (ng/mL) Jun. 27, 2017 | 11.16 | 10.95 | 35.82 | not calculated |
| EC50 (ng/mL) Jun. 29, 2017 | 3.71 | 3.67 | 93.37 | not calculated |
| EC50 (ng/mL) Jul. 11, 2017 | 3.08 | 3.08 | 50.18 | not calculated |
| EC50 (ng/mL) mean +/− SD | 5.98 +/− 4.49 | 6.41 +/− 3.96 | 59.79 +/− 29.95 | not calculated |

Figure 4A:
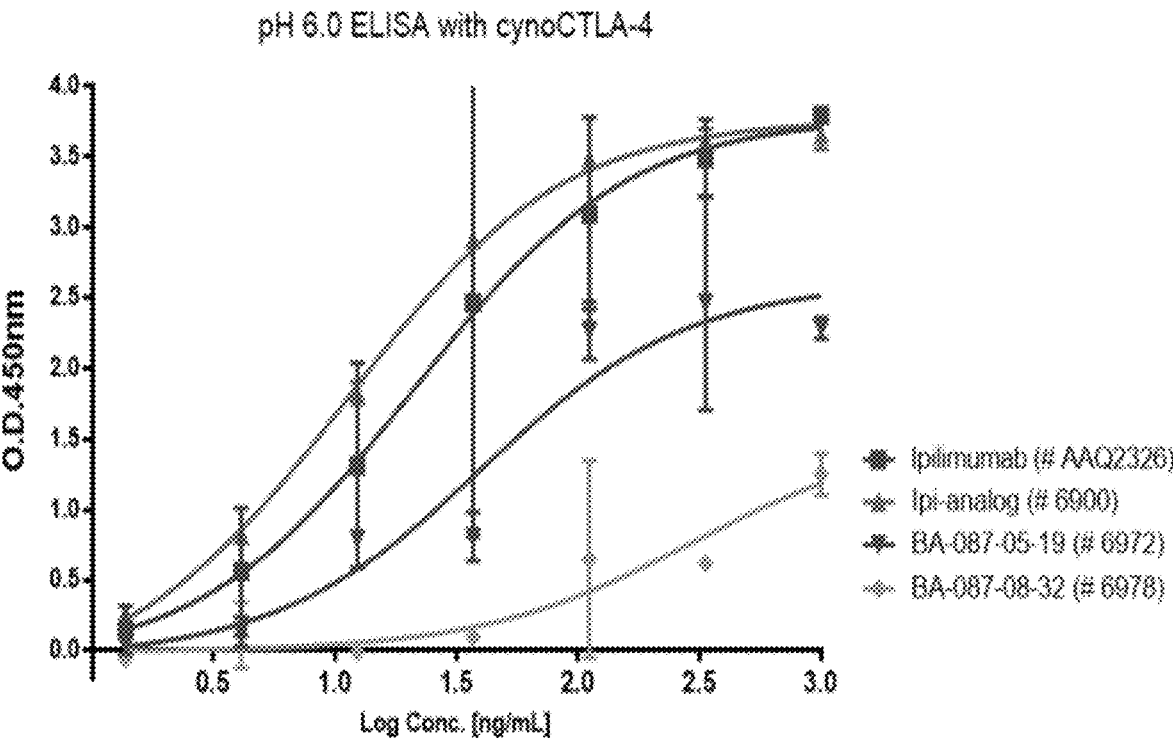
FIG. 4A shows a comparison of the binding activity to cynomolgus CTLA4 at pH 6.0 of the two anti-CTLA4 antibodies of the present invention of FIG. 3A to Ipilimumab and an Ipilimumab analog (Ipi-analog) as measured by ELISA.
Figure 4B:
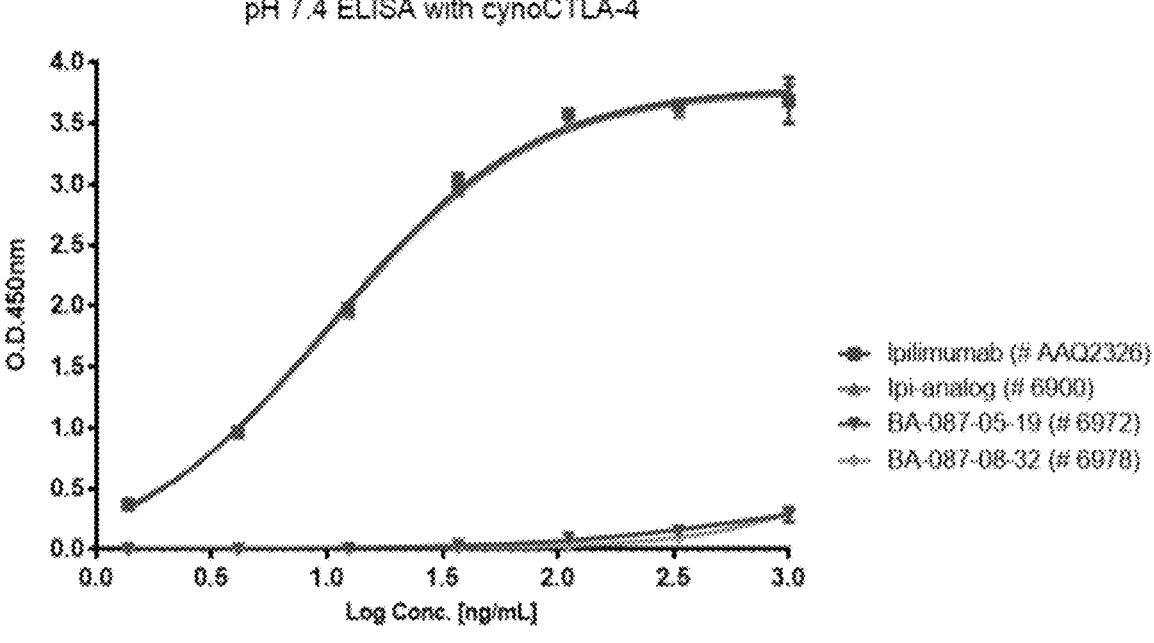
FIG. 4B shows a comparison of the binding activity to cynomolgus CTLA4 at pH 7.4 of the two anti-CTLA4 antibodies of the present invention of FIG. 3A to Ipilimumab and an Ipilimumab analog (Ipi-analog) as measured by ELISA.

In addition, the binding activity of BA-087-05-19 and BA-087-08-32 to immobilized recombinant cynomolgus CTLA4 extracellular domain was also determined by ELISA. The $EC_{50}$ of the binding activity of BA-087-05-19 and BA-087-08-32 to cynomolgus CTLA4 in pH 6.0 is shown in Table 5. The binding activity of BA-087-05-19 and BA-087-08-32 to cynomolgus CTLA4 at pH 6.0 and pH 7.4 is shown in FIGS. 4A-4B.

TABLE 5

| Binding activity of BA-087-05-19 and BA-087-08-32 to cynomolgus CTLA4 at pH 6.0 | | | | |
|---|---|---|---|---|
| | Method pH 6.0 ELISA Antigen cynoCTLA-4 | | | |
| Test Article | Ipilimumab (# AAQ2326) | Ipi-analog (#6900) | BA-087-05-19 (# 6972) | BA-067-08-32 (# 6978) |
| EC50 (ng/mL) Jun. 19, 2017 | 9.66 | 11.06 | 15.89 | 258.60 |
| EC50 (ng/mL) Jun. 27, 2017 | 20.99 | 11.17 | 39.72 | 292.10 |
| EC50 (ng/mL) mean +/− SD | 16.34 +/− 7.99 | 11.12 +/− 0.08 | 27.58 +/− 16.53 | 275.45 +/− 19.23 |

The $EC_{50}$ of the binding activity of BA-087-05-19 and BA-087-08-32 at a tumor microenvironment pH of 6.0, measured by ELISA were found to be 8.18 ng/mL and 9.78 ng/ml, respectively, for human CTLA4, similar to the $EC_{50}$ determined for Ipiliumab and Ipilimumab analogue. BA-087-05-19 has similar binding activity to both human and cynomolgus CTLA4 at pH 6.0, while BA-087-08-32 has a decreased binding activity to cynomolgus CTLA4 compared to its binding activity to human CTLA4 at pH 6.0. The drop in the binding activity of BA-087-08-32 to cynomolgus CTLA4 at pH 6.0 seen in ELISA appears to be specific for the ELISA assay as the same drop was not observed using either SPR or FACS. The binding activity of BA-087-05-19 and BA-087-08-32 to either human or cynomolgus CTLA4 at a normal physiological pH of 7.4 measured by ELISA was significantly lower than the binding activities at pH 6.0.

Example 3: pH-Dependent Binding Activity of Anti-CTLA4 Antibodies

Binding activity of the antibodies against CTLA4 was tested using an ELISA assay at a range of pH's from 5.0 to 7.4. Recombinant human CTLA4 extracellular domain was immobilized in a range of pH buffers in wells (pH 5.0 to pH 7.4), mimicking tumor microenvironment pH (pH 5.5 to pH 6.7) and the normal physiological pH (pH 7.4) and the binding activity was measured using ELISA. The antibodies BA-087-05-19 and BA-087-08-32 were serially diluted and their binding activity to the recombinant human CTLA4 extracellular domain was measured. The amount of bound antibodies BA-087-05-19 and BA-087-08-32 was quantified using anti-human IgG antibody conjugated to horseradish peroxidase (HRP), which then reacted with 3,3',5,5'-Tetramethylbenzidine (TMB) colorimetric substrate to generate a colored product. The OD absorbance in each well was proportional to the amount of BA-087-05-19 and BA-087-08-32 bound.

The pH inflection point (=50% of the binding activity at pH 6.0) for BA-087-05-19 was calculated to be at pH 6.97 with 90% of the binding activity being present at pH 6.66. The pH inflection point (=50% to the binding activity at pH 6.0) for BA-087-08-32 was calculated to be at pH 6.43 with 90% of the binding activity being present at pH 6.2.

Average OD values (from 2 replicates) at the different pH's were plotted against the pH of the buffer using Softmax Pro software (Molecular Devices). Curve fitting was done using the 4-parameter model built into the software. The inflection point of the pH curve (=50% of the binding activity at pH 6.0) equals parameter C of the fitting equation. Binding activity at pH 6.0 was set to 100%. The pH for 90% binding activity was interpolated from the fitted curve using the "InterpX" function of the Softmax Pro software.

The average pH's for 50% and 90% activity for BA-087-05-19 and BA-087-08-32 were calculated using the pH values obtained in Experiments 1-4. BA-087-05-19 (lot numbers #6972) and BA-087-08-32 (lot number #6978) were used in Experiments 1-4. Other lots of BA-087-05-19 (lot number #6901) and BA-087-08-32 (lot number #6902) were used in Experiment 5. The pH's for 50% and 90% activity for BA-087-05-19 and BA-087-08-32 determined from the data of Experiment 5 was similar to the average pH values calculated using the pH values from Experiments 1-4. See Table 6.

TABLE 6

| pH Dependent Binding of BA-087-05-19 and BA-087-08-32 | | | | |
|---|---|---|---|---|
| | BA-087-05-19 | | BA-087-08-32 | |
| Antibodies | pH (90%) | pH (50%) | pH (90%) | pH (50%) |
| Experiment 1 (Jun. 28, 2017) | 6.76 | 704 | 6.39 | 6.55 |
| Experiment 2 (Jul. 06, 2017) | 6.55 | 6.99 | 6.18 | 6.37 |
| Experiment 3 (Jul. 11, 2017) | 6.51 | 6.83 | 6.17 | 6.33 |
| Experiment 4 (Jul. 11, 2017) | 6.81 | 7.02 | 6.18 | 6.48 |
| average ± SD | 6.66 ± 015 | 6.97 ± 0.10 | 6.23 ± 0.11 | 6.43 ± 0.10 |
| Experiment 5 (Jun. 20, 2017) | 6.34 | 6.68 | 6.2 | 6.36 |

Figure 5:
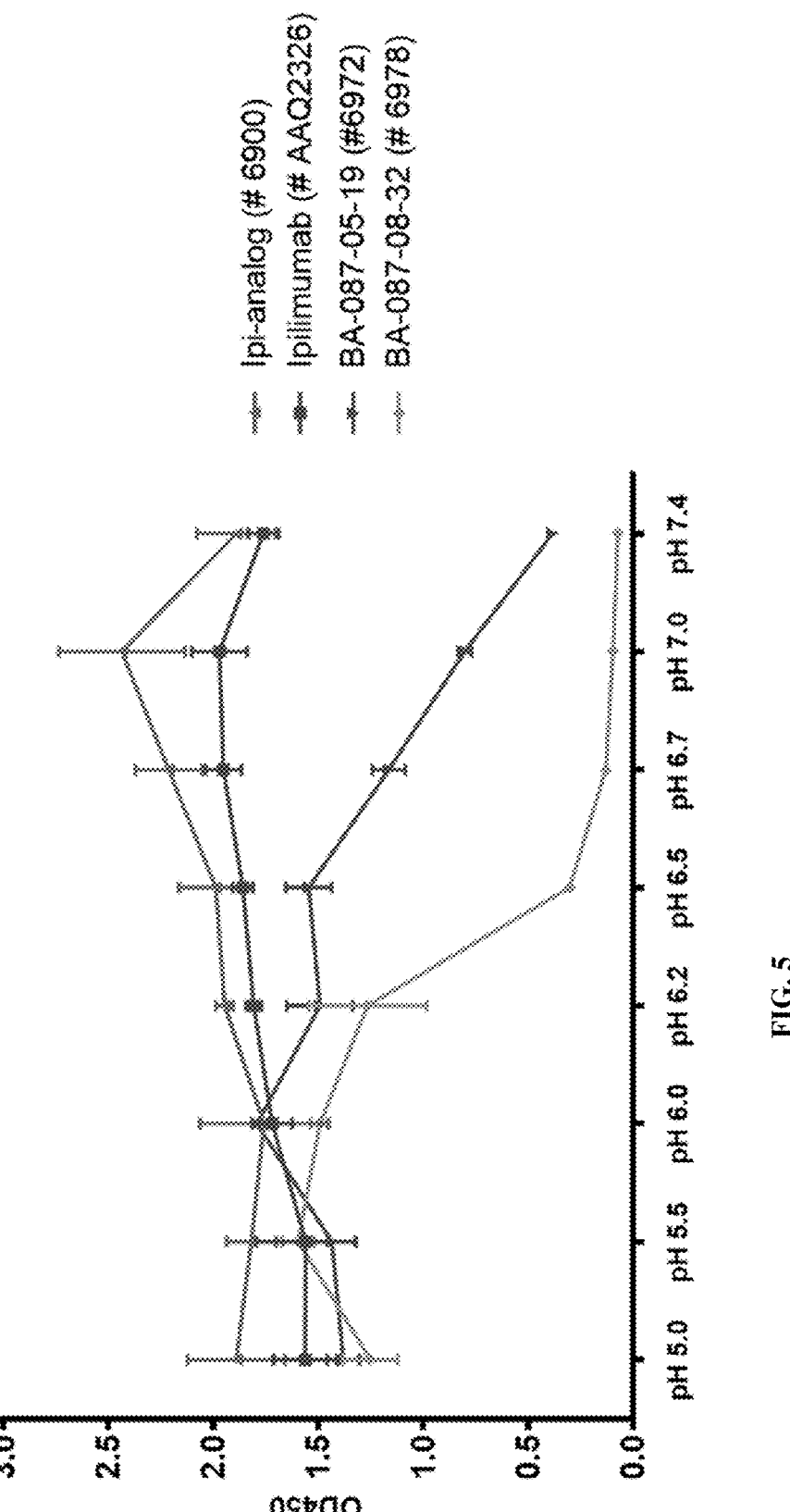
FIG. 5 shows a comparison of the pH-dependent binding activity to human CTLA4 of the two anti-CTLA4 antibodies of the present invention of FIG. 3A to Ipilimumab and an Ipilimumab analog (Ipi-analog).

The binding activities of BA-087-05-019 and BA-087-08-32, as well as positive controls Ipilimumab and Ipilimumab analogue, to recombinant human CTLA4 in various pH buffers are shown in FIG. 5. The inflection points of the pH dependent binding for BA-087-05-19 and BA-087-08-32 were calculated to be at pH 6.97 and pH 6.43, respectively. 90% of the binding activities for BA-087-05-19 and BA-087-08-32 were present at pH 6.34 and pH 6.2, respectively. In addition, weaker binding activities for both BA-087-05-19 and BA-087-08-32 were detected at a normal physiological pH of 7.4 (FIG. 5).

Example 4: Binding Kinetics of Anti-CTLA4 Antibodies

The binding kinetics of antibodies BA-087-05-19 and BA-087-08-32 were measured using surface plasmon resonance (SPR) on immobilized recombinant human or cynomolgus CTLA4 at pH 6.0 and pH 7.4. The CTLA4 extracellular domain (human or cynomolgus) was immobilized on the surface of a sensor chip. Different concentrations of BA-087-05-19 and BA-087-08-32 were injected and the binding interactions with the immobilized CTLA4 and a control surface were monitored in real time. The binding kinetics were calculated using a 1:1 Longmuir model built into the analysis software.

Antibody BA-087-05-19 showed sub-nanomolar binding activity at pH 6.0. The binding activity drops from pH 6.0 to pH 7.4 by about a factor of 2 ($K_D$ [pH 6.0]=0.5 nM; $K_D$ [pH 7.4]=1.1 nM). In addition to the lower binding activity at pH 7.4, the SPR signal at pH 7.4 reaches only about 20% of the signal level detected at pH 6.0 indicating that only a small fraction of the BA-087-05-19 that was present was able to bind to human CTLA4 at pH 7.4. See Table 7.

The binding activity of antibodies BA-087-05-19, BA-087-08-32, and Ipilimumab to cynomolgus CTLA4 were tested using the same conditions as described above for human CTLA4. All three antibodies have a fast off-rate and the SPR signal reaches equilibrium at all antibody concentrations tested. The $K_D$ was calculated by plotting the maximum SPR signal at each concentration against the antibody concentration. Experiments were run in triplicate at each pH.

TABLE 7

| Binding activity of BA-087-05-19 to human CTLA4 at different pH values | | | | | |
| --- | --- | --- | --- | --- | --- |
| pH 6.0 | | | pH 7.4 | | |
| Ka [M · s] | Kd [s$^{-1}$] | KD [M] | Ka [M · s] | Kd [s$^{-1}$] | KD [M] |
| 1.34E+06 | 6.31E−04 | 4.72E−10 | 9.06E+05 | 1.26E−03 | 1.39E−09 |
| 1.26E+06 | 6.04E−04 | 4.81E−10 | 8.57E+05 | 6.69E−04 | 7.81E−10 |
| 1.10E+06 | 5.98E−04 | 5.43E−10 | 8.44E+05 | 9.43E−04 | 1.12E−09 |
| AVG | | | AVG | | |
| 1.23E+06 | 6.11E−04 | 4.99E−10 | 8.69E+05 | 9.58E−04 | 1.10E−09 |

BA-087-08-32 also showed sub-nanomolar binding activity at pH 6.0. The binding activity drops from pH 6.0 to pH 7.4 by about a factor of 100 ($K_D$ [pH 6.0]=0.45 nM; $K_D$[pH 7.4]=45 nM). In addition to the lower binding activity at pH 7.4, the SPR signal at pH 7.4 reaches only about 10% of the signal level at pH 6.0 indicating that only a small fraction of the BA-087-08-32 present is able to bind to human CTLA4 at pH 7.4. See Table 8.

Antibody BA-087-05-19 binds to cynoCTLA4 with a $K_D$ of 1.96 nM at pH 6.0. At pH 7.4 the calculation indicates a $K_D$>100 nM. Antibody BA-087-08-32 binds to cynoCTLA4 with a $K_D$ of 5.95 nM at pH 6.0. At pH 7.4 the resulting SPR signal is too low to calculate a $K_D$. Antibody Ipilimumab binds to cynoCTLA4 with a $K_D$ of 6.58 nM at pH 6.0 and a $K_D$ of 6.80 nM at pH 7.4.

TABLE 8

| Binding activity of BA-087-08-32 to human CTLA4 at different pH | | | | | |
| --- | --- | --- | --- | --- | --- |
| pH 6.0 | | | pH 7.4 | | |
| Ka [M · s] | Kd [s$^{-1}$] | KD [M] | Ka [M · s] | Kd [s$^{-1}$] | KD [M] |
| 3.29E+06 | 1.20E−03 | 3.65E−10 | 5.04E+05 | 2.836E−02 | 5.25E−08 |
| 3.32E+06 | 1.54E−03 | 4.63E−10 | 8.59E+05 | 8.3E−03 | 1.49E−08 |
| 4.08E+06 | 2.14E−03 | 5.24E−10 | 1.94E+05 | 1.32E−02 | 6.83E−08 |
| AVG | | | AVG | | |
| 3.56E+06 | 1.63E−03 | 4.51E−10 | 5.19E+05 | 1.66E−02 | 4.52E−08 |

Commerically available anti-CTLA4 antibody Ipilimumab (Yervoy™) was used as control under the same conditions and the binding activity was found to be very similar at pH 6.0 and pH 7.4 ($K_D$ [pH 6.0]=1.39 nM; $K_D$ [pH 7.4]=1.37 nM). As such, the binding activity of the Ipilimumab did not depend on the pH. See Table 9. The resulting SPR signals are also very similar at both pH 6.0 and pH 7.4.

Example 5: FACS Analysis of Anti-CTLA4 Antibodies

The binding activities of antibodies BA-087-05-19 and BA-087-08-32 to human and cynomolgus CTLA4 expressed on the cell surface of CHO cells in a pH 6.0 buffer or in pH 7.4 buffer were measured by (FACS). Serially diluted

TABLE 9

| Binding activity of Ipilimumab to human CTLA4 at different pH | | | | | |
| --- | --- | --- | --- | --- | --- |
| pH 6.0 | | | pH 7.4 | | |
| Ka [M · s] | Kd [s$^{-1}$] | KD [M] | Ka [M · s] | Kd [s$^{-1}$] | KD [M] |
| 9.48E+05 | 1.39E−03 | 1.47E−09 | 1.12E+06 | 1.16E−03 | 1.04E−09 |
| 8.19E+05 | 9.47E−04 | 1.16E−09 | 1.13E+06 | 1.52E−03 | 1.35E−09 |
| 7.72E+05 | 1.19E−03 | 1.54E−09 | 1.17E+06 | 2.02E−03 | 1.72E−09 |
| AVG | | | AVG | | |
| 8.46E+05 | 1.17E−03 | 1.39E−09 | 1.14E+06 | 1.57E−03 | 1.37E−09 |

BA-087-05-19, BA-087-08-32, Ipilimumab and Ipilimumab analogue were added to the CHO cells expressing human or cynomolgus CTLA4. The amount of antibodies bound on the cells was quantified using anti-human IgG antibody conjugated to fluorophores. $EC_{50}$ values at pH 6.0 and 7.4 for binding to cells were calculated using the nonlinear fit (variable slope, four parameters) model built into GraphPad Prism software (version 7.03). The expression levels of human CTLA4 or cynomolgus CTLA4 on the surface of the CHO cells were determined using a BD QuantiBRITE™ PE kit.

Figure 6A:
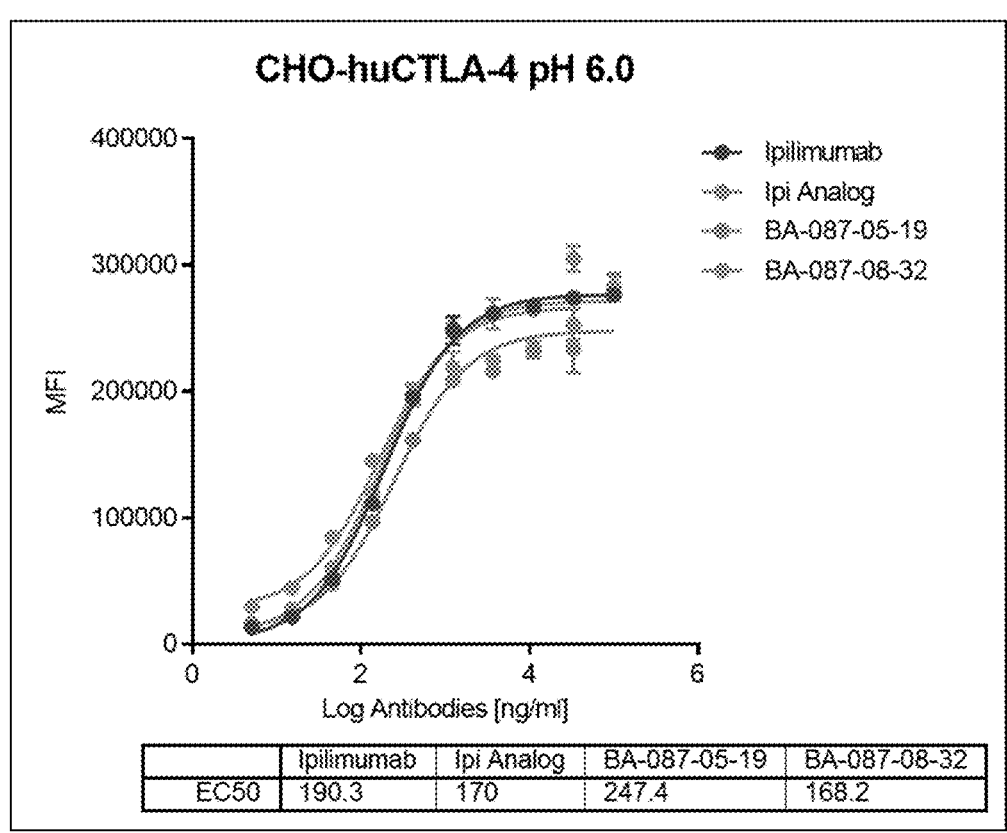
FIG. 6A shows a comparison of the half maximal effective concentration ($EC_{50}$) of, and the binding activity to human CTLA4 at pH 6.0 of the two anti-CTLA4 antibodies of the present invention of FIG. 3A to Ipilimumab and an Ipilimumab analog (Ipi-analog) as measured by fluorescence-activated cell sorting (FACS) using CHO cells.
Figure 6B:
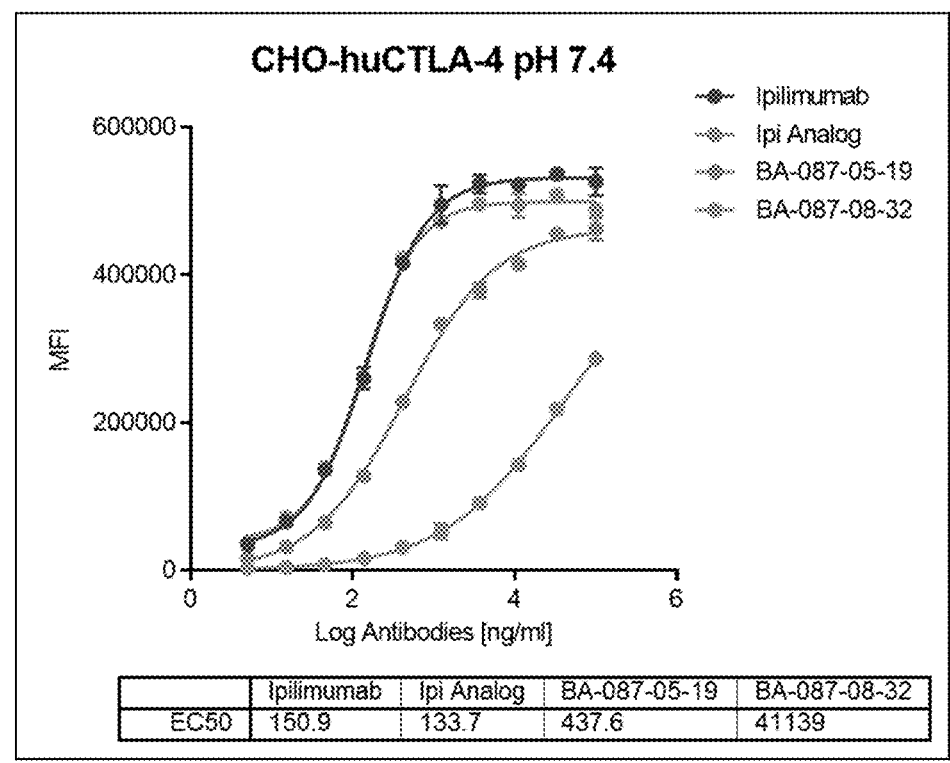
FIG. 6B shows a comparison of the ($EC_{50}$) of, and the binding activity to human CTLA4 at pH 7.4 of the two anti-CTLA4 antibodies of the present invention of FIG. 3A to Ipilimumab and an Ipilimumab analog (Ipi-analog) as measured by FACS using CHO cells.
Figure 7A:
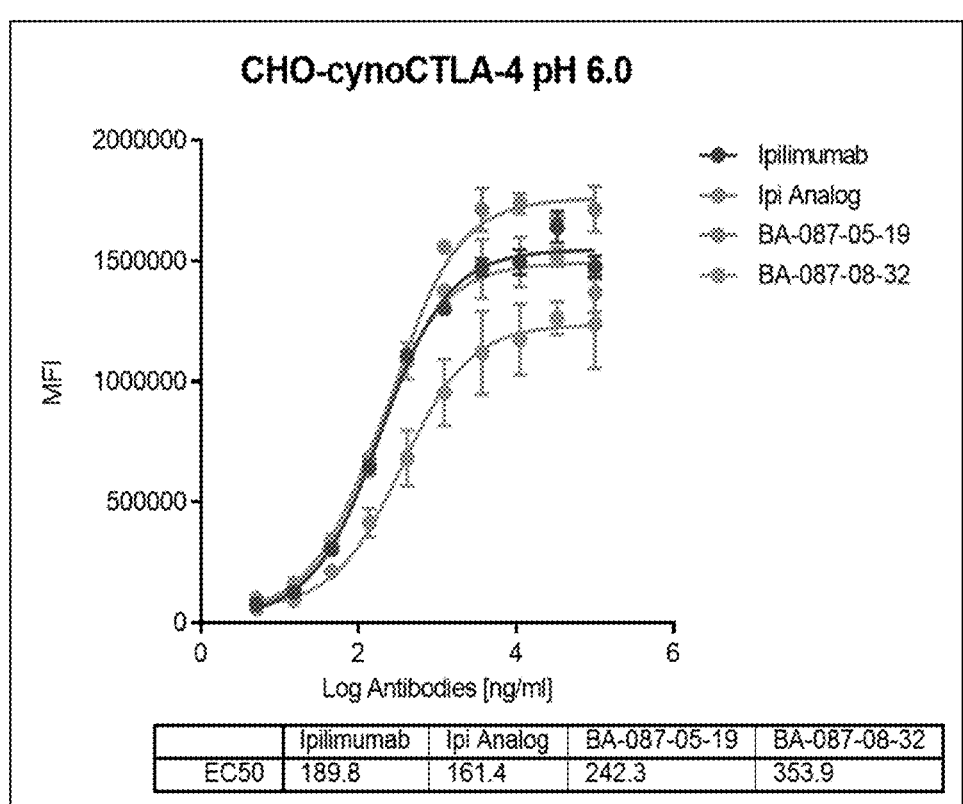
FIG. 7A shows a comparison of the ($EC_{50}$) of, and the binding activity to cynomolgus CTLA4 at pH 6.0 of the two anti-CTLA4 antibodies of the present invention of FIG. 3A to Ipilimumab and an Ipilimumab analog (Ipi-analog) as measured by fluorescence-activated cell sorting (FACS) using CHO cells.
Figure 7B:
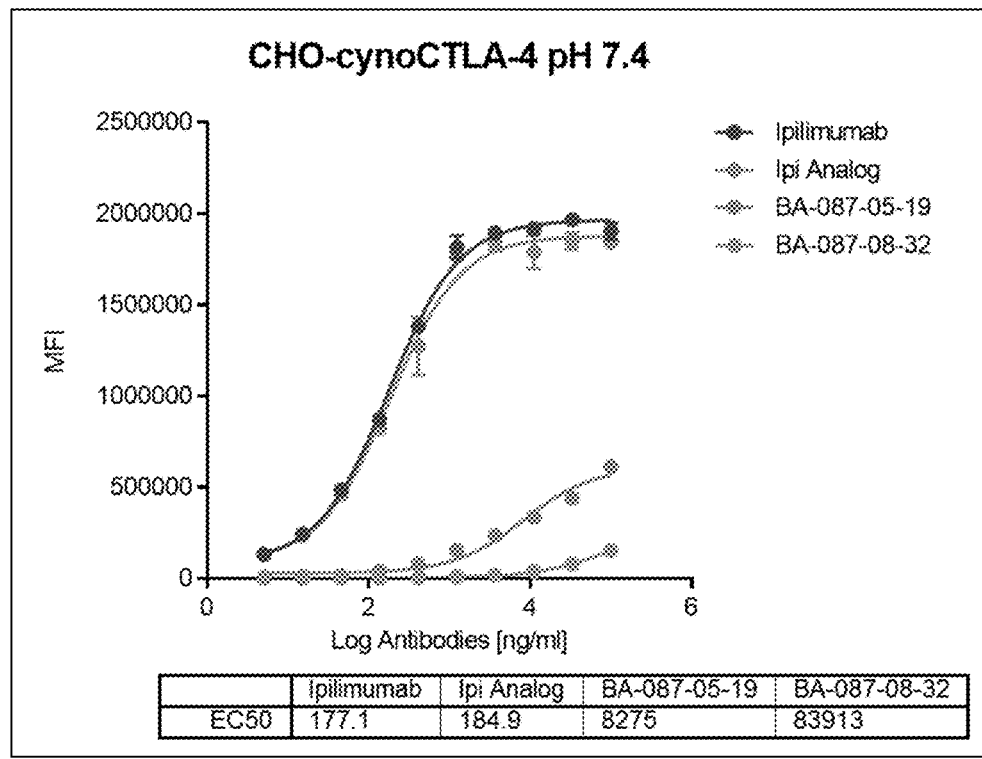
FIG. 7B shows a comparison of the ($EC_{50}$) of, and the binding activity to cynomolgus CTLA4 at pH 7.4 of the two anti-CTLA4 antibodies of the present invention of FIG. 3A to Ipilimumab and an Ipilimumab analog (Ipi-analog) as measured by FACS using CHO cells.

At least two independent duplicate FACS experiments were performed for each antibody using each of the cell lines. Binding activities of the antibodies to human CTLA4 on CHO cells (CHO-huCTLA4) at pH 6.0 and 7.4 are shown in FIGS. 6A-6B. Binding activities of the antibodies to cynomolgus CTLA4 on CHO cells (CHO-cynoCTLA4) at pH 6.0 and 7.4 are shown in FIGS. 7A-7B. The binding activities at different concentrations of the antibodies are plotted in these figures.

The binding activities of BA-087-05-19 and BA-087-08-32 at pH 6.0 measured by FACs were found to have mean $EC_{50}$'s of 350.1 and 243.4 ng/mL, respectively, for human CTLA4, and 316.2 ng/mL and 402.6 ng/mL, respectively, for cynomolgus CTLA4. The binding activities of Ipilimumab and Ipilimumab analogue at pH 6.0 measured by FACs were found to have mean $EC_{50}$'s of 341.1 and 325.4 ng/mL, respectively, for human CTLA4, and 337.5 ng/mL the antibodies BA-087-05-19 and BA-087-08-32 were bound on the CHO cells than was the case for the control Ipilimumab analogue.

Example 6: ELISA and FACS Analyses of Anti-CTLA4 Antibody Stability

The binding activities of antibodies BA-087-05-19 and BA-087-08-32 to human CTLA4 at pH 6.0 in buffer and at pH 7.4 in buffer, were measured using different buffers. Both ELISA and FACS analysis were used to measure the binding activity. In ELISA analysis, serially diluted BA-087-05-19 and BA-087-08-32 samples were added to human wells pre-coated with CTLA4 and the respective buffer. The amount of bound antibodies was quantified using anti-human IgG antibody conjugated to HRP. The absorbance at 450 nm in each measurement was proportional to the amount of antibodies bound. See ELISA data in FIGS. 9A-9F. EC50 value (in ng/mL) for binding to human CTLA4 was determined by absorbance at 450 nm against antibody concentration with Prism variable slope of four-parameter dose-response curve, which was calculated using the nonlinear fit (variable slope, four parameters) model built into GraphPad Prism software (version 7.03). The $EC_{50}$ values for binding to human CTLA4 as measured by ELISA in different buffers are given in Tables 10-11. The buffers tested included His buffer (His), Tris buffer (Tris), Glutamine buffer (Glu) and no buffer.

TABLE 10

| | BA-087-05-19 (6972 His) | | BA-087-05-19 (6972 Tris) | | BA-087-05-19 (6972 Glu) | | BA-087-05-19 (6972) | |
|---|---|---|---|---|---|---|---|---|
| EC50 (ng/mL) | pH 6.0 | pH 7.4 | pH 6.0 | pH 7.4 | pH 6.0 | pH 7.4 | pH 6.0 | pH 7.4 |
| T0 | 15.41 | 54.36 | 5.913 | 42.37 | 10.89 | 110.2 | 6.258 | 54.55 |
| T2W | 7.042 | 75.81 | 10.14 | 36.54 | 2.663 | 21.95 | 6.258 | 54.55 |

EC50 of BA-087-05-19 in different buffers determined by ELISA

TABLE 11

| | BA-087-08-32 (6978 His) | | BA-087-08-32 (6978 Tris) | | BA-087-08-32 (6978 Glu) | | BA-087-08-32 (6978) | |
|---|---|---|---|---|---|---|---|---|
| EC50 (ng/mL) | pH 6.0 | pH 7.4 | pH 6.0 | pH 7.4 | pH 6.0 | pH 7.4 | pH 6.0 | pH 7.4 |
| T0 | 37.99 | 490.8 | 17.06 | 1135 | 33.72 | 1189 | 22.23 | 1144 |
| T2W | 44.08 | 1075 | 13.99 | 1491 | 12.26 | 724 | 22.23 | 1144 |

EC50 of BA-087-08-32 in different buffers determined by ELISA and 319.6 ng/mL, respectively, for cynomolgus CTLA4. The binding activities of BA-087-05-19 and BA-087-08-32 at pH 7.4 were weaker than the binding activities at pH 6.0 even at the highest concentration tested.

Both BA-087-05-19 and BA-087-08-32 bind to human CTLA4 and cynomolgus CTLA4 with similar affinity as Ipilimumab and Ipilimumab analogue at pH 6.0. However, BA-087-05-19 and BA-087-08-32 each have a much weaker binding activity to human and cynomolgus CTLA4 at pH 7.4 when compared to the binding activities of Ipilimumab and Ipilimumab analogue at pH 7.4. No binding activity was detected for CHO cells that did not express CTLA4.

Figure 8A:
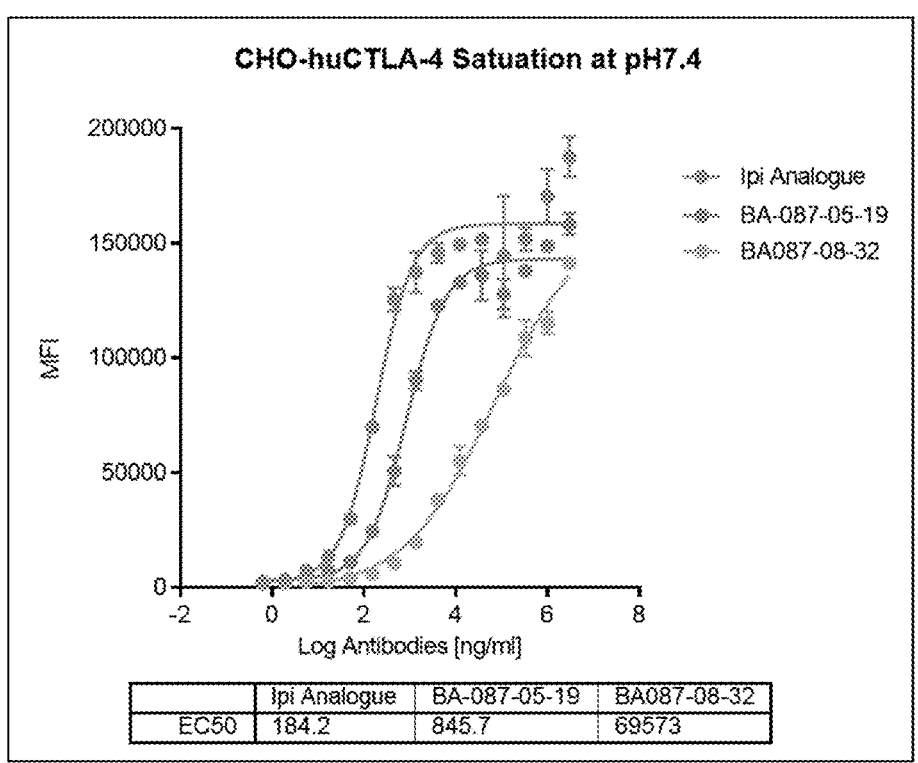
FIG. 8A shows a comparison of the ($EC_{50}$) of, and the saturation of human CTLA4 at pH 7.4 by the anti-CTLA4 antibodies of the present invention of FIG. 3A to the Ipi analog as measured by FACS.
Figure 8B:
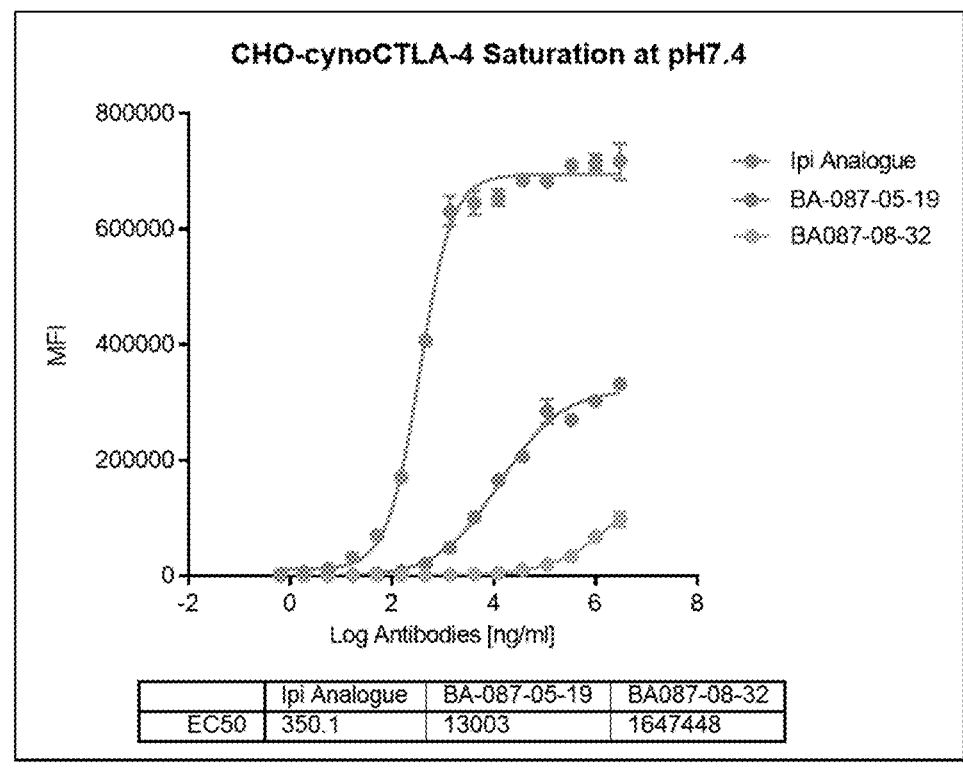
FIG. 8B shows a comparison of the ($EC_{50}$) of, and the saturation of cynomolgus CTLA4 at pH 7.4 by the anti-CTLA4 antibodies of the present invention of FIG. 3A to the Ipi analog as measured by FACS.
Figure 9A:
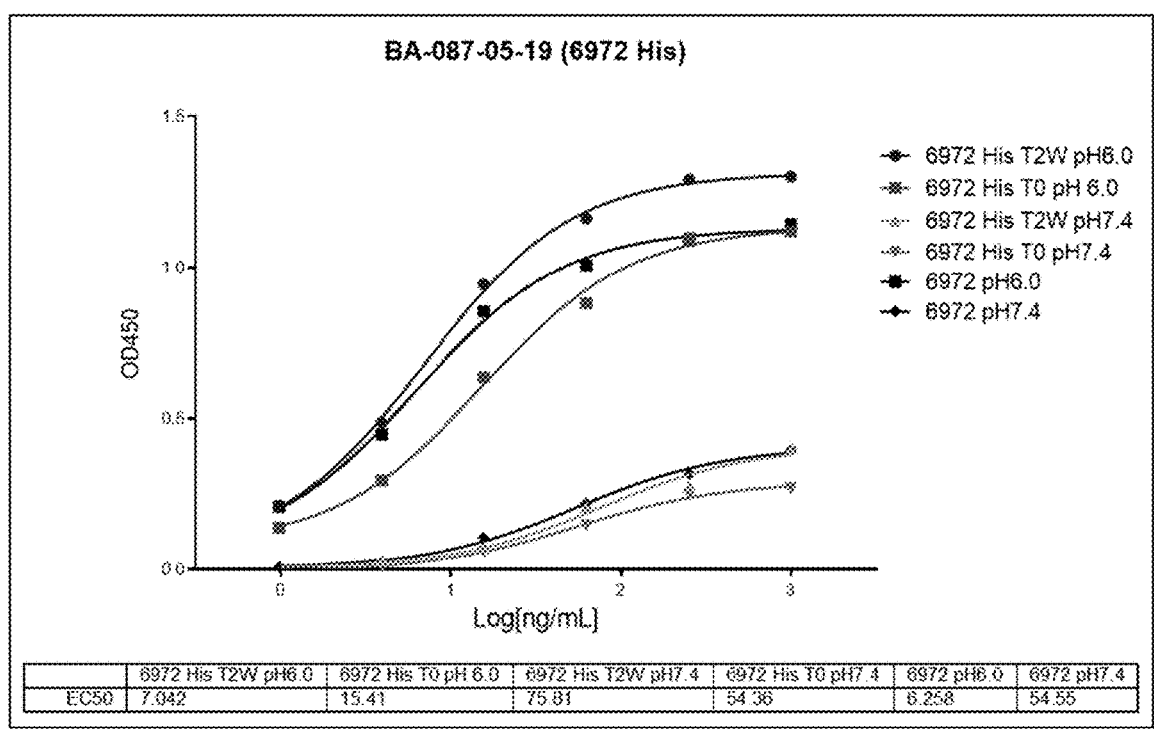
FIGS. 9A-9F show binding activity to human CTLA4 of the anti-CTLA4 antibodies of the present invention of FIG. 3A at pH 6.0 or pH 7.4 as well as at pH 6.0 or pH 7.4 in the presence of different buffers, as measured by ELISA.
Figure 9B:
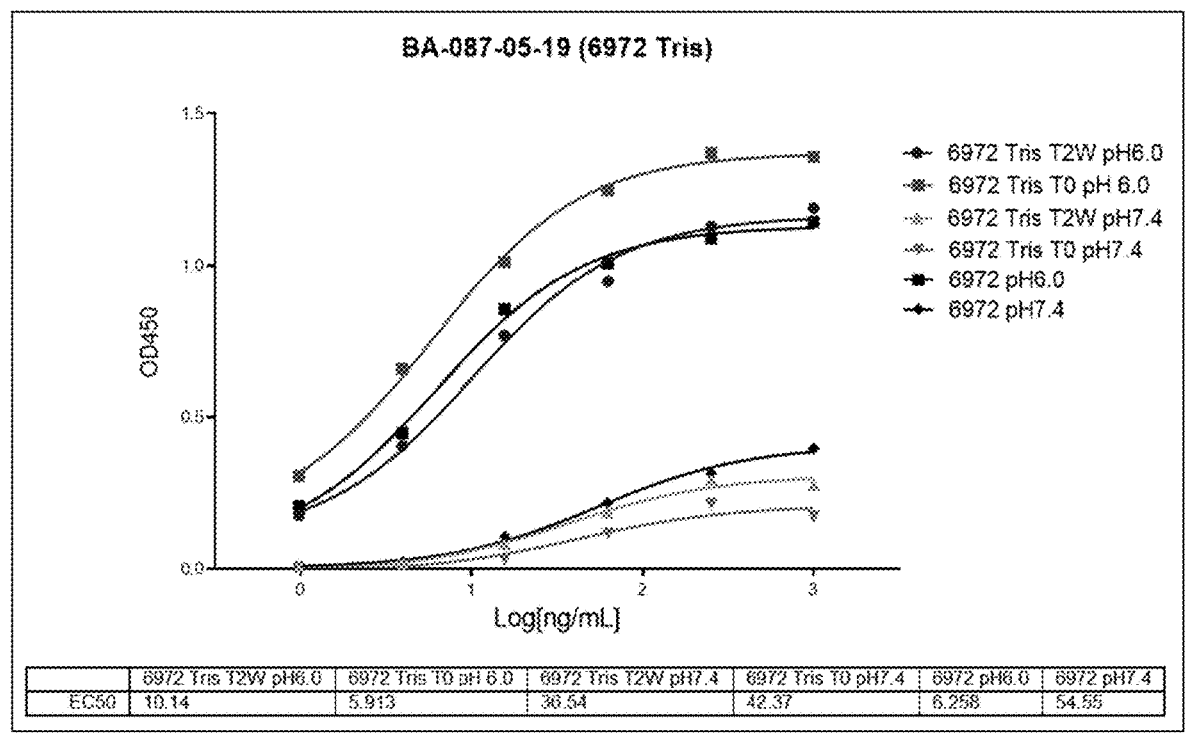
Figure 9C:
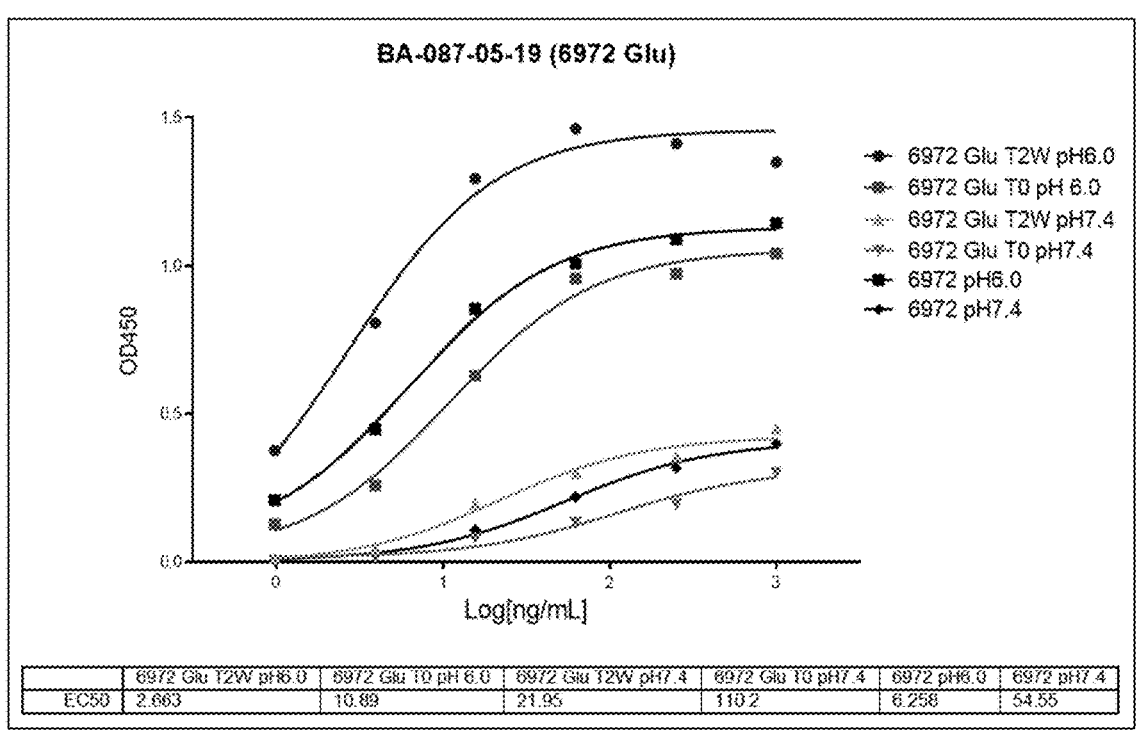
Figure 9D:
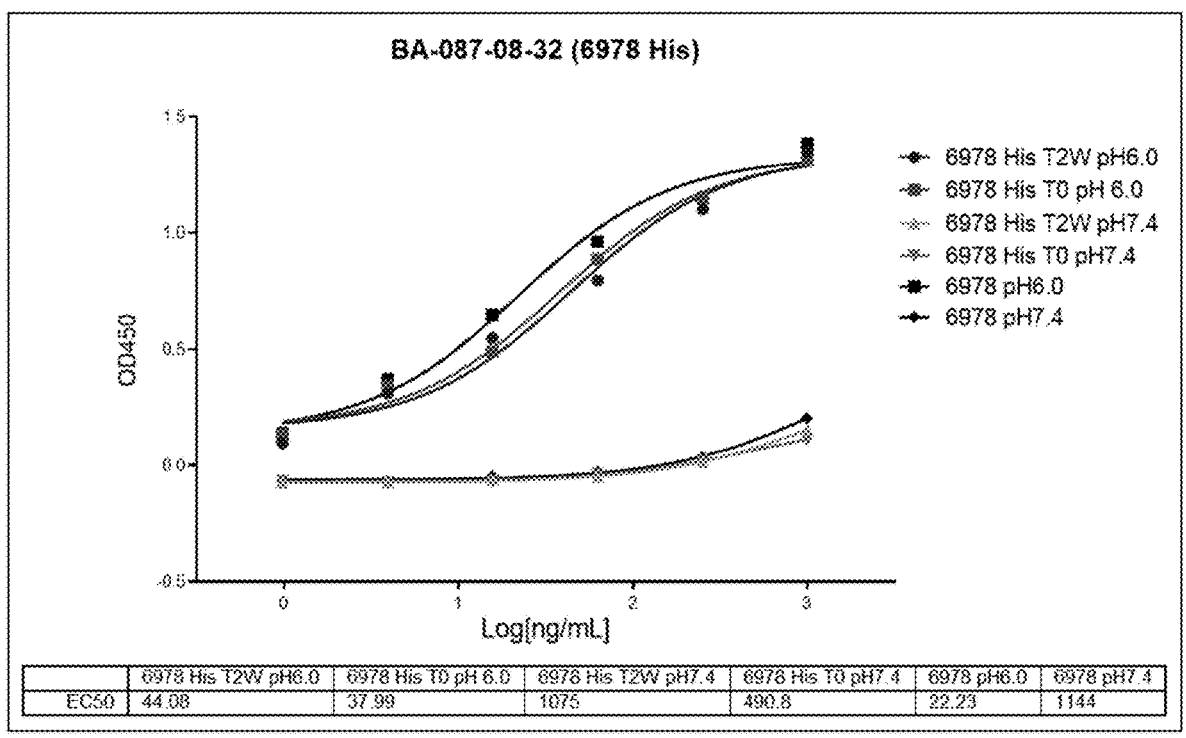
Figure 9E:
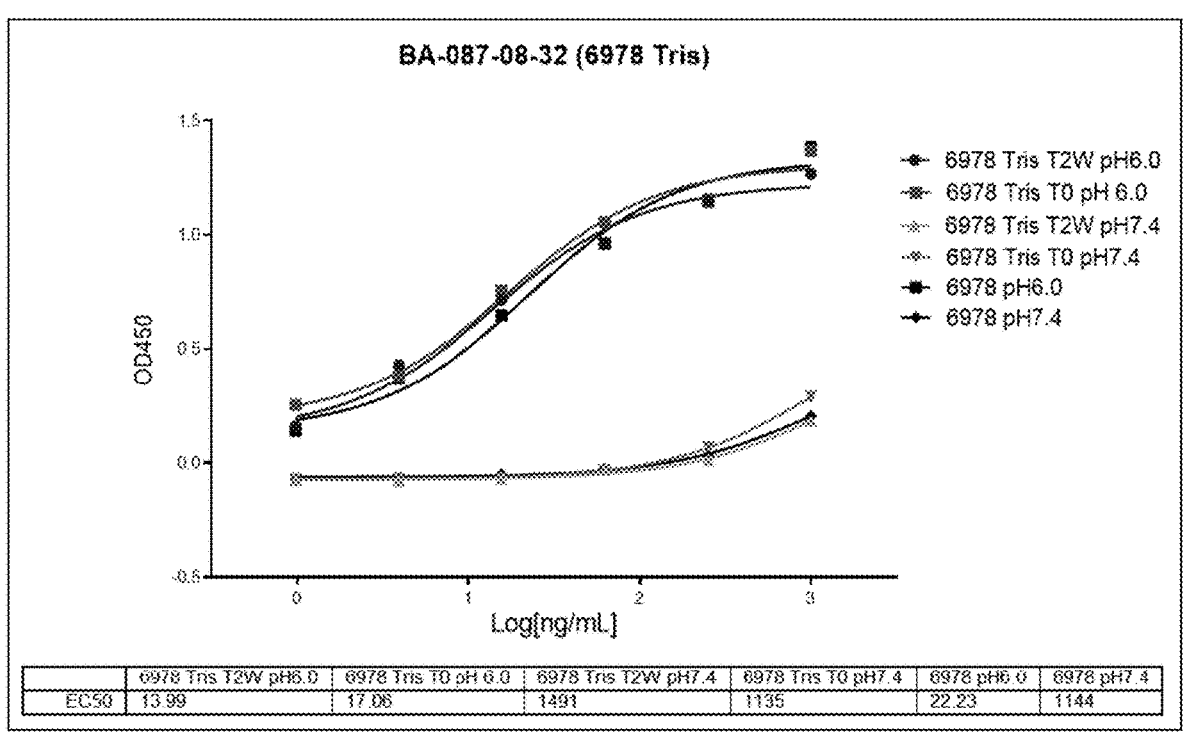
Figure 9F:
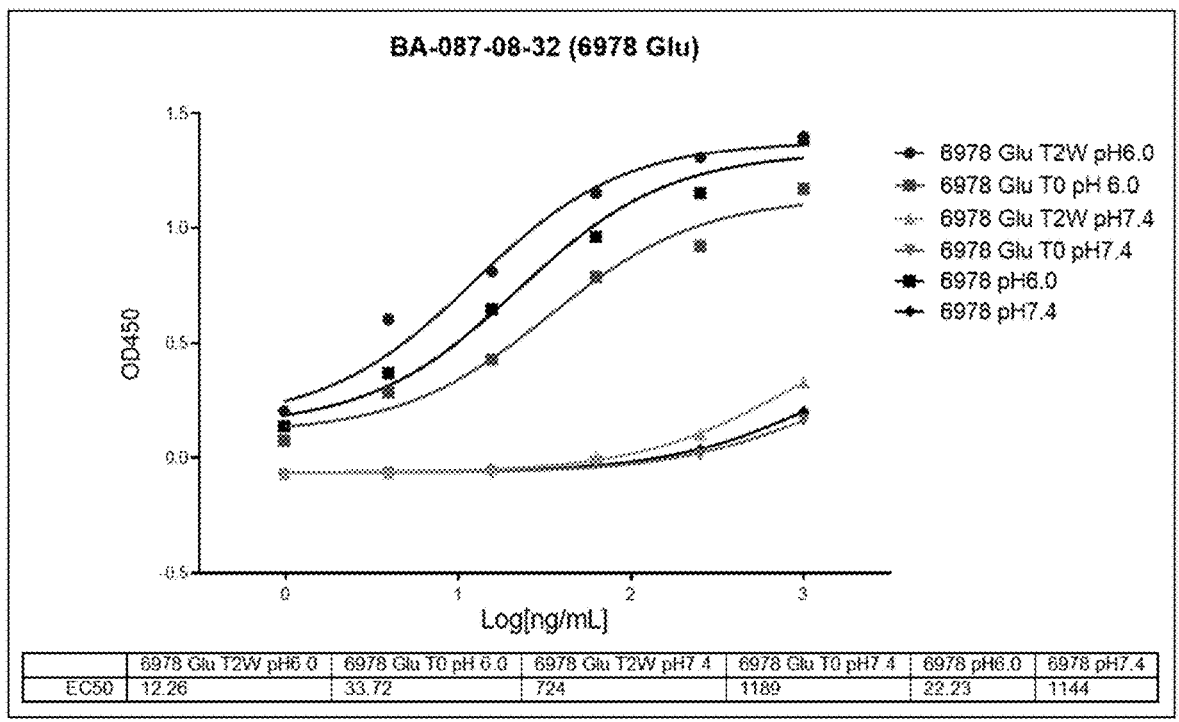
Figure 10A:
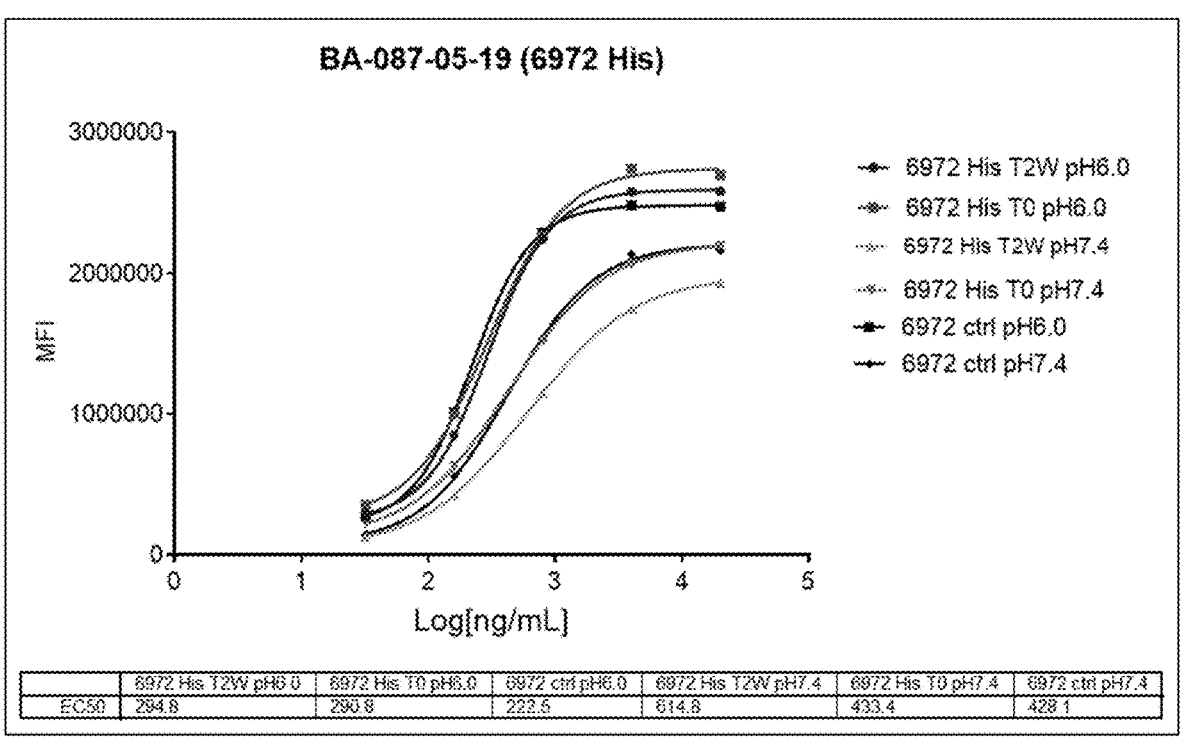
FIGS. 10A-10F show binding activity to human CTLA4 of the anti-CTLA4 antibodies of the present invention of FIG. 3A at pH 6.0 or pH 7.4 as well as at pH 6.0 or pH 7.4 in the presence of different buffers, as measured by FACS.
Figure 10B:
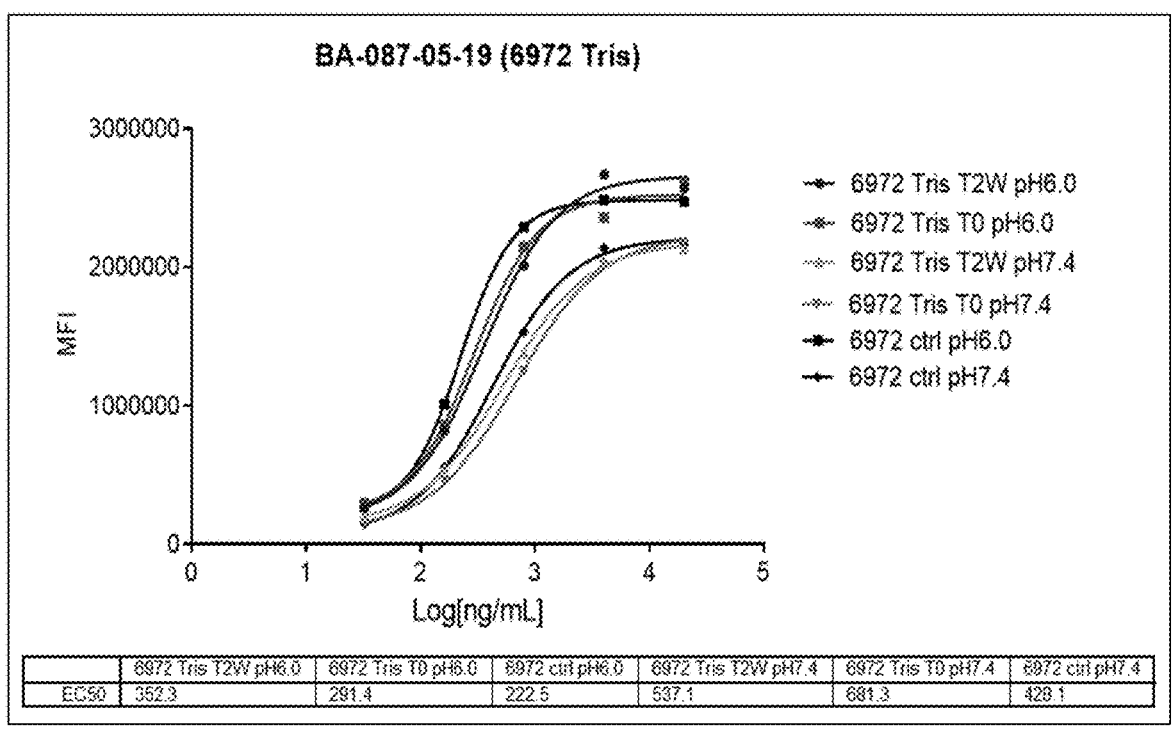
Figure 10C:
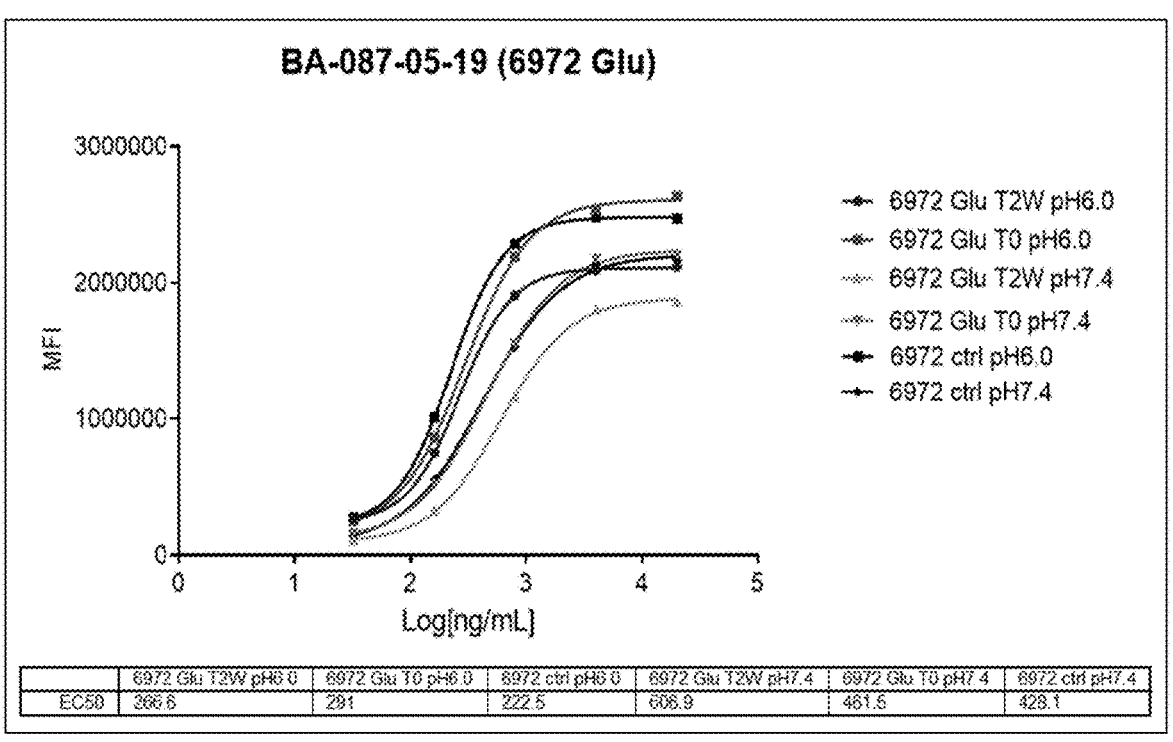
Figure 10D:
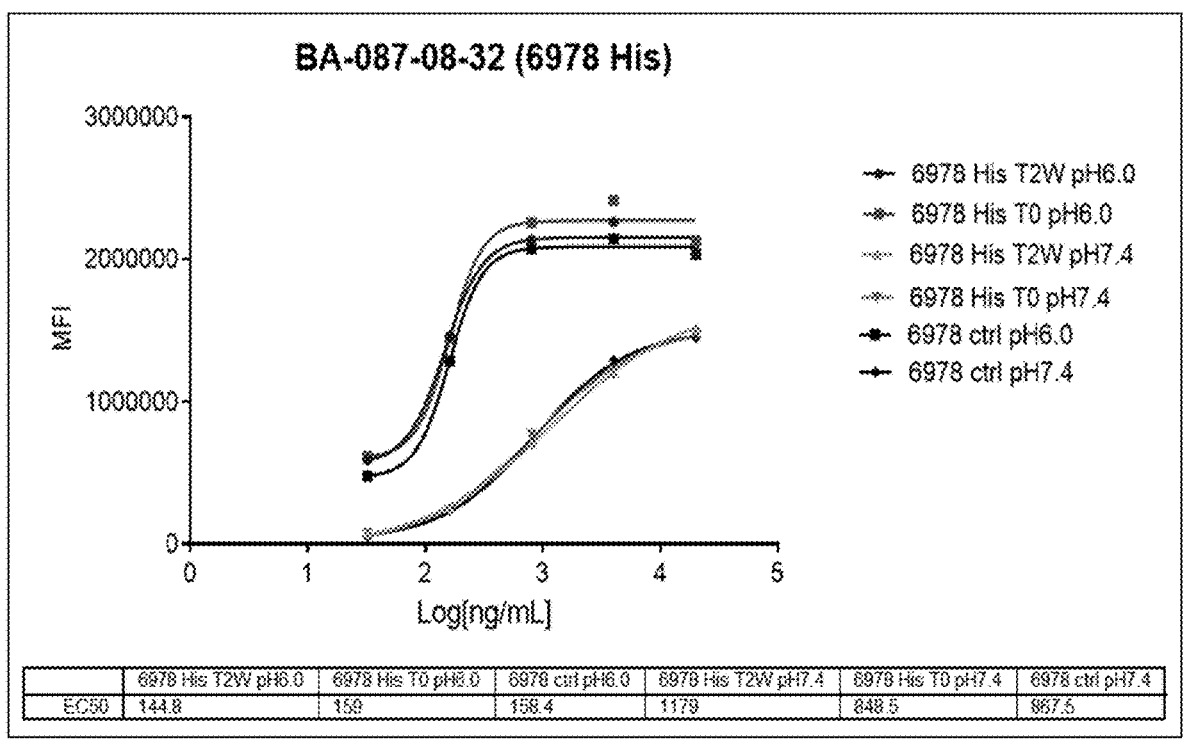
Figure 10E:
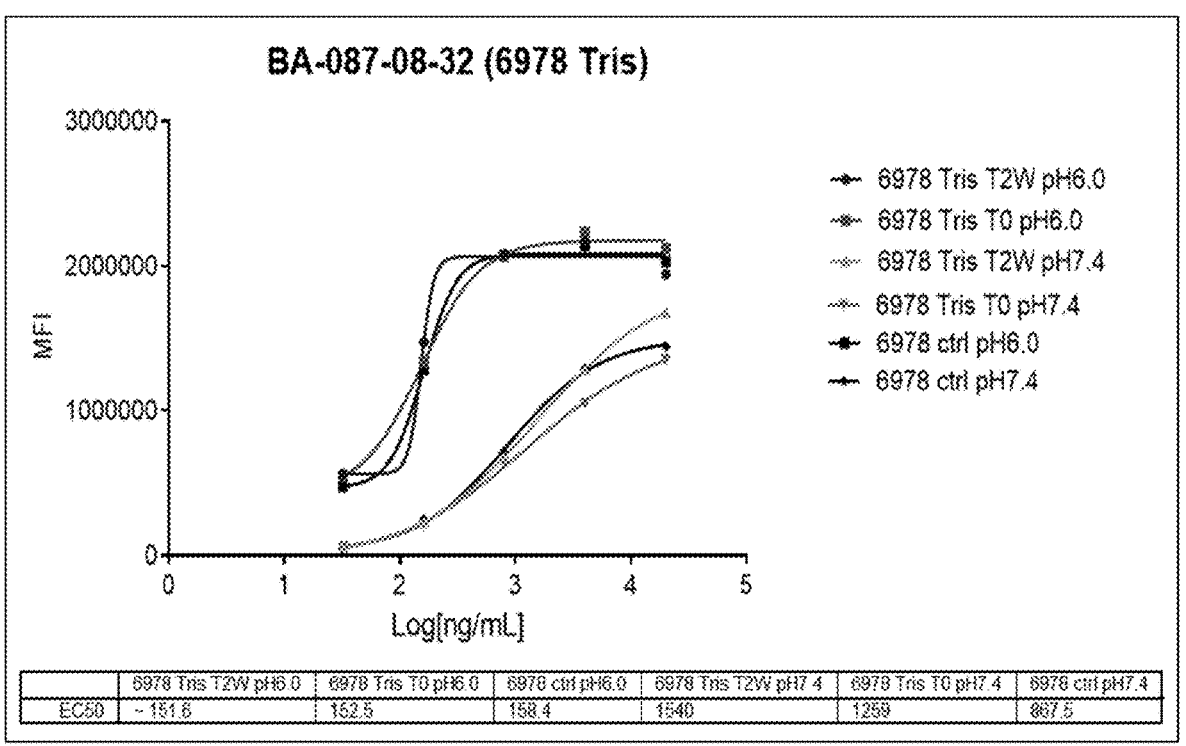
Figure 10F:
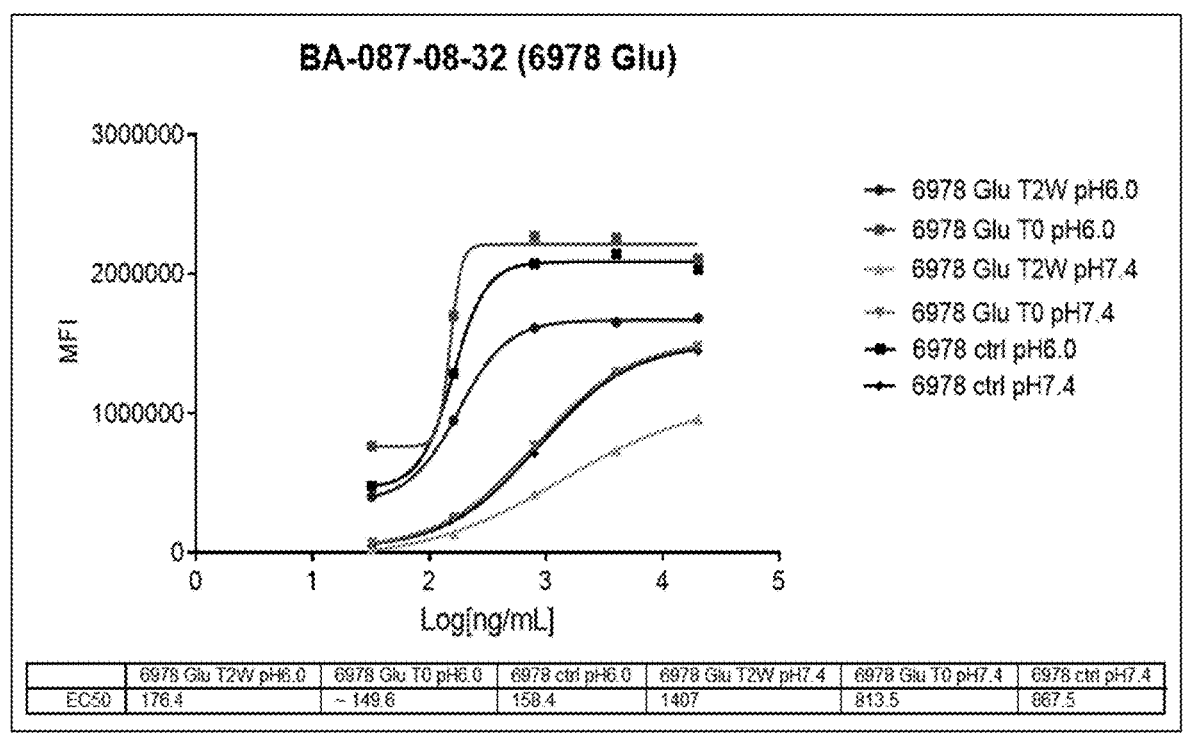

Finally, saturations of the antibodies on the CHO cells expressing human or cynomolgus CTLA4 at pH 7.4 were also measured by FACS (FIGS. 8A-8B). At pH 7.4, less of In FACS analysis, serially diluted BA-087-05-19 and BA-087-08-32 samples were added to cells expressing human CTLA4. The amount of bound antibodies was quantified using anti-human IgG antibody conjugated to fluorophores. The MFI in each reaction was proportional to the amount of antibodies bound. The binding activities as measured by FACS are shown in FIGS. 10A-10F. The $EC_{50}$ value (in ng/mL) for binding to human CTLA4 on cells was determined by MFI of the singlets population against antibody concentration with a Prism variable slope of four-parameter dose-response curve, which was calculated using the nonlinear fit (variable slope, four parameters) model built into GraphPad Prism software (version 7.03). The $EC_{50}$ values for binding to human CTLA4 on CHO cells are given in Tables 12-13.

TABLE 12

| EC50 of BA-087-05-19 in different buffers determined by FACS | | | | | | | |
| EC50 | BA-087-05-19 (6972 His) | | BA-087-05-19 (6972 Tris) | | BA-087-05-19 (6972 Glu) | | BA-087-05-19 (6972) | |
| (ng/mL) | pH 6.0 | pH 7.4 | pH 6.0 | pH 7.4 | pH 6.0 | pH 7.4 | pH 6.0 | pH 7.4 |
| T0 | 290.8 | 433.4 | 291.4 | 681.3 | 291 | 461.5 | 222.5 | 428.1 |
| T2W | 294.8 | 614.8 | 352.3 | 537.1 | 266.6 | 606.9 | 222.5 | 428.1 |

TABLE 13

| EC50 of BA-087-08-32 in different buffers determined by FACS | | | | | | | |
| EC50 | BA-087-08-32 (6978 His) | | BA-087-08-32 (6978 Tris) | | BA-087-08-32 (6978 Glu) | | BA-087-08-32 (6973) | |
| (ng/mL) | pH 6.0 | pH 7.4 | pH 6.0 | pH 7.4 | pH 6.0 | pH 7.4 | pH 6.0 | pH 7.4 |
| T0 | 159 | 848.5 | 152.5 | 1259 | 149.6 | 813.5 | 158.4 | 867.5 |
| T2W | 144.8 | 1179 | 151.6 | 1540 | 176.4 | 1407 | 158.4 | 867.5 |

Example 7: In Silico Immunogenecity Analysis of BA-087-05-19

This study determined the potential immunogenicity of BA-087-05-19 using an EpiVax's in silico immunogenicity screening toolkit. The software was accessed through ISPRI, a web-based interactive screening and protein reengineering interface. Using the BA-087-05-19 variable domain as input, the software was used to rate the immunogenic potential on a normalized scale and predict the potential ADA response.

The potential immunogenicity of BA-087-05-19 was analyzed and compared to known antibodies on a normalized scale. The data show that BA-087-05-19 has a Tregitope adjusted EpiMatrix Protein Score of −27.70 and a predicted T-dependent antibody response of 1.29%. This predicted low immunogenecity falls within the group of optimal antibodies (with low effector and high Tregitope content).

Example 8: Functional Assay of Potentiating IL-2 Secretion by Anti-CTLA4 Antibodies The functional activities of antibodies BA-087-05-19 and BA-087-08-32 in inducing IL-2 secretion by human lymphocytes stimulated with staphylococcal enterotoxin B (SEB) were determined in this example. Serially diluted BA-087-05-19, BA-087-08-32, Ipilimumab and Ipilimumab analogue were added to human peripheral blood mononuclear cells (PBMCs) from normal healthy donors stimulated with SEB. The ability of the antibodies to potentiate IL-2 secretion in SEB-stimulated human PBMCs was quantified using an IL-2 ELISA kit.

Figure 11A:
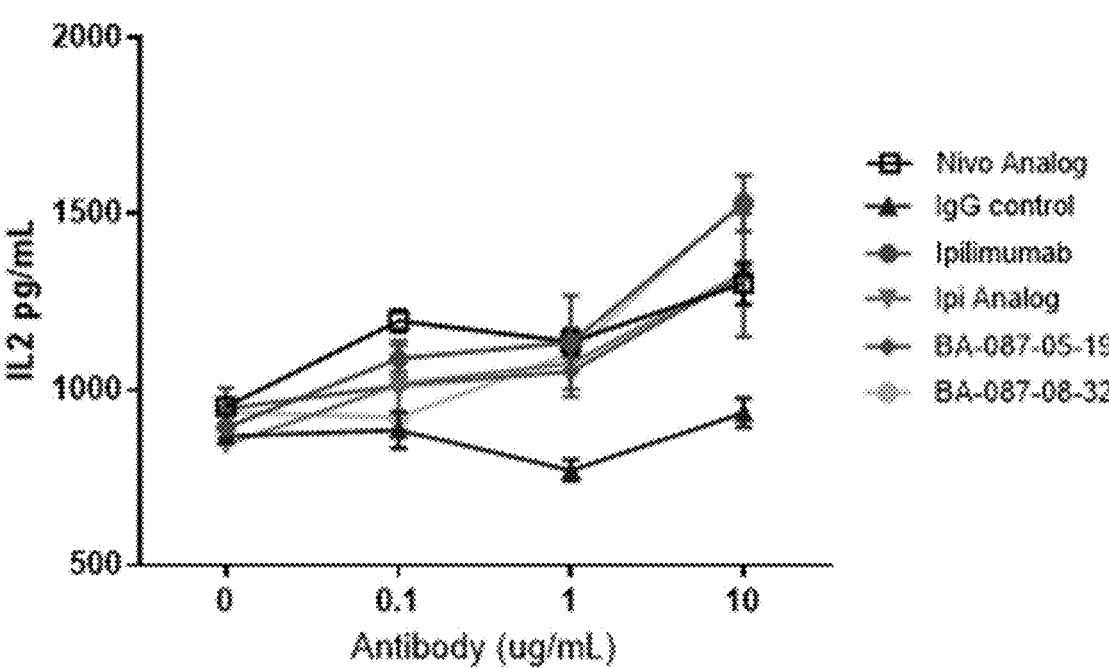
FIG. 11A shows a comparison of the activity the anti-CTLA4 antibodies of the present invention of FIG. 3A to Ipilimumab, an Ipilimumab analog (ipi-analog), an IgG control and a Nivo analog in blocking IL2 secretion in peripheral blood mononuclear cell (PBMC) cultures at pH 6.2.
Figure 11B:
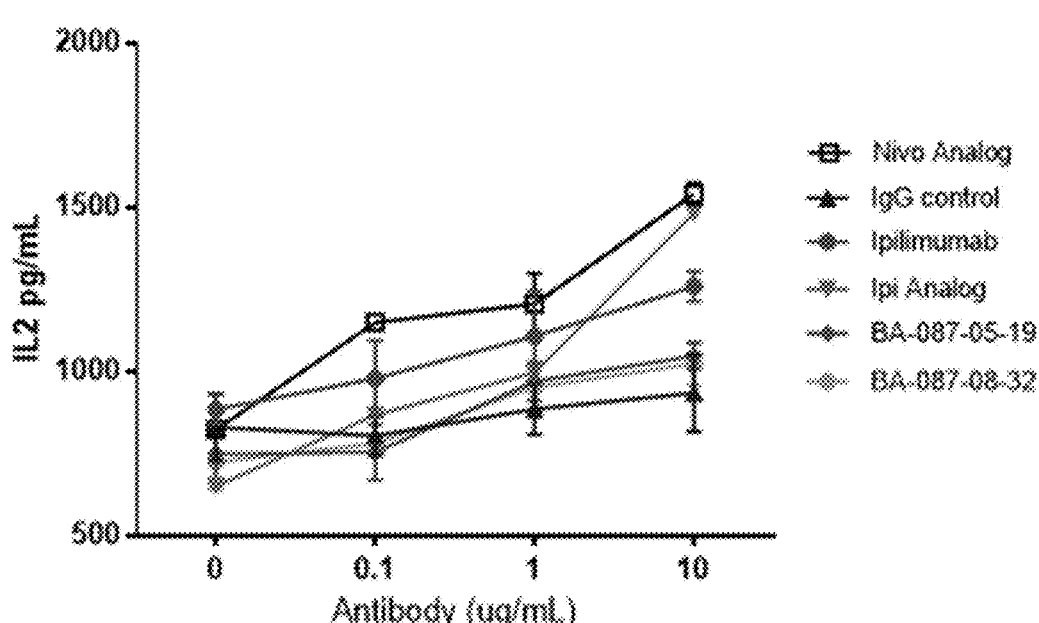
FIG. 11B shows a comparison of the activity the anti-CTLA4 antibodies of the present invention of FIG. 3A to Ipilimumab, an Ipilimumab analog (ipi-analog), an IgG control and a Nivo analog in blocking IL2 secretion in PBMC cultures at pH 7.4.

A total of three independent experiments were performed. In SEB-stimulated peripheral blood mononuclear cell (PBMC) cultures, the addition of BA-087-05-19 and BA-087-08-32 enhanced IL-2 production over the level observed with the addition of isotype control at the level observed with Ipilimumab and Ipilimumab analogue at pH 6.2, as shown in FIG. 11A. On the other hand, IL-2 production did not increase with the addition of BA-087-05-19 and BA-087-08-32 at pH 7.4 as shown in FIG. 11B.

At a concentration of 10 μg/mL, BA-087-05-19 promoted a mean 1.4 fold increase and BA-087-08-032 promoted mean 1.5 fold increase in IL-2 production as compare to the isotype control at pH 6.2, similar to the increase observed with Ipilimumab and Ipilimumab analogue. These results indicate that the functional activities of BA-087-05-19 and BA-087-08-32 are equivalent to the activity observed with Ipilimumab and Ipilimumab analogue at pH 6.2.

Example 9: Promega® CTLA4 Blockade Assay for Anti-CTLA4 Antibodies

The activity of antibodies BA-087-05-19 and BA-087-08-32 in blocking interactions between human CTLA4 and its ligands (CD80 nad CD87) was determined by use of an in vitro Promega® CTLA4 Blockade Assay. Serially diluted BA-087-05-19, BA-087-08-32, Ipilimumab and Ipilimumab analogue were added to Jurkat effector cells followed by addition of aAPC/Raji cells according to the vendor's protocol. The blockade of the interactions between CTLA4 and its ligands results in activation of the IL-2 pathway engineered in the Jurkat effector cells, which was quantified using a Bio-Glo® luciferase assay kit.

Figure 12A:
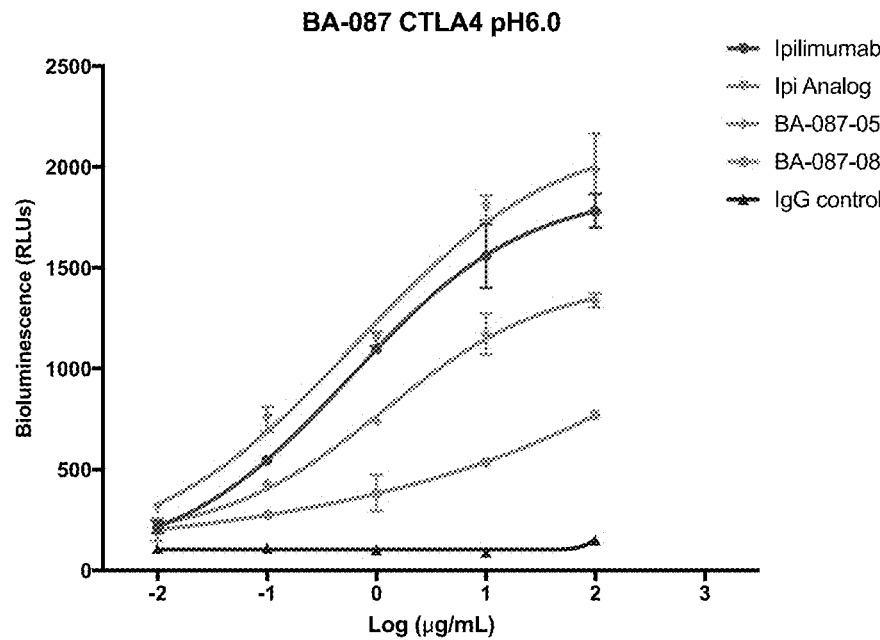
FIG. 12A shows a comparison of the $EC_{50}$ and the activity the anti-CTLA4 antibodies of the present invention of FIG. 3A to Ipilimumab, an Ipilimumab analog (ipi-analog), and an IgG control in blocking the interaction between CTLA4 and its ligands at pH 6.0.
Figure 12B:
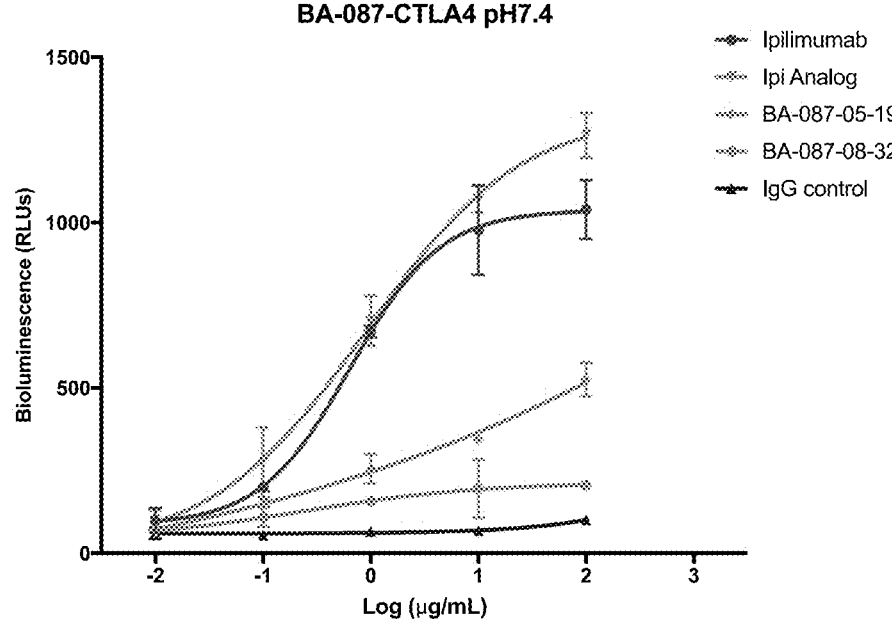
FIG. 12B shows a comparison of the $EC_{50}$ and the activity the anti-CTLA4 antibodies of the present invention of FIG. 3A to Ipilimumab, an Ipilimumab analog (ipi-analog), and an IgG control in blocking the interaction between CTLA4 and its ligands at pH 7.4.

The results showed that BA-087-05-19 and BA-087-08-32 were able to block the interaction between CTLA4 and its ligands (CD80/CD87) at a similar level observed with Ipilimumab and Ipilimumab analogue at pH 6.0 as shown in FIG. 12A. In contrast, BA-087-05-19 and BA-087-08-32 were less effective in blocking the interaction of CTLA4 with its ligands at pH 7.4 as shown in FIG. 12B. These results indicate that the in vitro functional activities of BA-087-05-19 and BA-087-08-32 are equivalent to the activities observed with Ipilimumab and Ipilimumab analogue at pH 6.0 significantly less than the activities of Ipilimumab and Ipilimumab in the blockade at pH 7.4.

Example 10: FACS Assay for Ligand Blocking by Anti-CTLA4 Antibodies

Figure 13A:
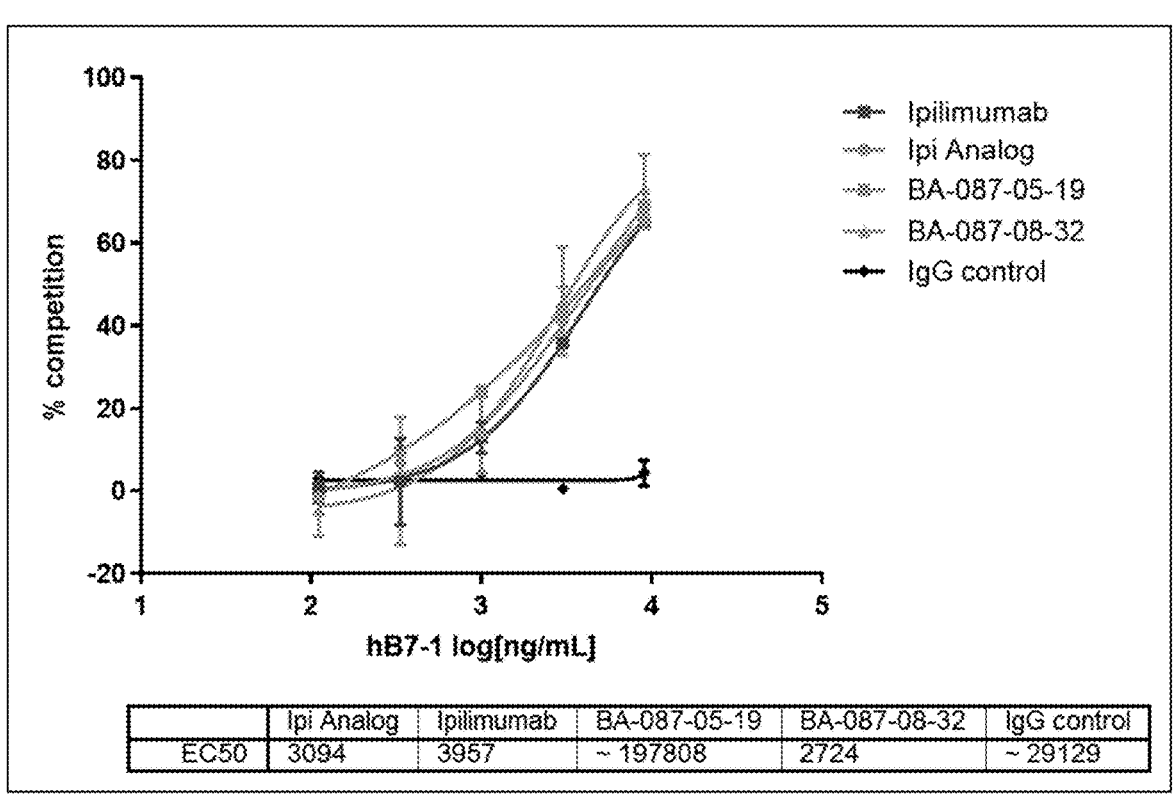
FIG. 13A shows a comparison of the $EC_{50}$ and the activity the anti-CTLA4 antibodies of the present invention of FIG. 3A to Ipilimumab, an Ipilimumab analog (ipi-analog), and an IgG control in competitive binding to human CTLA4 as a function of the concentration of the ligand hB7-1 (hCD80) of CTLA4, as measured by FACS.
Figure 13B:
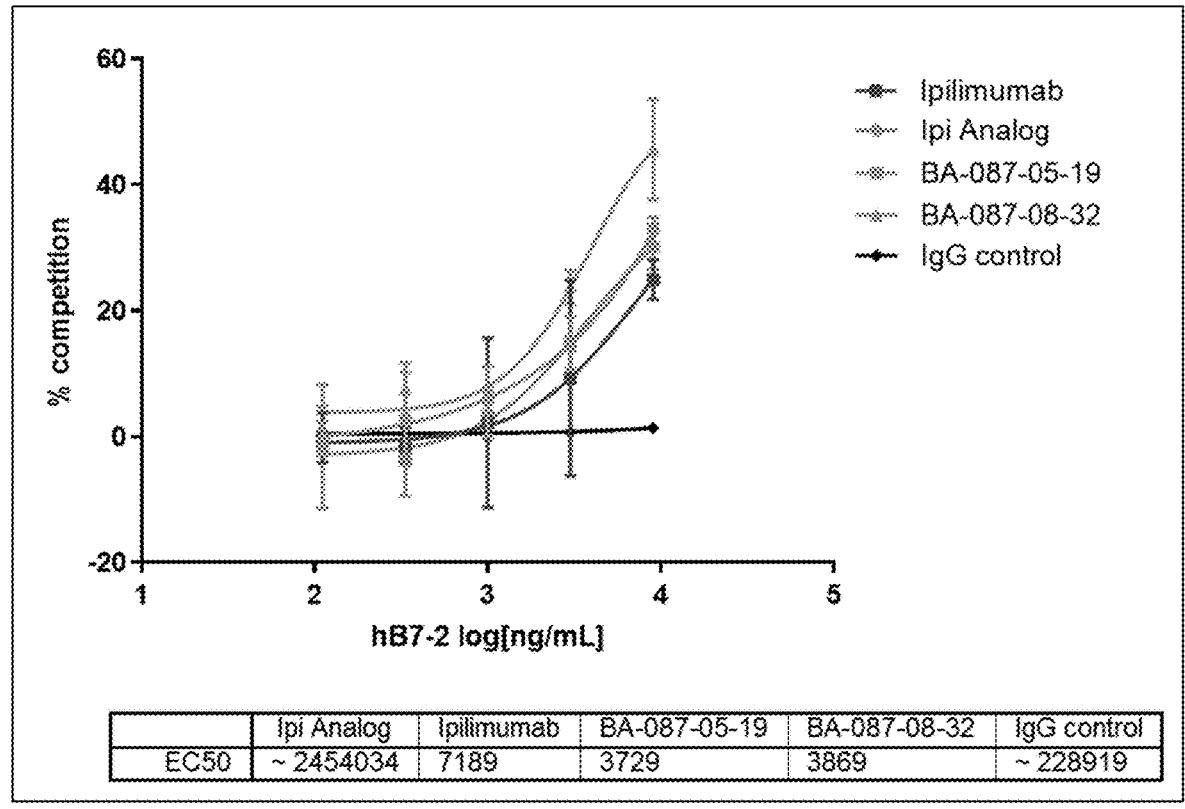
FIG. 13B shows a comparison of the $EC_{50}$ and the activity the anti-CTLA4 antibodies of the present invention of FIG. 3A to Ipilimumab, an Ipilimumab analog (ipi-analog), and an IgG control in competitive binding to human CTLA4 as a function of the concentration of the ligand hB7-2 (hCD86) of CTLA4, as measured by FACS.

The activities of BA-087-05-19 and BA-087-08-32 for inhibiting the interaction of human CTLA4 with its ligands hB7-1 (hCD80) and hB7-2 (hCD86) were assayed by FACS to assess the competitive binding at a fixed concentration of BA-087-05-19 and BA-087-08-32 to CHO cells expressing human CTLA4 in the presence of different concentrations of hB7-1 and hB7-2. The amounts of BA-087-05-19 and BA-087-08-32 bound to CHO-huCTLA4 cells were quantified using anti-human IgG antibody conjugated to fluorophores. The mean fluorescence intensity (MFI) in each reaction was proportional to the amount of BA-087-05-19 and BA-087-08-32 bound to CHO-huCTLA4 as shown in FIGS. 13A-13B.

Figure 14A:
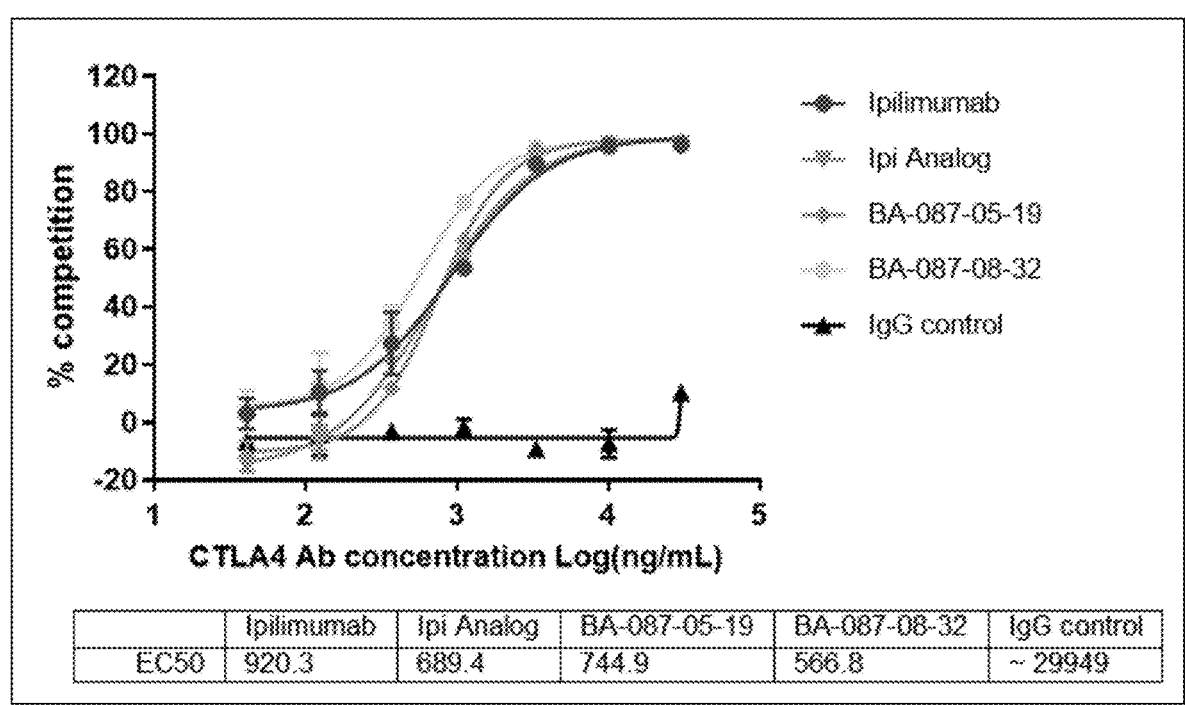
FIG. 14A shows a comparison of the activity the anti-CTLA4 antibodies of the present invention of FIG. 3A to Ipilimumab, an Ipilimumab analog (ipi-analog), and an IgG control in competitive binding to human CTLA4 at fixed concentration of ligand hB7-1 of CTLA4 as a function of antibody concentration as measured by FACS.
Figure 14B:
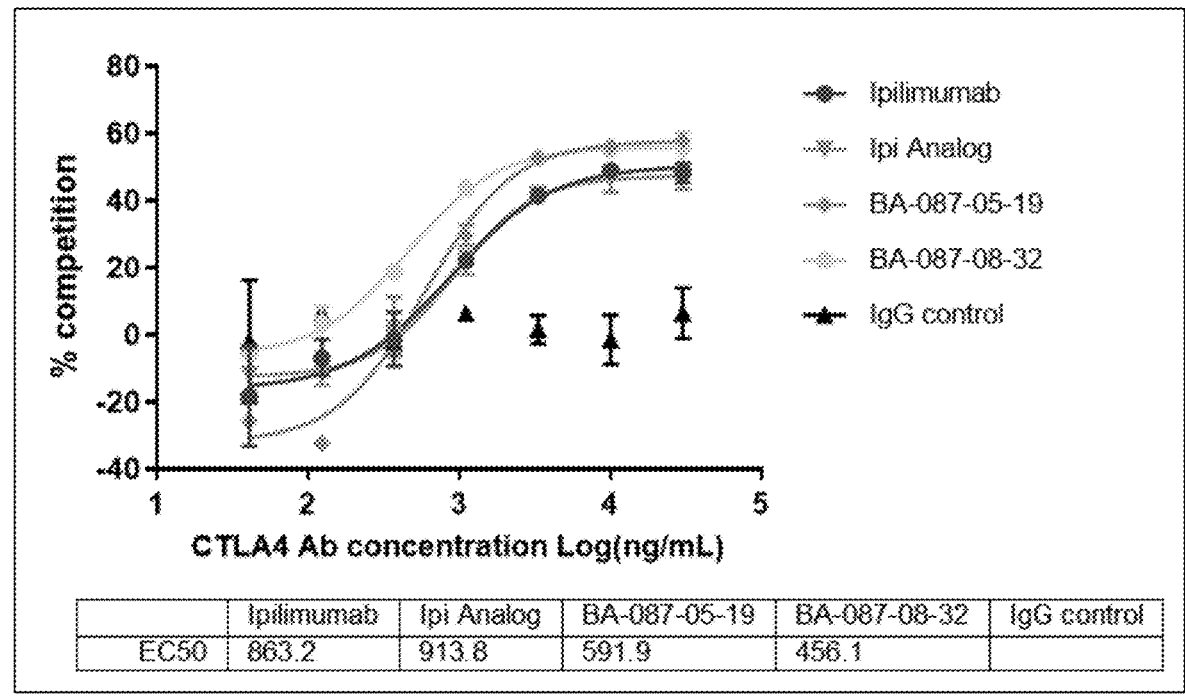
FIG. 14B shows a comparison of the activity the anti-CTLA4 antibodies of the present invention of FIG. 3A to Ipilimumab, an Ipilimumab analog (ipi-analog), and an IgG control in competitive binding to human CTLA4 at fixed concentration of ligand hB7-2 of CTLA4 as a function of antibody concentration as measured by FACS.

In addition, FACS analysis was used to determine the competitive binding of serially diluted BA-087-05-19 and BA-087-08-32 to CHO cells expressing human CTLA4 at a fixed concentration of hB7-1 and hB7-2. The amount of hB7-1 and hB7-2 bound to CHO-huCTLA4 cells was quantified using anti-His antibody and anti-mouse IgG antibody conjugated to fluorophores. The MFI in each reaction was proportional to the amount of hB7-1 and hB7-2 bound to CHO-huCTLA4. The data showed that BA-087-05-19 and BA-087-08-32 blocked the interaction of huCTLA4 with its ligands, hB7-1 and hB7-2 at levels similar to those achieved by Ipilimumab and Ipilimumab analogue (FIGS. 14A-14B).

The data show that BA-087-05-19 and BA-087-08-32 are able to block the interaction between human CTLA4 and its ligands hB7-1 (hCD80) and hB7-2 (hCD86) as efficiently as Ipilimumab and Ipilimumab analogue. Competition FACS analysis was only performed at pH 6.0 because BA-087-05-19 and BA-087-08-32 have very limited binding at pH 7.4.

Methods Used in the Examples

The ELISA assay was performed using the following protocol:

1) Coat ELISA plates with 100 µL of 0.5 µg/mL (06_20_17 and 06_28_17 Experiments) or 1 µg/mL (07_06_17 and 07_11_17 Experiments) recombinant CTLA4 antigen in carbonate-bicarbonate coating buffer 2) Cover plates with sealing film and incubate overnight at 4° C.

3) Decant plates and tap out residual liquid on a stack of paper towels

4) Wash wells twice by dispensing 200 µL of various pH incubation buffer to the wells according to a sample map and completely aspirate the contents 5) Add 200 µL of various pH incubation buffer to the wells according to the sample map. Cover with sealing film and place the plate onto a plate shaker (set to 200 rpm) for 60 minutes at room temperature 6) Decant plates and tap out residual liquid on a stack of paper towels.

7) Serially dilute test substances in various pH incubation buffers to 250 ng/mL, 100 ng/mL or 25 ng/mL.

8) Add 100 µL/well of diluted test substances to the plates according to the sample map.

9) Cover with sealing film and place the plates onto a plate shaker (set to 200 rpm) for 60 minutes at room temperature.

10) Decant plates and tap out residual liquid on a stack of paper towels.

11) Wash wells three times by dispensing 200 µL of various pH wash buffers to the wells according to the sample map and completely aspirate the contents 12) Dilute the HRP secondary antibody at 1:2500 in various pH incubation buffers 13) Add 100 µL HRP secondary antibody diluted in various pH incubation buffers to each well according to the sample map.

14) Cover with sealing film and place the plates onto a plate shaker (set to 200 rpm) for 60 minutes at room temperature.

15) Decant plates and tap out residual liquid on a stack of paper towels.

16) Wash wells three times by dispensing 200 µL of various pH wash buffer to the wells according to the sample map and completely aspirating the contents 17) Dispense 50 µL per well of the TMB substrate solution into all wells of plates. Incubate at room temperature for 3 minutes.

18) Add 50 µL per well of 1N HCl into all wells of the plates. Read plates at 450 nm using Molecular Device SpectraMax 190 microplate reader.

19) The OD450 nm raw data are measured.

20) The average OD values (from 2 replicates) at the different pH were plotted against the pH of the buffer using Softmax Pro software (Molecular Devices). Curve fitting was done using the 4-parameter model built into the software. The inflection point of the pH curve (50% binding activity) equals parameter C of the fitting equation. Binding activity at pH 6.0 was set to 100%. The pH for 90% binding activity was interpolated from the fitted curve using the "InterpX" function of the Softmax Pro software.

The Surface Plasma Resonance (SPR) Assay Wass Performed Using the Following Protocol:

The SPR 2/4 instrument, SPR Affinity Sensors—Amine Flat, and Immobilization buffer kit are manufactured by Sirra Sensors. The SPR sensor contains four flow cells (FC1-FC4), each of which can be addressed individually or in groups. CTLA4 extracellular domain was immobilized in FC2 and FC4, while BSA was immobilized in FC1 and FC3 (control surface).

Immobilization was done following the protocol suggested by vendor:

(1) The activator was prepared by mixing 200 mM EDC and 50 mM NHS (Sierra Sensors) immediately prior to injection. The amine sensor chip was activated for 480 s with the mixture at a flow rate of 25 µL/min.

(2) 25 µg/mL of human CTLA4 in 10 mM NaAc (pH 5.0) was injected to FC2 and FC4 respectively at a flow rate of 25 µL/min for 480 s. The chip surface was deactivated with 1 M ethanolamine-HCl (Sierra Sensors) running through FC1-4 at a flow rate of 25 µL/min for 480 s.

(3) The control surface was activated and deactivated using the same conditions, but without injecting protein.

(4) The running buffer was switched to PBST with the required pH before the analyte injections. The instrument was equilibrated with the running buffer for 1 hour before the first analyte injection.

(5) All analyte injections were done at 25 µL/min at 25° C.

BA-087-05-19 was diluted in running buffer (buffer PBST pH 6.0 or 7.4) to 5 µg/mL (34.25 nM), 2 µg/mL (13.70 nM), 1 µg/mL (6.85 nM), 0.5 µg/mL (3.42 nM), 0.2 µg/mL (1.37 nM) and 0 µg/mL (0.0 nM). BA-087-08-32 was diluted in running buffer (buffer PBST pH 6.0 or 7.4) to 5 µg/mL (34.25 nM), 2 µg/mL (13.70 nM), 1 µg/mL (6.85 nM), 0.5 µg/mL (3.42 nM), 0.2 µg/mL (1.37 nM) and 0 µg/mL (0.0 nM).

100 µL diluted analyte BA-087-05-19 or BA-087-08-32 was injected over flow cells 1 and 2 (or 3 and 4) at a flow rate of 25 µL/min for an association phase of 240 s followed by 360 s dissociation. Repeat 6 cycles of running analyte according to the analyte concentrations in ascending order. The chip surface was regenerated after each cycle of interaction analysis by injecting 6 µL of 10 mM glycine (pH 2.0). Each set was run a total of 3 times at the same pH.

Flow cell 1 (or 3) without immobilized protein was used as control surface for reference subtraction. In addition, data with buffer only as analyte (0 nM analyte) were subtracted from each run. Double subtracted data were fitted with the provided analysis software Analyzer R2 (Sierra Sensors) using a 1:1 binding model. A molecular weight of 146 kDa was used to calculate the molar concentrations of the analytes.

The Fluorescence-Activated Cell Sorting (FACS) Assay was Performed Using the Following Protocol.

Cell staining to determine surface expression of human or cynomolgus CTLA4

1) Seed $3\times10^6$ cells to T-75 flasks and culture according to the instructions of vendors.
2) On the day of FACS analysis, remove and discard culture medium.
3) Briefly rinse the cell layer with PBS solution.
4) Add 1.5 mL of Detachin solution to each of the T-75 flasks. Wait until cell layer is dispersed.
5) Add 4.5 mL of culture media for the corresponding cell lines and resuspend cells by gentle pipetting.
6) Pool the cells and transfer the cell suspension to a 50-mL conical tube.
7) Count the cells with trypan blue staining before centrifugation at 1500 rpm for 5 min at 4° C.
8) Wash the cells once with PBS and transfer $3\times10^5$ cells into Eppendorf tube.
9) Add 2 μL of mouse anti-CTLA4 (PE conjugated mouse IgG1) or PE-isotype mouse IgG1 in 100 μL of PBS solution with 1% BSA per tube and shake at 100 RPM for one hour on ice.
10) Wash cells three times with 150 μL PBS solution.
11) Fix cells with 4% PFA for 10 min at R.T., then wash cells with PBS once.
12) Resuspend cells in 100 μL PBS and analyze the cells on NovoCyte flow cytometer.

FACS analysis of CHO cells expressing human CTLA4 or cynomolgus CTLA4 using tested antibody.

1) Harvest the cells (as 3.3, steps 1 through 7), wash the cells once with PBS.
2) Resuspend the cells in pH 6.0 or pH 7.4 FACS buffer to $3\times10^6$ cells/mL.
3) Aliquot $3\times10^5$ cells in 100 μL pH 6.0 or pH 7.4 FACS buffer in 96-well U-bottom plates.
4) Spin down the cells and discard the buffer.
5) Serially dilute test articles in 3-fold dilutions starting at 10 μg/mL (06-16-17, 06-26-17 and 06-28-17 Experiments for total 8 data points or at 100 μg/mL (07_10_17 experiment for total 11 data points) in pH 6.0 or pH 7.4 FACS buffer.
6) Add 100 μL/well of the diluted test articles to cells, gently mix well and incubate on ice with shaking (100 rpm) for one hour.
7) Centrifuge the cells at 1500 rpm for 5 min at 4° C. Wash the cells with 150 μL of pH 6.0 or pH 7.4 wash buffer for two times.
8) Dilute the goat anti-human IgG AF488 antibody 1:300 in pH 6.0 or pH 7.4 FACS buffers.
9) Add 100 μL of the diluted antibody from step above to the cells and incubate on ice for 45 minutes, protected from light.
10) Pellet the cells and wash with 150 μL of pH 6.0 or pH 7.4 wash buffer for three times.
11) Fix cells with 4% PFA diluted in 1×PBS for 10 min at R.T., then wash cells with 1×PBS.
12) Resuspend the cells in 100 μL of 1×PBS.

13) Analyze the cells by NovoCyte Flow Cytometer using Ex488 nm/Em530 nm. Collect at least 20,000 cells.

FACS data were analyzed using the nonlinear fit (variable slope, four parameters) model built into GraphPad Prism software version 7.03.

PROMEGA® CTLA4 Blockade Assay

1) Transfer a vial of Thaw-and-Use CTLA4 Jurkat effector cells (CS186912) from liquid nitrogen storage to the bench on dry ice. Thaw the vial in a 37° C. water bath until cells are just thawed (about 2 minutes). While thawing gently agitate and visually inspect, do not invert.
2) Gently mix the cell suspension in the vial by pipetting up and down 2-3 times, and transfer 0.8 mL to the tube labeled "CTLA4 cells" containing 3.2 mL RPMI+10% FBS.
3) Spin the cells down at 1500 rpm for 10 min and resuspend in 1 mL RPMI+10% FBS. Mix well, divide the cell suspension into two tubes and spin cells down, wash the pellet once with either pH 6.0 or pH 7.4 assay media, and then resuspend the cell pellet into 2 mL of pH 6.0 or pH 7.4 assay media.
4) Immediately dispense 25 μL of CTLA4 Jurkat effector cells into the inner 60 wells of 96-well plate according to the layout.
5) Add 100 μL of sterile water per well to the unused wells surrounded the sample wells.
6) Make serial dilution of 3× test article stocks in pH 6.0 or pH 7.4 assay media in duplicates starting at 300 μg/mL to generate 10-fold dilution data points.
7) Dispense 25 μL of serially diluted 3× test article stocks to the wells containing 25 μL of CTLA4 Jurkat effector cells according to the layout.
8) Transfer a vial of Thaw-and-Use CTLA4 aAPC/Raji cells (CS186911) from liquid nitrogen storage to the bench on dry ice. Thaw the vial in a 37° C. water bath until cells are just thawed (about 2 minutes). While thawing gently agitate and visually inspect, do not invert.
9) Gently mix cell suspension in the vial by pipetting up and down 2-3×, and transfer 0.8 mL to the tube labeled "aAPC/Raji cells" containing 7.2 mL RPMI+10% FBS.
10) Spin the cells down at 1500 rpm for 10 min and resuspend in 1 mL RPMI+10% FBS. Mix well, divide the cell suspension into two tubes and spin cells down, wash the pellet with pH 6.0 or pH 7.4 assay media once, and then resuspend the cell pellet into 4 mL of pH 6.0 or pH 7.4 assay media.
11) Immediately dispense 25 μL of CTLA4 aAPC/Raji cells into the inner 60 wells of assay plates already containing 50 μL cells and antibody solution. The total assay volume is 75 μL.
12) Place lid on the plates and incubate the plates for 16 hours at 37° C. in 5% $CO_2$ humidified incubator.
13) During the 16-hour induction time, warm Bio-Glo™ buffer to ambient temperature using a room temperature water bath, prior to addition to Bio-Glo™ substrate.
14) Reconstitute Bio-Glo™ Luciferase Assay System by transferring one bottle of Bio-Glo™ buffer to the bottle containing Bio-Glo™ substrate.
15) After 16-hour induction, remove assay plates from the $CO_2$ incubator and equilibrate at ambient temperature for 15 min.
16) Add 75 μL of Bio-Glo™ reagent to the inner 60 wells of the assay plates.
17) Incubate plates for 5-10 min at ambient temperature.

18) Record luminescence on the SpectraMax i3X plate reader.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

All documents mentioned herein are hereby incorporated by reference in their entirety or alternatively to provide the disclosure for which they were specifically relied upon. The applicant(s) do not intend to dedicate any disclosed embodiments to the public, and to the extent any disclosed modifications or alterations may not literally fall within the scope of the claims, they are considered to be part hereof under the doctrine of equivalents.

---

SEQUENCE LISTING

```
Sequence total quantity: 58
SEQ ID NO: 1            moltype = AA   length = 10
FEATURE                 Location/Qualifiers
REGION                  1..10
                        note = Synthetic sequence
source                  1..10
                        mol_type = protein
                        organism = synthetic construct
SEQUENCE: 1
GFTFSHYTMH                                                           10

SEQ ID NO: 2            moltype = AA   length = 17
FEATURE                 Location/Qualifiers
REGION                  1..17
                        note = Synthetic sequence
VARIANT                 3
                        note = This may be amino acid S or D
VARIANT                 5
VARIANT                 8
                        note = This may be amino acid N or Y
VARIANT                 10
                        note = This may be amino acid Y or I
VARIANT                 11
                        note = This may be amino acid Y or E
VARIANT                 13
                        note = This may be amino acid D or K
VARIANT                 15
                        note = This may be amino acid V or M
source                  1..17
                        mol_type = protein
                        organism = synthetic construct
SEQUENCE: 2
FIXYXGNXKX XAXSXKG                                                   17

SEQ ID NO: 3            moltype = AA   length = 9
FEATURE                 Location/Qualifiers
REGION                  1..9
                        note = synthetic sequence
VARIANT                 9
                        note = This amino acid may be Y or I
source                  1..9
                        mol_type = protein
                        organism = synthetic construct
SEQUENCE: 3
TGWLGPFDX                                                            9

SEQ ID NO: 4            moltype = AA   length = 12
FEATURE                 Location/Qualifiers
REGION                  1..12
                        note = Synthetic sequence
VARIANT                 2
                        note = This amino acid may be A or I
VARIANT                 5
                        note = This amino acid may be Y, S or H
VARIANT                 6
                        note = This amino acid may be V or G
source                  1..12
                        mol_type = protein
                        organism = synthetic construct
SEQUENCE: 4
RXSQXXGSSY LA                                                        12

SEQ ID NO: 5            moltype = AA   length = 9
FEATURE                 Location/Qualifiers
REGION                  1..9
```

-continued

```
                              note = Synthetic sequence
VARIANT                       9
                              note = This amino acid may be V or I
source                        1..9
                              mol_type = protein
                              organism = synthetic construct
SEQUENCE: 5
GAFSRATGX                                                                9

SEQ ID NO: 6                  moltype = AA   length = 9
FEATURE                       Location/Qualifiers
REGION                        1..9
                              note = Synthetic sequence
source                        1..9
                              mol_type = protein
                              organism = synthetic construct
SEQUENCE: 6
QQDGSSPWT                                                                9

SEQ ID NO: 7                  moltype = AA   length = 108
FEATURE                       Location/Qualifiers
REGION                        1..108
                              note = synthetic sequence
source                        1..108
                              mol_type = protein
                              organism = synthetic construct
SEQUENCE: 7
AIQLTQSPSS LSASVGDRVT ITCRASQYVG SSYLAWYLQK PGQSPQLLIY GAFSRATGIP   60
ARFSGSGSGT EFTLTISSLQ SEDFAVYYCQ QDGSSPWTFG QGTKVEIK                 108

SEQ ID NO: 8                  moltype = AA   length = 118
FEATURE                       Location/Qualifiers
REGION                        1..118
                              note = Synthetic sequence
source                        1..118
                              mol_type = protein
                              organism = synthetic construct
SEQUENCE: 8
EVQLVESGGG LVQPGGSLRL SCAASGFTFS HYTMHWVRQA PGKGLEWVSF ISYDGNNKYY   60
ADSVKGRFTI SRDNSKNTLY LQMNSLRAED TAVYYCARTG WLGPFDYWGQ GTLVTVSS     118

SEQ ID NO: 9                  moltype = AA   length = 108
FEATURE                       Location/Qualifiers
REGION                        1..108
                              note = Synthetic sequence
source                        1..108
                              mol_type = protein
                              organism = synthetic construct
SEQUENCE: 9
EIVMTQSPAT LSVSPGERAT LSCRASQSVG SSYLAWYQQK PGKAPKLLIY GAFSRATGVP   60
SRFSGSGSGT DFTLTISSLQ PEDFATYYCQ QDGSSPWTFG QGTKVEIK                 108

SEQ ID NO: 10                 moltype = AA   length = 118
FEATURE                       Location/Qualifiers
REGION                        1..118
                              note = Synthetic sequence
source                        1..118
                              mol_type = protein
                              organism = synthetic construct
SEQUENCE: 10
EVQLVQSGAE VKKPGATVKI SCKVSGFTFS HYTMHWIRQS PSRGLEWLGF ISYDGNYKYY   60
ADSVKGRFTI SRDNAKNSLY LQMNSLRAED TAVYYCARTG WLGPFDYWGQ GTLVTVSS     118

SEQ ID NO: 11                 moltype = AA   length = 108
FEATURE                       Location/Qualifiers
REGION                        1..108
                              note = Synthetic sequence
source                        1..108
                              mol_type = protein
                              organism = synthetic construct
SEQUENCE: 11
AIQLTQSPSS LSASVGDRVT ITCRISQYVG SSYLAWYQQK PGKAPKLLIY GAFSRATGIP   60
DRFSGSGSGT DFTLTISRLE PEDFAVYYCQ QDGSSPWTFG QGTKVEIK                 108

SEQ ID NO: 12                 moltype = AA   length = 118
FEATURE                       Location/Qualifiers
REGION                        1..118
                              note = Synthetic sequence
source                        1..118
```

-continued

```
                            mol_type = protein
                            organism = synthetic construct
SEQUENCE: 12
EVQLVESGGG LVQPGGSLRL SCAASGFTFS HYTMHWVRQA TGQGLEWMGF ISYHGNNKYY   60
ADSVKGRFTI SRDNSKNTLY LQMNSLRAED TAVYYCARTG WLGPFDYWGQ GTLVTVSS    118

SEQ ID NO: 13              moltype = AA   length = 108
FEATURE                    Location/Qualifiers
REGION                     1..108
                           note = Synthetic sequence
source                     1..108
                           mol_type = protein
                           organism = synthetic construct
SEQUENCE: 13
AIQLTQSPSS LSASVGDRVT ITCRISQYVG SSYLAWYQQK PGKAPKLLIY GAFSRATGIP   60
DRFSGSGSGT DFTLTISRLE PEDFAVYYCQ QDGSSPWTFG QGTKVEIK             108

SEQ ID NO: 14              moltype = AA   length = 118
FEATURE                    Location/Qualifiers
REGION                     1..118
                           note = Synthetic sequence
source                     1..118
                           mol_type = protein
                           organism = synthetic construct
SEQUENCE: 14
EVQLVQSGAE VKKPGATVKI SCKVSGFTFS HYTMHWVRQA RGQRLEWMGF IDYHGNNKYY   60
ADSVKGRFTI SRDNAKNSLY LQMNSLRAED TAVYYCARTG WLGPFDYWGQ GTLVTVSS    118

SEQ ID NO: 15              moltype = AA   length = 108
FEATURE                    Location/Qualifiers
REGION                     1..108
                           note = Synthetic sequence
source                     1..108
                           mol_type = protein
                           organism = synthetic construct
SEQUENCE: 15
EIVLTQSPAT LSLSPGERAT LSCRASQYGG SSYLAWYQQK PGKAPKLLIY GAFSRATGVP   60
SRFSGSGSGT DFTFTISSLQ PEDIATYYCQ QDGSSPWTFG QGTKVEIK             108

SEQ ID NO: 16              moltype = AA   length = 118
FEATURE                    Location/Qualifiers
REGION                     1..118
                           note = Synthetic sequence
source                     1..118
                           mol_type = protein
                           organism = synthetic construct
SEQUENCE: 16
QVQLVQSGAE VKKPGASVKV SCKASGFTFS HYTMHWIRQP PGKGLEWIGF ISYDGNNKIY   60
ADSVKGRFTI SRDNSKNTLY LQMNSLRAED TAVYYCARTG WLGPFDIWGQ GTLVTVSS    118

SEQ ID NO: 17              moltype = AA   length = 108
FEATURE                    Location/Qualifiers
REGION                     1..108
                           note = Synthetic sequence
source                     1..108
                           mol_type = protein
                           organism = synthetic construct
SEQUENCE: 17
DIQMTQSPSS LSASVGDRVT ITCRASQYGG SSYLAWYQQK PGQAPRLLIY GAFSRATGVP   60
SRFSGSGSGT DFTFTISSLQ PEDIATYYCQ QDGSSPWTFG QGTKVEIK             108

SEQ ID NO: 18              moltype = AA   length = 118
FEATURE                    Location/Qualifiers
REGION                     1..118
                           note = Synthetic sequence
source                     1..118
                           mol_type = protein
                           organism = synthetic construct
SEQUENCE: 18
QVQLVQSGAE VKKPGASVKV SCKASGFTFS HYTMHWIRQP PGKGLEWIGF ISYDGNNKIY   60
ADSVKGRFTI SRDNSKNTLY LQMNSLRAED TAVYYCARTG WLGPFDIWGQ GTLVTVSS    118

SEQ ID NO: 19              moltype = AA   length = 108
FEATURE                    Location/Qualifiers
REGION                     1..108
                           note = Synthetic sequence
source                     1..108
                           mol_type = protein
                           organism = synthetic construct
```

```
SEQUENCE: 19
AIQLTQSPSS LSASVGDRVT ITCRASQYVG SSYLAWYQQK PGQAPRLLIY GAFSRATGIP  60
ARFSGSGSGT EFTLTISSLQ SEDFAVYYCQ QDGSSPWTFG QGTKVEIK              108

SEQ ID NO: 20            moltype = AA  length = 118
FEATURE                  Location/Qualifiers
REGION                   1..118
                         note = Synthetic sequence
source                   1..118
                         mol_type = protein
                         organism = synthetic construct
SEQUENCE: 20
EVQLVQSGAE VKKPGESLRI SCKGSGFTFS HYTMHWVRQA PGKGLEWVSF ISYHGNNKYE  60
ADSVKGRFTI SRDNAKNSLY LQMNSLRAED TAVYYCARTG WLGPFDYWGQ GTLVTVSS    118

SEQ ID NO: 21            moltype = AA  length = 108
FEATURE                  Location/Qualifiers
REGION                   1..108
                         note = Synthetic sequence
source                   1..108
                         mol_type = protein
                         organism = synthetic construct
SEQUENCE: 21
AIQLTQSPSS LSASVGDRVT ITCRISQYVG SSYLAWYQQK PGKAPKLLIY GAFSRATGIP  60
DRFSGSGSGT DFTLTISRLE PEDFAVYYCQ QDGSSPWTFG QGTKVEIK              108

SEQ ID NO: 22            moltype = AA  length = 118
FEATURE                  Location/Qualifiers
REGION                   1..118
                         note = Synthetic sequence
source                   1..118
                         mol_type = protein
                         organism = synthetic construct
SEQUENCE: 22
EVQLVQSGAE VKKPGESLRI SCKGSGFTFS HYTMHWVRQA PGKGLEWVSF ISYHGNNKYE  60
ADSVKGRFTI SRDNSKNTLY LQMNSLRAED TAVYYCARTG WLGPFDYWGQ GTLVTVSS    118

SEQ ID NO: 23            moltype = AA  length = 108
FEATURE                  Location/Qualifiers
REGION                   1..108
                         note = Synthetic sequence
source                   1..108
                         mol_type = protein
                         organism = synthetic construct
SEQUENCE: 23
AIQLTQSPSS LSASVGDRVT ITCRASQYVG SSYLAWYLQK PGQSPQLLIY GAFSRATGVP  60
SRFSGSGSGT EFTLTISSLQ PDDFATYYCQ QDGSSPWTFG QGTKVEIK              108

SEQ ID NO: 24            moltype = AA  length = 118
FEATURE                  Location/Qualifiers
REGION                   1..118
                         note = Synthetic sequence
source                   1..118
                         mol_type = protein
                         organism = synthetic construct
SEQUENCE: 24
EVQLVQSGAE VKKPGATVKI SCKVSGFTFS HYTMHWIRQS PSRGLEWLGF ISYDGNYKYY  60
ADSVKGRFTI SRDNAKNSLY LQMNSLRAED TAVYYCARTG WLGPFDYWGQ GTLVTVSS    118

SEQ ID NO: 25            moltype = AA  length = 108
FEATURE                  Location/Qualifiers
REGION                   1..108
                         note = Synthetic sequence
source                   1..108
                         mol_type = protein
                         organism = synthetic construct
SEQUENCE: 25
AIQLTQSPSS LSASVGDRVT ITCRASQSVG SSYLAWYQQK PGQAPRLLIY GAFSRATGIP  60
ARFSGSGSGT EFTLTISSLQ SEDFAVYYCQ QDGSSPWTFG QGTKVEIK              108

SEQ ID NO: 26            moltype = AA  length = 118
FEATURE                  Location/Qualifiers
REGION                   1..118
                         note = Synthetic sequence
source                   1..118
                         mol_type = protein
                         organism = synthetic construct
SEQUENCE: 26
QVQLQESGPG LVKPSQTLSL TCTVSGFTFS HYTMHWVRQA PGQGLEWMGF ISYDGNNKYY  60
```

-continued

```
ADSVKGRFTI SRDNSKNTLY LQMNSLRAED TAVYYCARTG WLGPFDYWGQ GTLVTVSS      118

SEQ ID NO: 27              moltype = AA   length = 108
FEATURE                    Location/Qualifiers
REGION                     1..108
                           note = Synthetic sequence
source                     1..108
                           mol_type = protein
                           organism = synthetic construct
SEQUENCE: 27
AIQLTQSPSS LSASVGDRVT ITCRASQSVG SSYLAWYQQK PGKAPKLLIY GAFSRATGVP      60
SRFSGSGSGT EFTLTISSLQ PDDFATYYCQ QDGSSPWTFG QGTKVEIK                   108

SEQ ID NO: 28              moltype = AA   length = 118
FEATURE                    Location/Qualifiers
REGION                     1..118
                           note = Synthetic sequence
source                     1..118
                           mol_type = protein
                           organism = synthetic construct
SEQUENCE: 28
EVQLVQSGAE VKKPGATVKI SCKVSGFTFS HYTMHWIRQS PSRGLEWLGF ISYDGNYKYY      60
ADSVKGRFTI SRDNSKNTLY LQMNSLRAED TAVYYCARTG WLGPFDYWGQ GTLVTVSS       118

SEQ ID NO: 29              moltype = AA   length = 108
FEATURE                    Location/Qualifiers
REGION                     1..108
                           note = Synthetic sequence
source                     1..108
                           mol_type = protein
                           organism = synthetic construct
SEQUENCE: 29
EIVMTQSPAT LSVSPGERAT LSCRASQSVG SSYLAWYQQK PGKAPKLLIY GAFSRATGVP      60
SRFSGSGSGT DFTLTISSLQ PEDFATYYCQ QDGSSPWTFG QGTKVEIK                   108

SEQ ID NO: 30              moltype = AA   length = 118
FEATURE                    Location/Qualifiers
REGION                     1..118
                           note = Synthetic sequence
source                     1..118
                           mol_type = protein
                           organism = synthetic construct
SEQUENCE: 30
EVQLVQSGAE VKKPGATVKI SCKVSGFTFS HYTMHWIRQS PSRGLEWLGF ISYDGNYKYY      60
AKSVKGRFTI SRDNAKNSLY LQMNSLRAED TAVYYCARTG WLGPFDYWGQ GTLVTVSS       118

SEQ ID NO: 31              moltype = AA   length = 108
FEATURE                    Location/Qualifiers
REGION                     1..108
                           note = Synthetic sequence
source                     1..108
                           mol_type = protein
                           organism = synthetic construct
SEQUENCE: 31
EIVMTQSPAT LSVSPGERAT LSCRASQSVG SSYLAWYQQK PGKAPKLLIY GAFSRATGVP      60
SRFSGSGSGT DFTLTISSLQ PEDFATYYCQ QDGSSPWTFG QGTKVEIK                   108

SEQ ID NO: 32              moltype = AA   length = 118
FEATURE                    Location/Qualifiers
REGION                     1..118
                           note = Synthetic sequence
source                     1..118
                           mol_type = protein
                           organism = synthetic construct
SEQUENCE: 32
EVQLVQSGAE VKKPGATVKI SCKVSGFTFS HYTMHWIRQS PSRGLEWLGF ISYIGNYKYY      60
ADSVKGRFTI SRDNAKNSLY LQMNSLRAED TAVYYCARTG WLGPFDYWGQ GTLVTVSS       118

SEQ ID NO: 33              moltype = AA   length = 108
FEATURE                    Location/Qualifiers
REGION                     1..108
                           note = Synthetic sequence
source                     1..108
                           mol_type = protein
                           organism = synthetic construct
SEQUENCE: 33
EIVMTQSPAT LSVSPGERAT LSCRASQSVG SSYLAWYQQK PGKAPKLLIY GAFSRATGVP      60
SRFSGSGSGT DFTLTISSLQ PEDFATYYCQ QDGSSPWTFG QGTKVEIK                   108
```

-continued

```
SEQ ID NO: 34            moltype = AA  length = 118
FEATURE                  Location/Qualifiers
REGION                   1..118
                         note = Synthetic sequence
source                   1..118
                         mol_type = protein
                         organism = synthetic construct
SEQUENCE: 34
EVQLVQSGAE VKKPGATVKI SCKVSGFTFS HYTMHWIRQS PSRGLEWLGF ISYIGNYKYY  60
ADSMKGRFTI SRDNAKNSLY LQMNSLRAED TAVYYCARTG WLGPFDYWGQ GTLVTVSS    118

SEQ ID NO: 35            moltype = AA  length = 108
FEATURE                  Location/Qualifiers
REGION                   1..108
                         note = Synthetic sequence
source                   1..108
                         mol_type = protein
                         organism = synthetic construct
SEQUENCE: 35
EIVMTQSPAT LSVSPGERAT LSCRASQHVG SSYLAWYQQK PGKAPKLLIY GAFSRATGVP  60
SRFSGSGSGT DFTLTISSLQ PEDFATYYCQ QDGSSPWTFG QGTKVEIK              108

SEQ ID NO: 36            moltype = AA  length = 118
FEATURE                  Location/Qualifiers
REGION                   1..118
                         note = Synthetic sequence
source                   1..118
                         mol_type = protein
                         organism = synthetic construct
SEQUENCE: 36
EVQLVQSGAE VKKPGATVKI SCKVSGFTFS HYTMHWIRQS PSRGLEWLGF ISYIGNYKYY  60
ADSVKGRFTI SRDNAKNSLY LQMNSLRAED TAVYYCARTG WLGPFDYWGQ GTLVTVSS    118

SEQ ID NO: 37            moltype = AA  length = 108
FEATURE                  Location/Qualifiers
REGION                   1..108
                         note = Synthetic sequence
source                   1..108
                         mol_type = protein
                         organism = synthetic construct
SEQUENCE: 37
EIVMTQSPAT LSVSPGERAT LSCRASQHVG SSYLAWYQQK PGKAPKLLIY GAFSRATGVP  60
SRFSGSGSGT DFTLTISSLQ PEDFATYYCQ QDGSSPWTFG QGTKVEIK              108

SEQ ID NO: 38            moltype = AA  length = 118
FEATURE                  Location/Qualifiers
REGION                   1..118
                         note = Synthetic sequence
source                   1..118
                         mol_type = protein
                         organism = synthetic construct
SEQUENCE: 38
EVQLVQSGAE VKKPGATVKI SCKVSGFTFS HYTMHWIRQS PSRGLEWLGF ISYIGNYKYY  60
ADSMKGRFTI SRDNAKNSLY LQMNSLRAED TAVYYCARTG WLGPFDYWGQ GTLVTVSS    118

SEQ ID NO: 39            moltype = AA  length = 10
FEATURE                  Location/Qualifiers
REGION                   1..10
                         note = Synthetic sequence
source                   1..10
                         mol_type = protein
                         organism = synthetic construct
SEQUENCE: 39
GFTFSHYTMH                                                         10

SEQ ID NO: 40            moltype = AA  length = 17
FEATURE                  Location/Qualifiers
REGION                   1..17
                         note = Synthetic sequence
source                   1..17
                         mol_type = protein
                         organism = synthetic construct
SEQUENCE: 40
FISYDGNNKY YADSVKG                                                 17

SEQ ID NO: 41            moltype = AA  length = 9
FEATURE                  Location/Qualifiers
REGION                   1..9
                         note = Synthetic sequence
```

-continued

```
source                    1..9
                          mol_type = protein
                          organism = synthetic construct
SEQUENCE: 41
TGWLGPFDY                                                                  9

SEQ ID NO: 42             moltype = AA  length = 12
FEATURE                   Location/Qualifiers
REGION                    1..12
                          note = Synthetic sequence
source                    1..12
                          mol_type = protein
                          organism = synthetic construct
SEQUENCE: 42
RASQYVGSSY LA                                                             12

SEQ ID NO: 43             moltype = AA  length = 9
FEATURE                   Location/Qualifiers
REGION                    1..9
                          note = Synthetic sequence
source                    1..9
                          mol_type = protein
                          organism = synthetic construct
SEQUENCE: 43
GAFSRATGI                                                                  9

SEQ ID NO: 44             moltype = AA  length = 9
FEATURE                   Location/Qualifiers
REGION                    1..9
                          note = Synthetic sequence
source                    1..9
                          mol_type = protein
                          organism = synthetic construct
SEQUENCE: 44
QQDGSSPWT                                                                  9

SEQ ID NO: 45             moltype = AA  length = 17
FEATURE                   Location/Qualifiers
REGION                    1..17
                          note = Synthetic sequence
source                    1..17
                          mol_type = protein
                          organism = synthetic construct
SEQUENCE: 45
FIDYHGNNKY YADSVKG                                                        17

SEQ ID NO: 46             moltype = AA  length = 17
FEATURE                   Location/Qualifiers
REGION                    1..17
                          note = Synthetic sequence
source                    1..17
                          mol_type = protein
                          organism = synthetic construct
SEQUENCE: 46
FISYDGNNKI YADSVKG                                                        17

SEQ ID NO: 47             moltype = AA  length = 17
FEATURE                   Location/Qualifiers
REGION                    1..17
                          note = Synthetic sequence
source                    1..17
                          mol_type = protein
                          organism = synthetic construct
SEQUENCE: 47
FISYDGNYKY YADSVKG                                                        17

SEQ ID NO: 48             moltype = AA  length = 17
FEATURE                   Location/Qualifiers
REGION                    1..17
                          note = Synthetic sequence
source                    1..17
                          mol_type = protein
                          organism = synthetic construct
SEQUENCE: 48
FISYDGNYKY YAKSVKG                                                        17

SEQ ID NO: 49             moltype = AA  length = 17
FEATURE                   Location/Qualifiers
REGION                    1..17
```

-continued

```
                           note = Synthetic sequence
source                     1..17
                           mol_type = protein
                           organism = synthetic construct
SEQUENCE: 49
FISYHGNNKY EADSVKG                                                17

SEQ ID NO: 50              moltype = AA  length = 17
FEATURE                    Location/Qualifiers
REGION                     1..17
                           note = Synthetic sequence
source                     1..17
                           mol_type = protein
                           organism = synthetic construct
SEQUENCE: 50
FISYHGNNKY YADSVKG                                                17

SEQ ID NO: 51              moltype = AA  length = 17
FEATURE                    Location/Qualifiers
REGION                     1..17
                           note = Synthetic sequence
source                     1..17
                           mol_type = protein
                           organism = synthetic construct
SEQUENCE: 51
FISYIGNYKY YADSMKG                                                17

SEQ ID NO: 52              moltype = AA  length = 17
FEATURE                    Location/Qualifiers
REGION                     1..17
                           note = Synthetic sequence
source                     1..17
                           mol_type = protein
                           organism = synthetic construct
SEQUENCE: 52
FISYIGNYKY YADSVKG                                                17

SEQ ID NO: 53              moltype = AA  length = 9
FEATURE                    Location/Qualifiers
REGION                     1..9
                           note = Synthetic sequence
source                     1..9
                           mol_type = protein
                           organism = synthetic construct
SEQUENCE: 53
TGWLGPFDI                                                         9

SEQ ID NO: 54              moltype = AA  length = 12
FEATURE                    Location/Qualifiers
REGION                     1..12
                           note = Synthetic sequence
source                     1..12
                           mol_type = protein
                           organism = synthetic construct
SEQUENCE: 54
RASQHVGSSY LA                                                     12

SEQ ID NO: 55              moltype = AA  length = 12
FEATURE                    Location/Qualifiers
REGION                     1..12
                           note = Synthetic sequence
source                     1..12
                           mol_type = protein
                           organism = synthetic construct
SEQUENCE: 55
RASQSVGSSY LA                                                     12

SEQ ID NO: 56              moltype = AA  length = 12
FEATURE                    Location/Qualifiers
REGION                     1..12
                           note = Synthetic sequence
source                     1..12
                           mol_type = protein
                           organism = synthetic construct
SEQUENCE: 56
RASQYGGSSY LA                                                     12

SEQ ID NO: 57              moltype = AA  length = 12
FEATURE                    Location/Qualifiers
```

-continued

```
REGION                    1..12
                          note = Synthetic sequence
source                    1..12
                          mol_type = protein
                          organism = synthetic construct
SEQUENCE: 57
RISQYVGSSY LA                                                        12

SEQ ID NO: 58             moltype = AA  length = 9
FEATURE                   Location/Qualifiers
REGION                    1..9
                          note = Synthetic sequence
source                    1..9
                          mol_type = protein
                          organism = synthetic construct
SEQUENCE: 58
GAFSRATGV                                                            9
```

What is claimed is:

1. An anti-CTLA4 antibody or antibody fragment for use in a method for the treatment of small cell lung cancer, non-small cell lung cancer, renal cancer, liver cancer, melanoma, bladder cancer, cervical cancer, hepatic cancer, gastric cancer or kidney cancer in a patient with said cancer; said anti-CTLA-4 antibody or antigen binding antibody fragment comprising a heavy chain variable region including three complementarity determining regions, said regions having H1, H2, and H3 sequences, wherein:

```
                                        (SEQ ID NO: 1)
(a) the H1 sequence is GFTFSHYTMH;

(SEQ ID NO: 2)
(b) the H2 sequence is FIX₁YX₂GNX₃KX₄X₅AX₆SX₇KG;
and (SEQ ID NO: 3)
(c) the H3 sequence is TGWLGPFDX₈,
``` wherein $X_1$ is S or D; $X_2$ is D, H or I, $X_3$ is N or Y; $X_4$ is Y or I; $X_5$ is Y or E; $X_6$ is D or K; $X_7$ is V or M; and $X_8$ is Y or I; and a light chain variable region including three complementarity determining regions having L1, L2, and L3 sequences, wherein:

```
                                        (SEQ ID NO: 4)
(a) the L1 sequence is RX₉SQX₁₀X₁₁GSSYLA;

(SEQ ID NO: 5)
(b) the L2 sequence is GAFSRATGX₁₂;
and (SEQ ID NO: 6)
(c) the L3 sequence is QQDGSSPWT,
``` wherein $X_9$ is A or I; $X_{10}$ is Y, S or H; $X_{11}$ is V or G; $X_{12}$ is V or I.

2. The anti-CTLA4 antibody or antigen binding antibody fragment of claim 1, wherein the H2 sequence is selected from

```
                                        (SEQ ID NO: 45)
FIDYHGNNKYYADSVKG, (SEQ ID NO: 46)
FISYDGNNKIYADSVKG,
```

-continued

```
                                        (SEQ ID NO: 40)
FISYDGNNKYYADSVKG, (SEQ ID NO: 47)
FISYDGNYKYYADSVKG, (SEQ ID NO: 48)
FISYDGNYKYYAKSVKG, (SEQ ID NO: 49)
FISYHGNNKYEADSVKG, (SEQ ID NO: 50)
FISYHGNNKYYADSVKG, (SEQ ID NO: 51)
FISYIGNYKYYADSMKG, (SEQ ID NO: 52)
FISYIGNYKYYADSVKG.
```

3. The anti-CTLA4 antibody or antigen binding antibody fragment of claim 1, wherein the H3 sequence is selected from TGWLGPFDY (SEQ ID NO: 41) and TGWLGPFDI (SEQ ID NO: 53).

4. The anti-CTLA4 antibody or antigen binding antibody fragment of claim 1, wherein the heavy chain variable region has an amino acid sequence selected from SEQ ID NOS: 8, 10, 12, 14, 16, 18, 20, 22, 24, 26, 28, 30, 32, 34, 36, 38.

5. The anti-CTLA4 antibody or antigen binding antibody fragment of claim 1, wherein the L1 sequence is selected from RASQHVGSSYLA (SEQ ID NO: 54), RASQSVGS-SYLA (SEQ ID NO: 55), RASQYGGSSYLA (SEQ ID NO: 56), RASQYVGSSYLA (SEQ ID NO: 42), and RIS-QYVGSSYLA (SEQ ID NO: 57).

6. The anti-CTLA4 antibody or antigen binding antibody fragment of claim 5, wherein the L2 sequence is selected from GAFSRATGI (SEQ ID NO: 43) and GAFSRATGV (SEQ ID NO: 58).

7. The anti-CTLA4 antibody or antigen binding antibody fragment of claim 1, wherein the light chain variable region has an amino acid sequence selected from SEQ ID NOS: 7, 9, 11, 13, 15, 17, 19, 21, 23, 25, 27, 29, 31, 33, 35, and 37.

8. The antibody or antibody fragment of claim 1, wherein the antibody or antibody fragment has a higher binding affinity to CTLA4 protein at pH in a tumor microenvironment in a range of from 5.0 to 6.8 in comparison with a pH in a non-tumor microenvironment in a range of from 7.0 to 7.6.

9. The antibody or antibody fragment of claim 8, wherein the antibody or antibody fragment has a ratio of binding affinity to the CTLA4 protein at pH 6.0 in a tumor microenvironment to a binding affinity to the CTLA4 protein at pH 7.4 in a non-tumor microenvironment of at least about 1.5:1.

10. A composition for use in a method for the treatment of small cell lung cancer, non-small cell lung cancer, renal cancer, liver cancer, melanoma, bladder cancer, cervical cancer, hepatic cancer, gastric cancer or kidney cancer in a patient with said cancer; said composition comprising the anti-CTLA-4 antibody or antigen binding antibody fragment of claim 1 and at least one agent selected from a chemotherapeutic agent, a radioactive atom, a cytostatic agent and a cytotoxic agent.

11. The composition of claim 10, wherein the antibody or antibody fragment and the at least one agent are covalently bonded to a linker molecule.

12. The composition of claim 11, wherein the at least one agent is selected from maytansinoids, auristatins, dolastatins, calicheamicin, pyrrolobenzodiazepines, and anthracyclines.

13. The antibody or antibody fragment of claim 8, wherein the antibody or antibody fragment has a ratio of binding affinity to the CTLA4 protein at a pH in a tumor microenvironment of from 5.0 to 6.8 to a binding affinity to the CTLA4 protein at a pH in a non-tumor microenvironment of 7.0 to 7.6 of at least about 1.5:1.

14. The antibody or antibody fragment of claim 13, wherein the antibody or antibody fragment the ratio of binding affinity to the CTLA4 protein is at least about 2:1.

15. The anti-CTLA4 antibody or antigen binding antibody fragment of claim 4, wherein the light chain variable region has an amino acid sequence selected from SEQ ID NOS: 7, 9, 11, 13, 15, 17, 19, 21, 23, 25, 27, 29, 31, 33, 35, and 37.

16. The anti-CTLA4 antibody or antigen binding antibody fragment of claim 2, wherein the H3 sequence is selected from TGWLGPFDY (SEQ ID NO: 41) and TGWLGPFDI (SEQ ID NO: 53).

17. The anti-CTLA4 antibody or antigen binding antibody fragment of claim 16, wherein the L1 sequence is selected from RASQHVGSSYLA (SEQ ID NO: 54), RASQSVGS-SYLA (SEQ ID NO: 55), RASQYGGSSYLA (SEQ ID NO: 56), RASQYVGSSYLA (SEQ ID NO: 42), and RIS-QYVGSSYLA (SEQ ID NO: 57).

18. The anti-CTLA4 antibody or antigen binding antibody fragment of claim 17, wherein the L2 sequence is selected from GAFSRATGI (SEQ ID NO: 43) and GAFSRATGV (SEQ ID NO: 58).

* * * * *